(12) United States Patent
Pardo-Fernandez et al.

(10) Patent No.: US 7,364,730 B2
(45) Date of Patent: Apr. 29, 2008

(54) HUMAN K+ CHANNEL AND PROGNOSING APPLICATIONS THEREOF

(75) Inventors: Luis A Pardo-Fernandez, Gottingen (DE); Walter Stuhmer, Gottingen (DE); Synnove Beckh, Gottingen (DE); Andrea Bruggemann, Frankfurt (DE); Donato Del Camino Fernandez-Miranda, Boston, MA (US); Araceli Sanchez Perez, Gottingen (DE); Rudiger Weseloh, Gottingen (DE)

(73) Assignee: Max-Planck-Gesellschaft zur Forderung der Wissenschaften, E.V., Berlin (DE)

( * ) Notice: Subject to any disclaimer, the term of this patent is extended or adjusted under 35 U.S.C. 154(b) by 917 days.

(21) Appl. No.: 10/188,308

(22) Filed: Jul. 1, 2002

(65) Prior Publication Data

US 2003/0077735 A1   Apr. 24, 2003

Related U.S. Application Data

(60) Division of application No. 09/694,777, filed on Oct. 23, 2000, now Pat. No. 6,638,736, which is a continuation of application No. PCT/EP99/02695, filed on Apr. 21, 1999.

(30) Foreign Application Priority Data

Apr. 21, 1998  (EP) ................................... 98107268

(51) Int. Cl.
*G01N 27/26* (2006.01)
*G01N 33/53* (2006.01)
*A61K 39/395* (2006.01)
*A61K 38/00* (2006.01)

(52) U.S. Cl. ...................... 424/130.1; 435/7.1; 435/7.2

(58) Field of Classification Search ...................... None
See application file for complete search history.

(56) References Cited

FOREIGN PATENT DOCUMENTS

WO   WO 92/11034   7/1992
WO   WO 94/18961   9/1994

OTHER PUBLICATIONS

Finch PW, Murphy F, Cardinale I, Krueger JG, 1997, Altered expression of keratinocyte growth factor and its receptor in psoriasis, Am J Pathol. 151(6): 1619-1628.*

J. Ludwig, et al., "Functional expression of a rat homologue of the voltage gated *ether a go-go* potassium channel reveals differences in selectivity and activation kinetics between the *Drosophila* channel and its mammalian counterpart," *The EMBO Journal*, 13(19), pp. 4451-4458 (1994).

T. Occhiodoro, et al., "Cloning of a human *ether-a-go-go* potassium channel expressed in myoblasts at the onset of fusion," *FEBS Letters*, 434, pp. 177-182 (1998).

H. Suessbrich, et al., "Blockade of HERG channels expressed in *Xenopus* oocytes by the histamine receptor antagonists terfenadine and astemizole," *FEBS Letters*, 385, pp. 77-80 (1996).

M.C. Trudeau, et al., "HERG, a human inward rectifier in the voltage-gated potassium channel family," *Science*, 269, pp. 92-95 (1995).

J.W. Warmke, et al., "A family of potassium channel genes related to *eag* in *Drosophila* and mammals," *Proc. Natl. Acad. Sci. USA*. 91, pp. 3438-3442 (1994).

* cited by examiner

*Primary Examiner*—Eileen O'Hara
*Assistant Examiner*—Sandra Wegert
(74) *Attorney, Agent, or Firm*—James F. Haley, Jr.; Ropes & Gray LLP

(57) ABSTRACT

The present invention relates to a novel human K+ ion channel, to nucleic acid molecules encoding the same and to vectors comprising said nucleic acid molecules. The invention additionally relates to antibodies specifically directed to the novel K+ ion channel and to pharmaceutical compositions and diagnostic kits containing at least one of the above-mentioned components. Furthermore, the present invention relates to methods of treating a disease caused by malfunction of the polypeptide of the present invention or by the (over)expression of the nucleic acid molecule of the invention comprising administering an inhibitor of said (over)expression or of ion channel function or an inhibitor abolishing said malfunction to a patient in need thereof. Methods of devising drugs for treating or preventing the above-mentioned disease, methods of inhibiting cell proliferation and methods of prognosing cancer are additional embodiments comprised by the present invention. The invention also envisages specific antisense or gene therapies on the basis of the nucleic acid molecule of the invention for inhibiting undesired cellular proliferation, for example, in connection with cancer or in neurodegenerative diseases.

9 Claims, 37 Drawing Sheets

Figure 1:
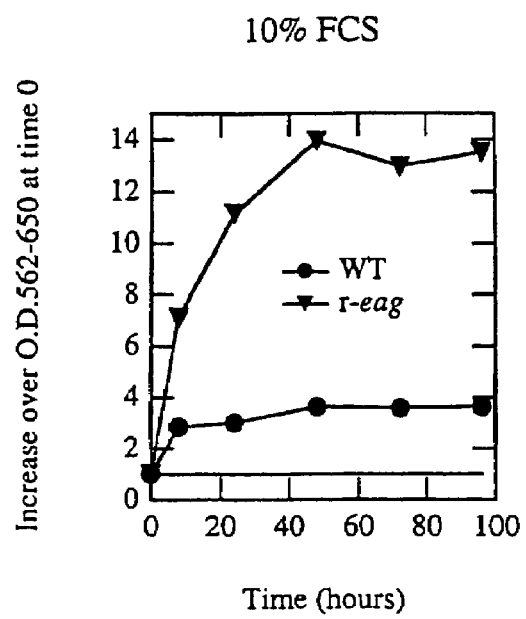

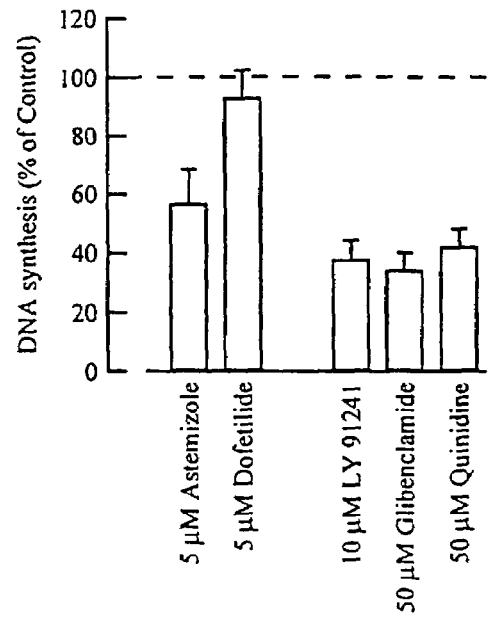
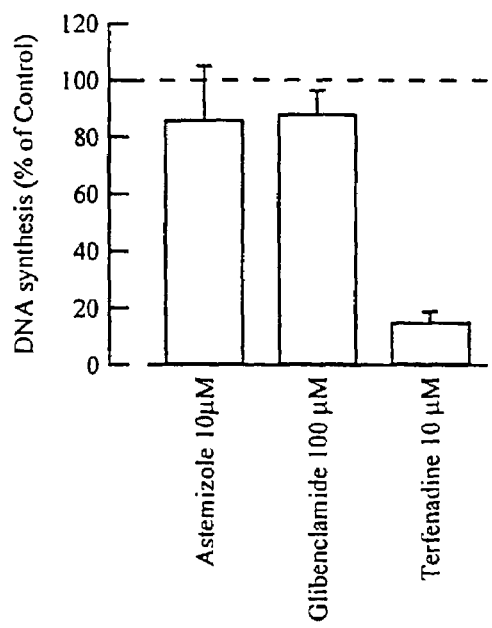
Fig. 7

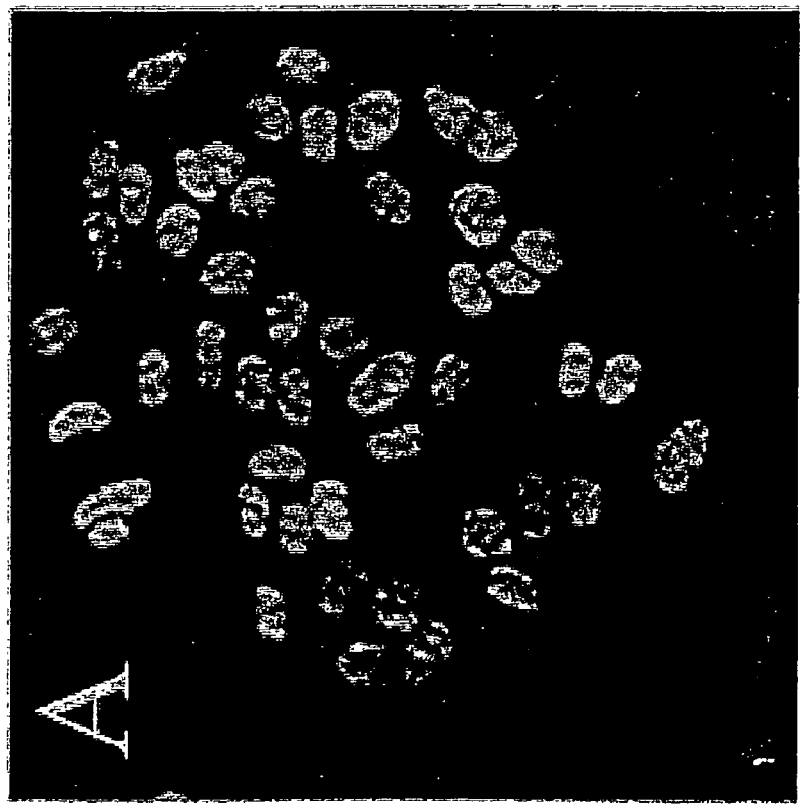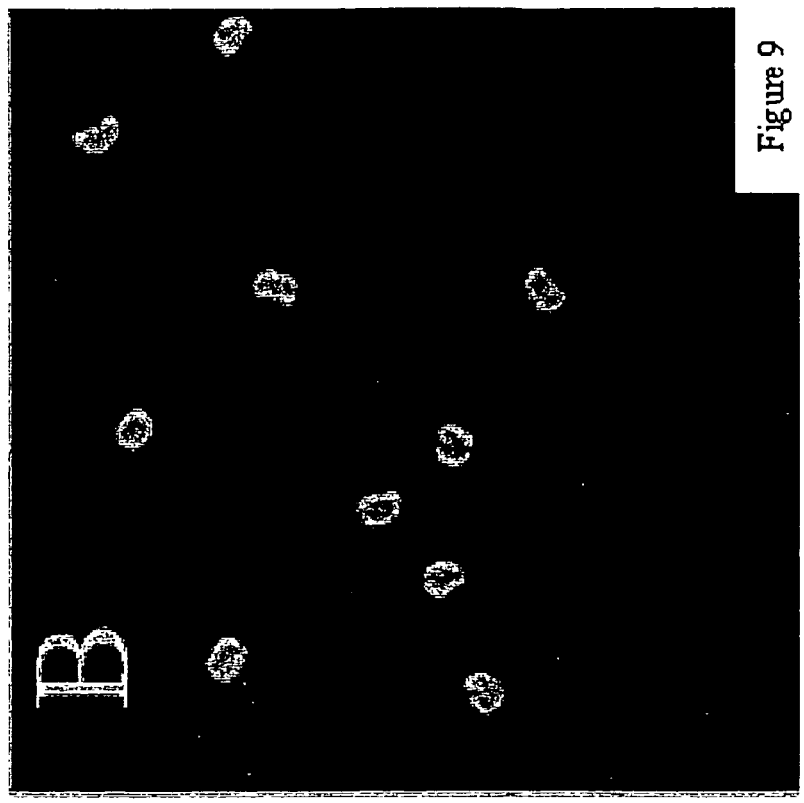
Figure 9

```
heag1  M T M A G G R R G L V A P Q N T F L E N  20
heag2  M T M A G G R R G L V A P Q N T F L E N  20
beag1  M T M A G G R K G L V A P Q N T F L E N  20
beag2  M T M A G G R K G L V A P Q N T F L E N  20
meag   M T M A G G R R G L V A P Q N T F L E N  20
reag   M T M A G G R R G L V A P Q N T F L E N  20 heag1  I V R R S N D T N F V L G N A Q I V D W  40
heag2  I V R R S N D T N F V L G N A Q I V D W  40
beag1  I V R R S N D T N F V L G N A Q I V D W  40
beag2  I V R R S N D T N F V L G N A Q I V D W  40
meag   I V R R S N D T N F V L G N A Q I V D W  40
reag   I V R R S N D T N F V L G N A Q I V D W  40 heag1  P I V Y S N D G F C K L S G Y H R A E V  60
heag2  P I V Y S N D G F C K L S G Y H R A E V  60
beag1  P I V Y S N D G F C K L S G Y H R A E V  60
beag2  P I V Y S N D G F C K L S G Y H R A E V  60
meag   P I V Y S N D G F C K L S G Y H R A E V  60
reag   P I V Y S N D G F C K L S G Y H R A E V  60 heag1  M Q K S S T C S F M Y G E L T D K D T I  80
heag2  M Q K S S T C S F M Y G E L T D K D T I  80
beag1  M Q K S S T C S F M Y G E L T D K D T I  80
beag2  M Q K S S T C S F M Y G E L T D K D T I  80
meag   M Q K S S A C S F M Y G E L T D K D T V  80
reag   M Q K S S A C S F M Y G E L T D K D T V  80 heag1  E K V R Q T F E N Y E M N S F E I L M Y  100
heag2  E K V R Q T F E N Y E M N S F E I L M Y  100
beag1  E K V R Q T F E N Y E M N S F E I L M Y  100
beag2  E K V R Q T F E N Y E M N S F E I L M Y  100
meag   E K V R Q T F E N Y E M N S F E I L M Y  100
reag   E K V R Q T F E N Y E M N S F E I L M Y  100
```

Fig. 11

```
heag1  K K N R T P V W F F V K I A P I R N E Q  120
heag2  K K N R T P V W F F V K I A P I R N E Q  120
beag1  K K N R T P V W F F V K I A P I R N E Q  120
beag2  K K N R T P V W F F V K I A P I R N E Q  120
meag   K K N R T P V W F F V K I A P I R N E Q  120
reag   K K N R T P V W F F V K I A P I R N E Q  120 heag1  D K V V L F L C T F S D I T A F K Q P I  140
heag2  D K V V L F L C T F S D I T A F K Q P I  140
beag1  D K V V L F L C T F S D I T A F K Q P I  140
beag2  D K V V L F L C T F S D I T A F K Q P I  140
meag   D K V V L F L C T F S D I T A F K Q P I  140
reag   D K V V L F L C T F S D I T A F K Q P I  140 heag1  E D D S C K G W G K F A R L T R A L T S  160
heag2  E D D S C K G W G K F A R L T R A L T S  160
beag1  E D D S C K G W G K F A R L T R A L T S  160
beag2  E D D S C K G W G K F A R L T R A L T S  160
meag   E D D S C K G W G K F A R L T R A L T S  160
reag   E D D S C K G W G K F A R L T R A L T S  160 heag1  S R G V L Q Q L A P S V Q K G E N V H K  180
heag2  S R G V L Q Q L A P S V Q K G E N V H K  180
beag1  S R G V L Q Q L A P S V Q K G E N V H K  180
beag2  S R G V L Q Q L A P S V Q K G E N V H K  180
meag   S R G V L Q Q L A P S V Q K G E N V H K  180
reag   S R G V L Q Q L A P S V Q K G E N V H K  180 heag1  H S R L A E V L Q L G S D I L P Q Y K Q  200
heag2  H S R L A E V L Q L G S D I L P Q Y K Q  200
beag1  H S R L A E V L Q L G S D I L P Q Y K Q  200
beag2  H S R L A E V L Q L G S D I L P Q Y K Q  200
meag   H S R L A E V L Q L G S D I L P Q Y K Q  200
reag   H S R L A E V L Q L G S D I L P Q Y K Q  200
```

Fig. 11 cont.

```
heag1  E A P K T P P H I I L H Y C V F K T T W  220
heag2  E A P K T P P H I I L H Y C V F K T T W  220
beag1  E A P K T P P H I I L H Y C V F K T T W  220
beag2  E A P K T P P H I I L H Y C V F K T T W  220
meag   E A P K T P P H I I L H Y C V F K T T W  220
reag   E A P K T P P H I I L H Y C V F K T T W  220 heag1  D W I I L I L T F Y T A I L V P Y N V S  240
heag2  D W I I L I L T F Y T A I L V P Y N V S  240
beag1  D W I I L I L T F Y T A I L V P Y N V S  240
beag2  D W I I L I L T F Y T A I L V P Y N V S  240
meag   D W I I L I L T F Y T A I L V P Y N V S  240
reag   D W I I L I L T F Y T A I L V P Y N V S  240 heag1  F K T R Q N N V A W L V V D S I V D V I  260
heag2  F K T R Q N N V A W L V V D S I V D V I  260
beag1  F K T R Q N N V A W L V V D S I V D V I  260
beag2  F K T R Q N N V A W L V V D S I V D V I  260
meag   F K T R Q N N V A W L V V D S I V D V I  260
reag   F K T R Q N N V A W L V V D S I V D V I  260 heag1  F L V D I V L N F H T T F V G P A G E V  280
heag2  F L V D I V L N F H T T F V G P A G E V  280
beag1  F L V D I V L N F H T T F V G P A G E V  280
beag2  F L V D I V L N F H T T F V G P A G E V  280
meag   F L V D I V L N F H T T F V G P A G E V  280
reag   F L V D I V L N F H T T F V G P A G E V  280 heag1  I S D P K L I R M N Y L K T W F V I D L  300
heag2  I S D P K L I R M N Y L K T W F V I D L  300
beag1  I S D P K L I R M N Y L K T W F V I D L  300
beag2  I S D P K L I R M N Y L K T W F V I D L  300
meag   I S D P K L I R M N Y L K T W F V I D L  300
reag   I S D P K L I R M N Y L K T W F V I D L  300
```

Fig. 11 cont.

```
heag1  L S C L P Y D V I N A F E N V D E - - -  317
heag2  L S C L P Y D V I N A F E N V D E V S A  320
beag1  L S C L P Y D V I N A F E N V D E - - -  317
beag2  L S C L P Y D V I N A F E N V D E V S A  320
meag   L S C L P Y D V I N A F E N V D E V S A  320
reag   L S C L P Y D V I N A F E N V D E - - -  317 heag1  - - - - - - - - - - - - - - - - - - - -  317
heag2  F M G D P G K I G F A D Q I P P P L E G  340
beag1  - - - - - - - - - - - - - - - - - - - -  317
beag2  F M G D P G K I G F A D Q I P P P L E G  340
meag   F M G D P G K I G F A D Q I P P P L E G  340
reag   - - - - - - - - - - - - - - - - - - - -  317 heag1  - - - - G I S S L F S S L K V V R L L R  333
heag2  R E S Q G I S S L F S S L K V V R L L R  360
beag1  - - - - G I S S L F S S L K V V R L L R  333
beag2  R E S Q G I S S L F S S L K V V R L L R  360
meag   R E S Q G I S S L F S S L K V V R L L R  360
reag   - - - - G I S S L F S S L K V V R L L R  333 heag1  L G R V A R K L D H Y I E Y G A A V L V  353
heag2  L G R V A R K L D H Y I E Y G A A V L V  380
beag1  L G R V A R K L D H Y I E Y G A A V L V  353
beag2  L G R V A R K L D H Y I E Y G A A V L V  380
meag   L G R V A R K L D H Y I E Y G A A V L V  380
reag   L G R V A R K L D H Y I E Y G A A V L V  353 heag1  L L V C V F G L A A H W M A C I W Y S I  373
heag2  L L V C V F G L A A H W M A C I W Y S I  400
beag1  L L V C V F G L A A H W M A C I W Y S I  373
beag2  L L V C V F G L A A H W M A C I W Y S I  400
meag   L L V C V F G L A A H W M A C I W Y S I  400
reag   L L V C V F G L A A H W M A C I W Y S I  373
```

Fig. 11 cont.

```
heag1  G D Y E I F D E D T K T I R N N S W L Y  393
heag2  G D Y E I F D E D T K T I R N N S W L Y  420
beag1  G D Y E I F D E D T K T I R N N S W L Y  393
beag2  G D Y E I F D E D T K T I R N N S W L Y  420
meag   G D Y E I F D E D T K T I R N N S W L Y  420
reag   G D Y E I F D E D T K T I R N N S W L Y  393 heag1  Q L A M D I G T P Y Q F N G S G S G K W  413
heag2  Q L A M D I G T P Y Q F N G S G S G K W  440
beag1  Q L A M D I G T P Y Q F N G S G S G K W  413
beag2  Q L A M D I G T P Y Q F N G S G S G K W  440
meag   Q L A L D I G T P Y Q F N G S G S G K W  440
reag   Q L A L D I G T P Y Q F N G S G S G K W  413 heag1  E G G P S K N S V Y I S S L Y F T M T S  433
heag2  E G G P S K N S V Y I S S L Y F T M T S  460
beag1  E G G P S K N S V Y I S S L Y F T M T S  433
beag2  E G G P S K N S V Y I S S L Y F T M T S  460
meag   E G G P S K N S V Y I S S L Y F T M T S  460
reag   E G G P S K N S V Y I S S L Y F T M T S  433 heag1  L T S V G F G N I A P S T D I E K I F A  453
heag2  L T S V G F G N I A P S T D I E K I F A  480
beag1  L T S V G F G N I A P S T D I E K I F A  453
beag2  L T S V G F G N I A P S T D I E K I F A  480
meag   L T S V G F G N I A P S T D I E K I F A  480
reag   L T S V G F G N I A P S T D I E K I F A  453 heag1  V A I M M I G S L L Y A T I F G N V T T  473
heag2  V A I M M I G S L L Y A T I F G N V T T  500
beag1  V A I M M I G S L L Y A T I F G N V T T  473
beag2  V A I M M I G S L L Y A T I F G N V T T  500
meag   V A I M M I G S L L Y A T I F G N V T T  500
reag   V A I M M I G S L L Y A T I F G N V T T  473
```

Fig. 11 cont.

| | | |
|---|---|---|
| heag1 | I F Q Q M Y A N T N R Y H E M L N S V R | 493 |
| heag2 | I F Q Q M Y A N T N R Y H E M L N S V R | 520 |
| beag1 | I F Q Q M Y A N T N R Y H E M L N S V R | 493 |
| beag2 | I F Q Q M Y A N T N R Y H E M L N S V R | 520 |
| meag  | I F Q Q M Y A N T N R Y H E M L N S V R | 520 |
| reag  | I F Q Q M Y A N T N R Y H E M L N S V R | 493 |
| | | |
| heag1 | D F L K L Y Q V P K G L S E R V M D Y I | 513 |
| heag2 | D F L K L Y Q V P K G L S E R V M D Y I | 540 |
| beag1 | D F L K L Y Q V P K G L S E R V M D Y I | 513 |
| beag2 | D F L K L Y Q V P K G L S E R V M D Y I | 540 |
| meag  | D F L K L Y Q V P K G L S E R V M D Y I | 540 |
| reag  | D F L K L Y Q V P K G L S E R V M D Y I | 513 |
| | | |
| heag1 | V S T W S M S R G I D T E K V L Q I C P | 533 |
| heag2 | V S T W S M S R G I D T E K V L Q I C P | 560 |
| beag1 | V S T W S M S R G I D T E K V L Q I C P | 533 |
| beag2 | V S T W S M S R G I D T E K V L Q I C P | 560 |
| meag  | V S T W S M S R G I D T E K V L Q I C P | 560 |
| reag  | V S T W S M S R G I D T E K V L Q I C P | 533 |
| | | |
| heag1 | K D M R A D I C V H L N R K V F K E H P | 553 |
| heag2 | K D M R A D I C V H L N R K V F K E H P | 580 |
| beag1 | K D M R A D I C V H L N R K V F K E H P | 553 |
| beag2 | K D M R A D I C V H L N R K V F K E H P | 580 |
| meag  | K D M R A D I C V H L N R K V F K E H P | 580 |
| reag  | K D M R A D I C V H L N R K V F K E H P | 553 |
| | | |
| heag1 | A F R L A S D G C L R A L A M E F Q T V | 573 |
| heag2 | A F R L A S D G C L R A L A M E F Q T V | 600 |
| beag1 | A F R L A S D G C L R A L A M E F Q T V | 573 |
| beag2 | A F R L A S D G C L R A L A M E F Q T V | 600 |
| meag  | A F R L A S D G C L R A L A M E F Q T V | 600 |
| reag  | A F R L A S D G C L R A L A M E F Q T V | 573 |

Fig. 11 cont.

```
heag1  H C A P G D L I Y H A G E S V D S L C F  593
heag2  H C A P G D L I Y H A G E S V D S L C F  620
beag1  H C A P G D L I Y H A G E S V D S L C F  593
beag2  H C A P G D L I Y H A G E S V D S L C F  620
meag   H C A P G D L I Y H A G E S V D S L C F  620
reag   H C A P G D L I Y H A G E S V D S L C F  593 heag1  V V S G S L E V I Q D D E V V A I L G K  613
heag2  V V S G S L E V I Q D D E V V A I L G K  640
beag1  V V S G S L E V I Q D D E V V A I L G K  613
beag2  V V S G S L E V I Q D D E V V A I L G K  640
meag   V V S G S L E V I Q D D E V V A I L G K  640
reag   V V S G S L E V I Q D D E V V A I L G K  613 heag1  G D V F G D V F W K E A T L A Q S C A N  633
heag2  G D V F G D V F W K E A T L A Q S C A N  660
beag1  G D V F G D V F W K E A T L A Q S C A N  633
beag2  G D V F G D V F W K E A T L A Q S C A N  660
meag   G D V F G D V F W K E A T L A Q S C A N  660
reag   G D V F G D V F W K E A T L A Q S C A N  633 heag1  V R A L T Y C D L H V I K R D A L Q K V  653
heag2  V R A L T Y C D L H V I K R D A L Q K V  680
beag1  V R A L T Y C D L H V I K R D A L Q K V  653
beag2  V R A L T Y C D L H V I K R D A L Q K V  680
meag   V R A L T Y C D L H V I K R D A L Q K V  680
reag   V R A L T Y C D L H V I K R D A L Q K V  653 heag1  L E F Y T A F S H S F S R N L I L T Y N  673
heag2  L E F Y T A F S H S F S R N L I L T Y N  700
beag1  L E F Y T A F S H S F S R N L I L T Y N  673
beag2  L E F Y T A F S H S F S R N L I L T Y N  700
meag   L E F Y T A F S H S F S R N L I L T Y N  700
reag   L E F Y T A F S H S F S R N L I L T Y N  673
```

Fig. 11 cont.

```
heag1  L R K R I V F R K I S D V K R E E E E R  693
heag2  L R K R I V F R K I S D V K R E E E E R  720
beag1  L R K R I V F R K I S D V K R E E E E R  693
beag2  L R K R I V F R K I S D V K R E E E E R  720
meag   L R K R I V F R K I S D V K R E E E E R  720
reag   L R K R I V F R K I S D V K R E E E E R  693 heag1  M K R K N E A P L I L P P D H P V R R L  713
heag2  M K R K N E A P L I L P P D H P V R R L  740
beag1  M K R K N E A P L I L P P D H P V R R L  713
beag2  M K R K N E A P L I L P P D H P V R R L  740
meag   M K R K N E A P L I L P P D H P V R R L  740
reag   M K R K N E A P L I L P P D H P V R R L  713 heag1  F Q R F R Q Q K E A R L A A E R G G R D  733
heag2  F Q R F R Q Q K E A R L A A E R G G R D  760
beag1  F Q R F R Q Q K E A R L A A E R G G R D  733
beag2  F Q R F R Q Q K E A R L A A E R G G R D  760
meag   F Q R F R Q Q K E A R L A A E R G G R D  760
reag   F Q R F R Q Q K E A R L A A E R G G R D  733 heag1  L D D L D V E K G N V L T E H A S A N H  753
heag2  L D D L D V E K G N V L T E H A S A N H  780
beag1  L D D L D V E K G S V L T E H - - S H H  751
beag2  L D D L D V E K G S V L T E H - - S H H  778
meag   L D D L D V E K G N A L T D H T S A N H  780
reag   L D D L D V E K G N A L T D H T S A N H  753 heag1  S L V K A S V V T V R E S P A T P V S F  773
heag2  S L V K A S V V T V R E S P A T P V S F  800
beag1  G L A K A S V V T V R E S P A T P V A F  771
beag2  G L A K A S V V T V R E S P A T P V A F  798
meag   S L V K A S V V T V R E S P A T P V S F  800
reag   S L V K A S V V T V R E S P A T P V S F  773
```

Fig. 11 cont.

```
heag1  Q A A S T S G V P D H A K L Q A P G S E  793
heag2  Q A A S T S G V P D H A K L Q A P G S E  820
beag1  P A A A A P A G L D H A R L Q A P G A E  791
beag2  P A A A A P A G L D H A R L Q A P G A E  818
meag   Q A A T T S T M S D H A K L H A P G S E  820
reag   Q A A S T S T V S D H A K L H A P G S E  793 heag1  C L G P K G G G G D C A K R K S W A R F  813
heag2  C L G P K G G G G D C A K R K S W A R F  840
beag1  G L G P K A G G A D C A K R K G W A R F  811
beag2  G L G P K A G G A D C A K R K G W A R F  838
meag   C L G P K A V S C D P A K R K G W A R F  840
reag   C L G P K A G G G D P A K R K G W A R F  813 heag1  K D A C G K S E D W N K V S K A E S M E  833
heag2  K D A C G K S E D W N K V S K A E S M E  860
beag1  K D A C G Q A E D W S K V S K A E S M E  831
beag2  K D A C G Q A E D W S K V S K A E S M E  858
meag   K D A C G K G E D W N K V S K A E S M E  860
reag   K D A C G K G E D W N K V S K A E S M E  833 heag1  T L P E R T K A S G E A T L K K T D S C  853
heag2  T L P E R T K A S G E A T L K K T D S C  880
beag1  T L P E R T K A A G E A T L K K T D S C  851
beag2  T L P E R T K A A G E A T L K K T D S C  878
meag   T L P E R T K A P G E A T L K K T D S C  880
reag   T L P E R T K A S G E A T L K K T D S C  853 heag1  D S G I T K S D L R L D N V G E A R S P  873
heag2  D S G I T K S D L R L D N V G E A R S P  900
beag1  D S G I T K S D L R L D N V G E A R S P  871
beag2  D S G I T K S D L R L D N V G E A R S P  898
meag   D S G I T K S D L R L D N V G E T R S P  900
reag   D S G I T K S D L R L D N V G E A R S P  873
```

Fig. 11 cont.

```
heag1  Q D R S P I L A E V K H S F Y P I P E Q  893
heag2  Q D R S P I L A E V K H S F Y P I P E Q  920
beag1  Q D R S P I L A E V K H S F Y P I P E Q  891
beag2  Q D R S P I L A E V K H S F Y P I P E Q  918
meag   Q D R S P I L A E V K H S F Y P I P E Q  920
reag   Q D R S P I L A E V K H S F Y P I P E Q  893 heag1  T L Q A T V L E V R H E L K E D I K A L  913
heag2  T L Q A T V L E V R H E L K E D I K A L  940
beag1  T L Q A A V L E V K H E L K E D I K A L  911
beag2  T L Q A A V L E V K H E L K E D I K A L  938
meag   T L Q A T V L E V K Y E L K E D I K A L  940
reag   T L Q A T V L E V K H E L K E D I K A L  913 heag1  N A K M T N I E K Q L S E I L R I L T S  933
heag2  N A K M T N I E K Q L S E I L R I L T S  960
beag1  S T K M T S I E K Q L S E I L R I L T S  931
beag2  S T K M T S I E K Q L S E I L R I L T S  958
meag   N A K M T S I E K Q L S E I L R I L M S  960
reag   N A K M T S I E K Q L S E I L R I L M S  933 heag1  R R S S Q S P Q E L F E I S R P Q S P E  953
heag2  R R S S Q S P Q E L F E I S R P Q S P E  980
beag1  R R S S Q S P Q E L F E I S R P Q S P E  951
beag2  R R S S Q S P Q E L F E I S R P Q S P E  978
meag   R G S A Q S P Q E T G E I S R P Q S P E  980
reag   R G S S Q S P Q D T C E V S R P Q S P E  953 heag1  S E R D I F G A S                        962
heag2  S E R D I F G A S                        989
beag1  S E R D I F G A S                        960
beag2  S E R D I F G A S                        987
meag   S D R D I F G A S                        989
reag   S D R D I F G A S                        962
```

Fig. 11 cont.

| DNA | Colonies≥0.1 mm |
|---|---|
| rEAG-pTracer | 9.9 ± 2.4 |
| rEAG-pcDNA3 | 8.5 ± 3.2 |
| rKv1.4-pTracer | 0 |
| rKv1.4-pcDNA3 | 1.4 ± 0.7 |
| GFP-pcDNA3 | 0.8 ± 0.5 |
| Transfection buffer | 0.6 ± 0.2 |
| No treatment | 0 |

Fig. 14

HUMAN K+ CHANNEL AND PROGNOSING APPLICATIONS THEREOF

This application is a division of U.S. application Ser. No. 09/694,777, filed Oct. 23, 2000 now U.S. Pat. No. 6,638,736, which is a continuation of international application PCT/EP99/02695, filed Apr. 21, 1999, which designated the United States.

The present invention relates to a novel human $K^+$ ion channel, to nucleic acid molecules encoding the same and to vectors comprising said nucleic acid molecules. The invention additionally relates to antibodies specifically directed to the novel $K^+$ ion channel and to pharmaceutical compositions and diagnostic kits containing at least one of the above-mentioned components. Furthermore, the present invention relates to methods of treating a disease caused by malfunction of the polypeptide of the present invention or by the (over)expression of the nucleic acid molecule of the invention comprising administering an inhibitor of said (over)expression or of ion channel function or an inhibitor abolishing said malfunction to a patient in need thereof. Methods of devising drugs for treating or preventing the above-mentioned disease, methods of inhibiting cell proliferation and methods of prognosing cancer are additional embodiments comprised by the present invention. The invention also envisages specific antisense or gene therapies on the basis of the nucleic acid molecule of the invention for inhibiting undesired cellular proliferation, for example, in connection with cancer or in neurodegenerative diseases.

Potassium channels are a relevant factor in the regulation of the resting potential of cells, and this has been regarded as their major role in excitable and non-excitable tissues. On the other hand, the explanation for their ubiquitous presence and the impressive variability in their properties remains elusive. A reasonable hypothesis is that potassium channels are present in all cell types because they have in addition some "housekeeping" role, for example in cell proliferation[1]. Their implication in the regulation of the cell division cycle has been tested repeatedly, and some experimental evidence has been presented[2,3]. However, especially since both depolarization and hyperpolarization of the membrane potential during cell cycle have been reported as depending on cell type[1,4], there is no general model to explain the function of potassium channels in cell cycle. Two mechanisms have been proposed to explain the role of $K^+$ channels: they either influence the intracellular $Ca^{2+}$ concentration, or control cell volume (17, 18). Both mechanisms would indirectly influence cell proliferation. A member of the eag family has also been proposed to-be preferentially expressed in cancer cells (19) Several potassium channel blockers have been tested for their capability to block cancer cell proliferation, and some of them have even been used as coadjuvants for tumor chemotherapy, specially in multidrug-resistant tumors. Nevertheless, the lack of identification of a particular potassium channel directly involved in the control of cell proliferation has, up to date, precluded the description of more specific and effective treatment protocols.

Thus, the technical problem underlying the present invention was to identify a biological component within the conglomerate of potassium channels with their various effects on cell cycle division that allows an unambiguous assignment to cellular proliferation, with a specific view to human cellular proliferation. The solution to said technical problem is achieved by providing the embodiments characterized in the claims.

Accordingly, the present invention relates to a nucleic acid molecule comprising a nucleic acid molecule encoding a (poly)peptide having a function of the human $K^+$ ion eag channel which is
(a) a nucleic acid molecule comprising a nucleic acid molecule encoding the polypeptide having the amino acid sequence of SEQ ID: No 3 or 4;
(b) a nucleic acid molecule comprising the nucleic acid molecule having the DNA sequence of SEQ ID: No 13 or 14;
(c) a nucleic acid molecule hybridizing to the complementary strand of a nucleic acid molecule of (a) or (b); or
(d) a nucleic acid molecule being degenerate to the sequence of the nucleic acid molecule of (c).

The nucleic acid molecule of the invention encodes a (poly)peptide which is or comprises the human homologues of the rat eag channel. In this regard the term "a nucleic acid molecule comprising a nucleic acid molecule encoding a (poly)peptide having a function of the human $K^+$ ion eag channel" may mean that said first mentioned nucleic acid molecule solely encodes said (poly)peptide. Thus, it may be identical to said second mentioned nucleic acid molecule. Alternatively, it may comprise regulatory regions or other untranslated regions. In a further embodiment, said first mentioned nucleic acid may comprise heterologous nucleic acid which may encode heterologous proteinaceous material thus giving rise, e.g., to fusion proteins. It is further to be noted that the DNA sequences of SEQ ID NO: 13 and 14 are splice variants of the nucleic acid sequence encoding the (poly)peptide of the invention. The corresponding amino acid sequences are depicted in SEQ ID NO: 3 and 4.

The term "having a function of a human $K^+$ ion eag channel", as used in connection with the present invention, has the following meaning: The channel has a single channel conductance in asymmetrical potassium, at 0 mV of about 6 pS. This value clearly distinguishes the human channel from the rat channel for which a value of about 7 pS was measured. In addition or in the alternative, the above term may have the following meaning: The channel has a IC50 of about 1 mM to quinidine when expressed in *Xenopus laevis* oocytes, as compared to 400 µM for reag. Further, when measuring voltage-dependence of activation in high extracellular potassium using a two-electrode voltage-clamp it was found that in a conductance-voltage plot, the voltage for half-activation is shifted by about 40 mV or more to the right in the heag channel with respect to the reag channel (see FIG. 13). On the basis of the above features, either alone or in combination, a differentiation based on function between the human ion channel of the invention and the prior art channels, in particular of the rat ion channel, is possible for the person skilled in the art without further ado. Preferably, the channel has all recited functions. The above values refer to values that are obtainable with the experimental set-up described in this specification. Alterations of experimental parameters such as the employment of a different expression system may, as is well known to the person skilled in the art, also change the above values. Yet, these embodiments are also comprized by the scope of the present invention.

The term "hybridizing" as used in accordance with the present invention relates to stringent or non-stringent hybridization conditions. Preferably, it relates to stringent conditions. Said hybridization conditions may be established according to conventional protocols described, for example, in Sambrook, "Molecular Cloning, A Laboratory Manual", Cold Spring Harbor Laboratory (1989) N.Y., Ausubel, "Current Protocols in Molecular Biology", Green Publishing Associates and Wiley Interscience, N.Y. (1989), or Higgins and Hames (eds) "Nucleic acid hybridization, a practical approach" IRL Press Oxford, Washington D.C., (1985). Hybridizing molecules or molecules falling under alternative (d), supra, also comprise fragments of the molecules identified in (a) or (b) wherein the nucleotide sequence need not be identical to its counterpart in SEQ ID 13 or 14, said fragments having a function as indicated above.

An example of one such stringent hybridization condition is hybridization at 4×SSC at 65° C., followed by a washing in 0.1×SSC at 65° C. for one hour. Alternatively, an exemplary stringent hybridization condition is in 50% formamide, 4×SSC at 42° C. Examples of such non-stringent hybridization conditions are 4×SSC at 50° C. or hybridization with 30-40% formamide at 42° C. Complementary strands of hybridizing molecules comprise those which encode fragments, analogues or derivatives of the polypeptide of the invention and differ, for example, by way of amino acid and/or nucleotide deletion(s), insertion(s), substitution(s), addition(s) and/or recombination(s) or any other modification(s) known in the art either alone or in combination from the above-described amino acid sequences or their underlying nucleotide sequence(s). Using the PESTFIND program (Rogers, Science 234 (1986), 364-368), PEST sequences (rich in proline, glutamic acid, serine, and threonine) can be identified, which are characteristically present in unstable proteins. Such sequences may be removed from the polypeptide of the invention in order to increase the stability and optionally the activity of the proteins. Methods for introducing such modifications in the nucleic acid molecules according to the invention are well-known to the person skilled in the art. The invention also relates to nucleic acid molecules the sequence of which differs from the nucleotide sequence of any of the above-described nucleic acid molecules due to the degeneracy of the genetic code. All such fragments, analogues and derivatives encoding the protein of the invention are included within the scope of the present invention, as long as the essential characteristic immunological and/or biological properties as defined above remain unaffected in kind, that is the novel nucleic acid molecules of the invention include all nucleotide sequences encoding proteins or peptides which have at least a part of the primary structural conformation for one or more epitopes capable of reacting with antibodies to said polypeptide which are encoded by a nucleic acid molecule as set forth above and which have comparable or identical characteristics in terms of biological activity. Part of the invention is therefore also concerned with nucleic acid molecules encoding a polypeptide comprising at least a functional part of the above identified polypeptide encoded by a nucleic acid sequence comprised in a nucleic acid molecule according to the invention.

The present inventors have recently described a potassium channel (reag) which is strongly downregulated immediately after the activation of cyclin dependent kinases (key molecules in the cell cycle regulation), in both G1-S and G2-M transitions[5]. The K$^+$ current is inhibited following activation of cyclin-dependent kinases due to a voltage-dependent sodium block, which is not apparent in all phases of the cell cycle. The experiments presented here are aimed to determine whether eag, in addition to being regulated by the cell cycle, is also able to directly influence cell proliferation and growth (20). In accordance with the present invention and with a view to the development of a suitable system for assessing (disease-related) proliferation in human cells, it was further attempted to study whether the implication of the channel in the cell cycle goes in both directions, such that it is not only regulated by but also regulator of the progression of the cell cycle.

The results obtained in this rat derived ion channel system show that in three different cell lines obtained from different species (Chinese hamster —CHO—, human -HEK293-, and mouse -NIH3T3-), the rate of proliferation is faster when the channel is overexpressed after transfection of the cells with a plasmid containing the channel DNA under the control of the cytomegalovirus promoter. FIG. 1 and FIG. 18*a* show the increase in metabolic activity in cultures of CHO cells in the presence of normal concentrations of fetal calf serum (10% FCS). Under these normal conditions, reag transfected cells grow several folds faster than untransfected cells (WT).

Figure 2:
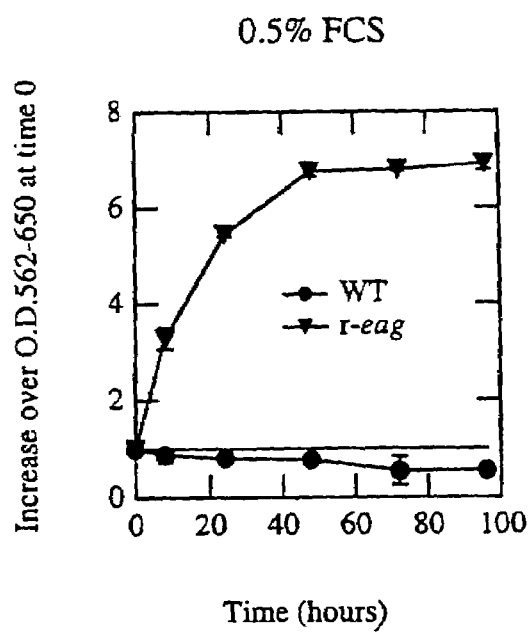

FIG. 2 shows a comparable experiment at very low concentrations of fetal calf serum (0.5% FCS). These low serum concentrations do not allow wild-type cells to grow; after a few hours, the cells start to die. However, reag transfected cells are able to proliferate under the same conditions. The ability to overcome the growth arrest induced by the absence of growth factors is one of the typical properties of malignant transformation (cf FIG. 18).

Figure 3:
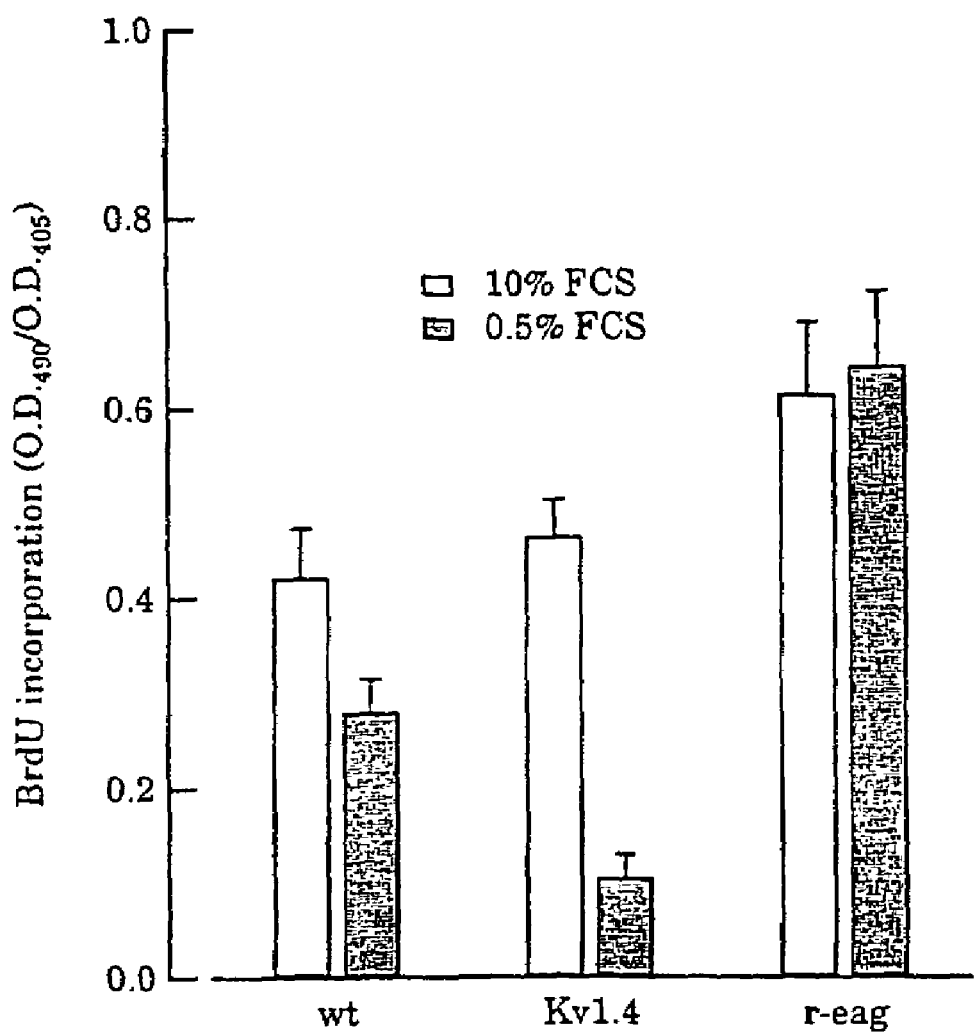

Not only the metabolic activity can be used to trace the proliferation in culture. The measurement of DNA synthesis is a more direct estimation of the rate of cell growth, since only cells entering S phase (committed to divide) synthesize DNA. Also DNA synthesis becomes serum-independent in reag transfected cells, i.e., the growth is maintained in the absence of growth factors (while it induces the programmed death of non-transfected cells). This is depicted in FIG. 3, were the incorporation of 5-Bromo-2'-deoxyuridine[7-10] (BrdU) was used to monitor DNA synthesis in the presence of 10 or 0.5% FCS in CHO cells. As opposed to wild-type or cells transfected with an inactivating voltage-dependent potassium channel from rat brain (Kv1.4), there are no significant differences in the amount of DNA synthesized in the presence of normal or low FCS concentrations in reag -expressing cells. Similar experiments were done using epidermal growth factor (EGF) in HEK-293 cells or platelet-derived growth factor (PDGF) in CHO cells, with essentially the same result. The pure growth factors were used to avoid the complexity introduced by the use of whole serum.

To test the effects of eag on cell proliferation more directly, DNA synthesis was measured through incorporation of 5-Bromo-deoxyuridine (BrdU) in cells synchronized in the S-phase of the cell cycle by means of thymidine arrest (23). Consistent with the above mentioned findings, when the S-phase of the cell cycle was allowed to proceed, reag expressing CHO cells (CHOrEAG) showed higher metabolic activity (FIG. 18B) and increased BrdU incorporation (FIG. 18C). These results suggest that more eag-transfected cells entered the S-phase during the arrested period and/or DNA synthesis was elevated, in any case indicating a faster proliferation rate in CHOrEAG cells. In the presence of low serum, BrdU incorporation was significantly higher in CHO-rEAG than in wild type cells (FIG. 18C).

Figure 4A:
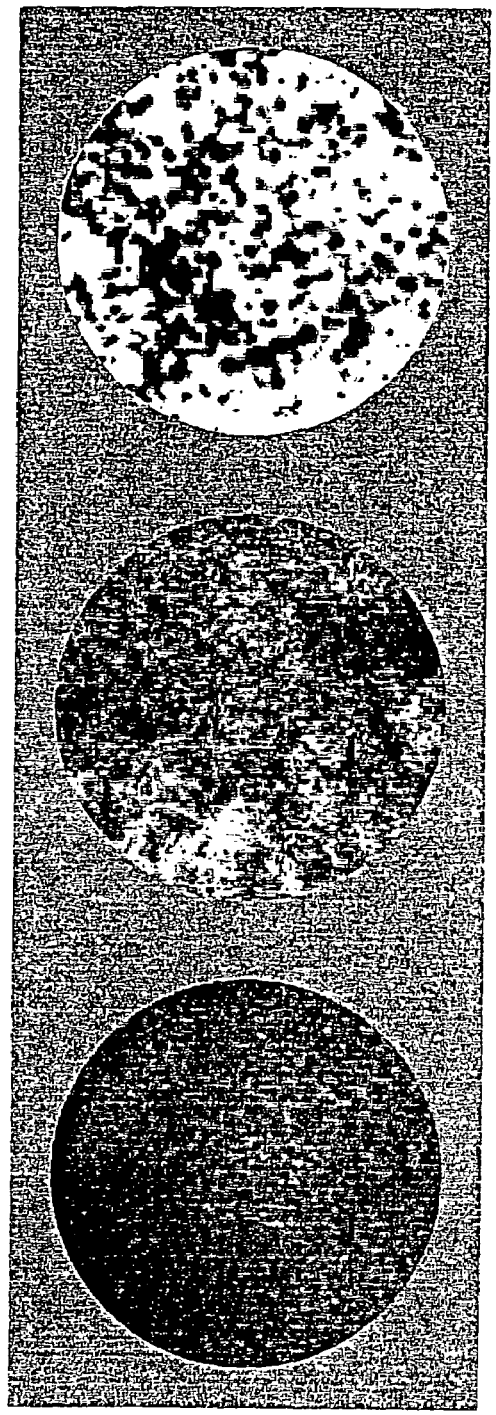

Yet another cell line, NIH3T3, has been frequently used for tumor transformation assays, since these cells are very strongly contact-inhibited, (i.e., their growth is stopped when the culture reaches confluency). This results in a homogeneous monolayer in wild-type cells. The malignant transformation of the line (through oncogene expression) usually induces the loss of this property, and NIH3T3 cells start forming colonies composed of several layers of cells. This can be seen after the transfection with reag DNA, which induced the formation of such foci in several independent clones (FIGS. 4A and B). Another standard test for transforming activity is the ability of NIH3T3 cells to grow in colonies when no substrate for attachment is available. To test this, cells are plated in an agar-containing medium, where the agar will prevent contacts between the cells and the surface of the plate. Under these conditions, wild-type NIH3T3 cells were unable to grow, while cells expressing reag formed large colonies even detectable by simple visual inspection of the plate. Table I shows that reag—(but not rKv1.4-) transfected cells formed colonies in a semisolid medium containing 0.3% agar (24, 25), regardless of the vector used for transfection (FIG. 14). All of the above results indicate a transforming potential of eag.

Altogether, the results obtained from transfected cells indicate that reag can, at least under certain conditions, display oncogenic properties.

Once the transforming ability of reag was determined in accordance with the invention, the expression of the respective channel in human cancer cells was investigated. For this investigation, the cell line MCF-7 was used, which was initially obtained from a pleural effusion of a breast adenocarcinoma. The line is estrogen receptor positive as well as estrogen-sensitive and relatively well differentiated. The strategy followed was first to test electrophysiologically and pharmacologically for the presence of a functional current similar to eag, and then to try an identification of the corresponding channel at the molecular level. However, conventional approaches for such an identification failed.

Figure 5:
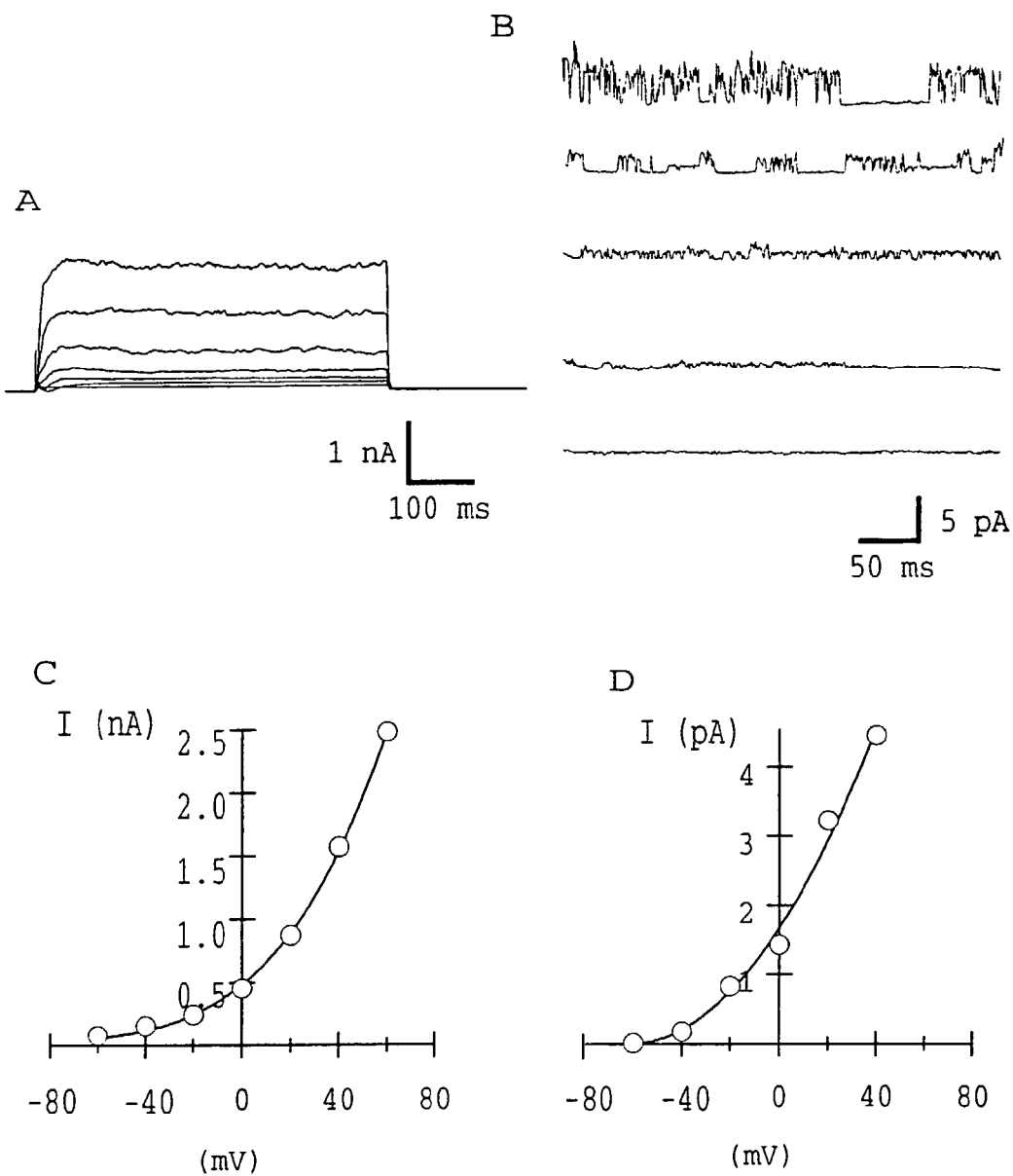

Namely, in most cells, the current density was too low to allow reliable measurements of the whole cell current. Low current density precluded an accurate measurement of channel properties using a whole cell configuration for the patch champ. Therefore, due to said low current densities encountered, another approach was resorted to. Due to such a low number of channels per cell, it is only possible to characterize the functional properties of a channel by a special patch champ method, excising patches of membranes containing one (or a few) channels and allowing characterization on a single molecule level. This approach relied on single-channel measurements in order to also compare properties at the single-molecule level such as single channel conductance, pharmacological properties, voltage dependence, and mean open times. Indeed, a channel with several properties compatible with reag in terms of kinetics, voltage-dependence, and pharmacology in most membrane patches could thus be identified. FIG. 5 shows whole-cell currents obtained from a MCF7 cell under nystatin patch conditions and single channel currents, together with their current-voltage relationship. Despite differences in kinetics at very depolarized voltages, the voltage dependence of the channel in human cells is highly reminiscent to the voltage-dependence of the reag channel. Moreover, the single channel properties of the putative human-eag are also very similar to those of reag.

Furthermore, standard approaches to isolate the said channel on a molecular level also were not successful. Several other groups have attempted and/or are still attempting to isolate the gene coding for a human eag without success and this in spite of the fact that the rat eag channel has already been published in 1994. For example, Warmke and Ganetzky (Proc. Natl. Acad. Sci. USA 91 (1994), 3428-3442) specifically set out to clone the human eag gene using conventional technology. They were, however, unsuccessful and cloned a novel, eag related gene which they termed h-erg (also referred to as HERG). Further, Wymore et al., Circulation Res. 80 (1997), 261-268, reported that no eag specific clones could be detected in a cDNA library from human heart in spite of the fact that primers for amplification were used that were conserved across the entire eag/erg superfamily. Thus, the standard approach with degenerated oligonucleotides based on the sequence of members of the family revealed itself unsuccessful, although HERG was systematically detected by other researchers in the field. Significantly, most of these approaches to clone the human eag gene were made with brain libraries. The conclusion from these combined prior art data was that the human eag gene could not be cloned by conventional technology using the most obvious source, namely brain tissue. The repeated isolation of HERG clones instead is most probably due to the relative abundance of HERG transcripts in brain libraries, and also to the high homology between the two channels. Consequently, a different strategy had to be devised to direct the screening more specifically to eag channels. First, as described herein above, a cell line expressing a channel functionally similar to reag was identified Then degenerated oligonucleotides based on conserved sequences between rat, bovine and mouse eag, but divergent from HERG were designed. Using these primers, the cDNA obtained from MCF7 cells by PCR was amplified, and a band of the expected size was cloned in a suitable vector and sequenced. The amplified fragment corresponded to approximately 400 bp within the core region of the channel protein, and shared 90% identity to the reag sequence at the DNA level, and 99% at the amino acid level. However, at this stage it was still quite unclear what the thus identified clone corresponded to. For example, it was quite possible that a further member of the eag family had been identified. This is in particular true in view of the fact that despite of a number of attempts with brain libraries, nobody had been able to clone the human eag gene and that the MCF7 line is a breast cancer derived line.

Since MCF7 cells are immortal cells, it is assumed that a number of genes is mutated. Ab initio, it could have been expected that the human eag channel, if at all expressed in this cell line, was mutated. Under this assumption, it was quite uncertain whether this cell line could at all be used for the isolation of the desired gene.

Figure 10:
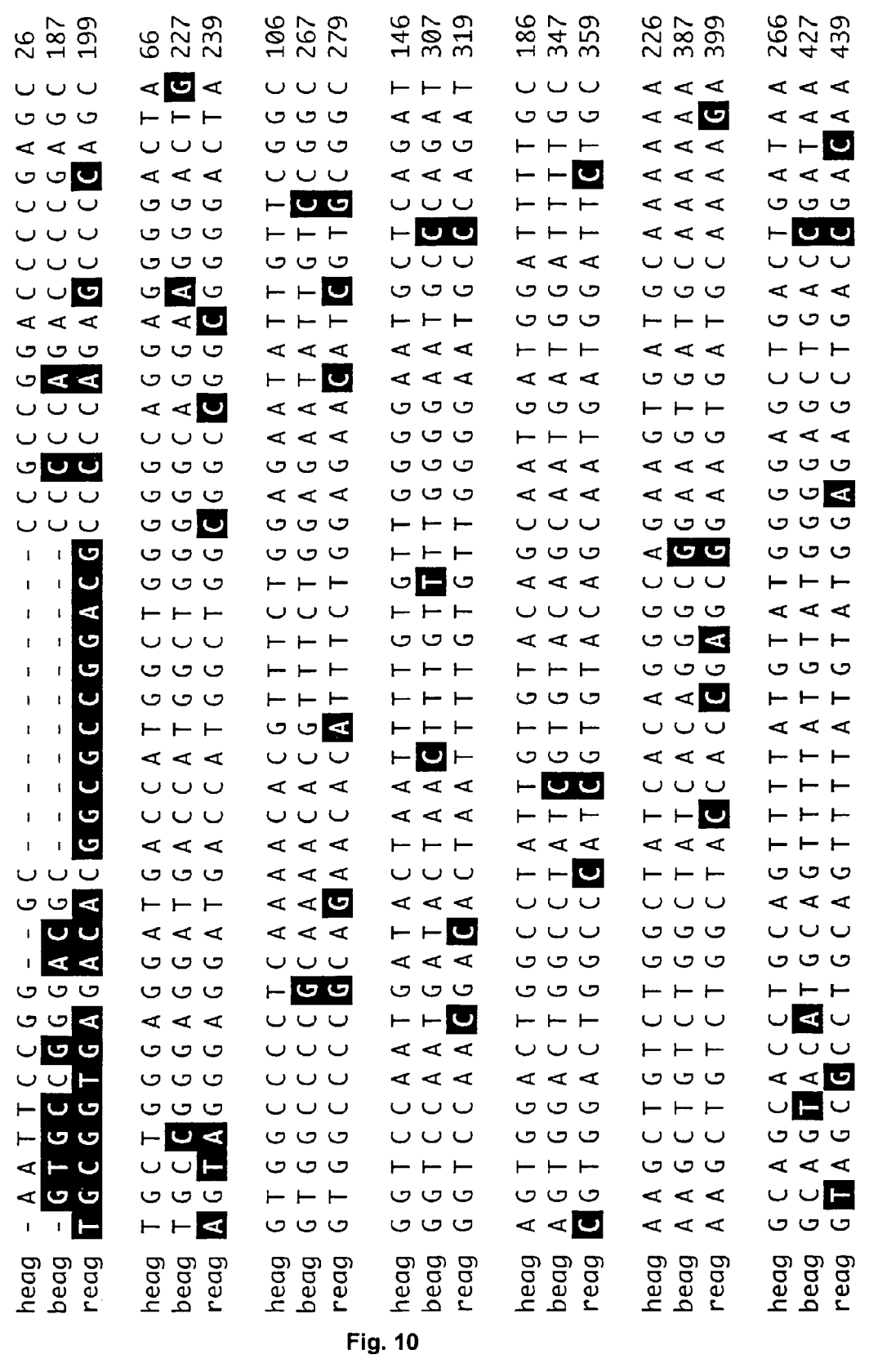
Figure 10:
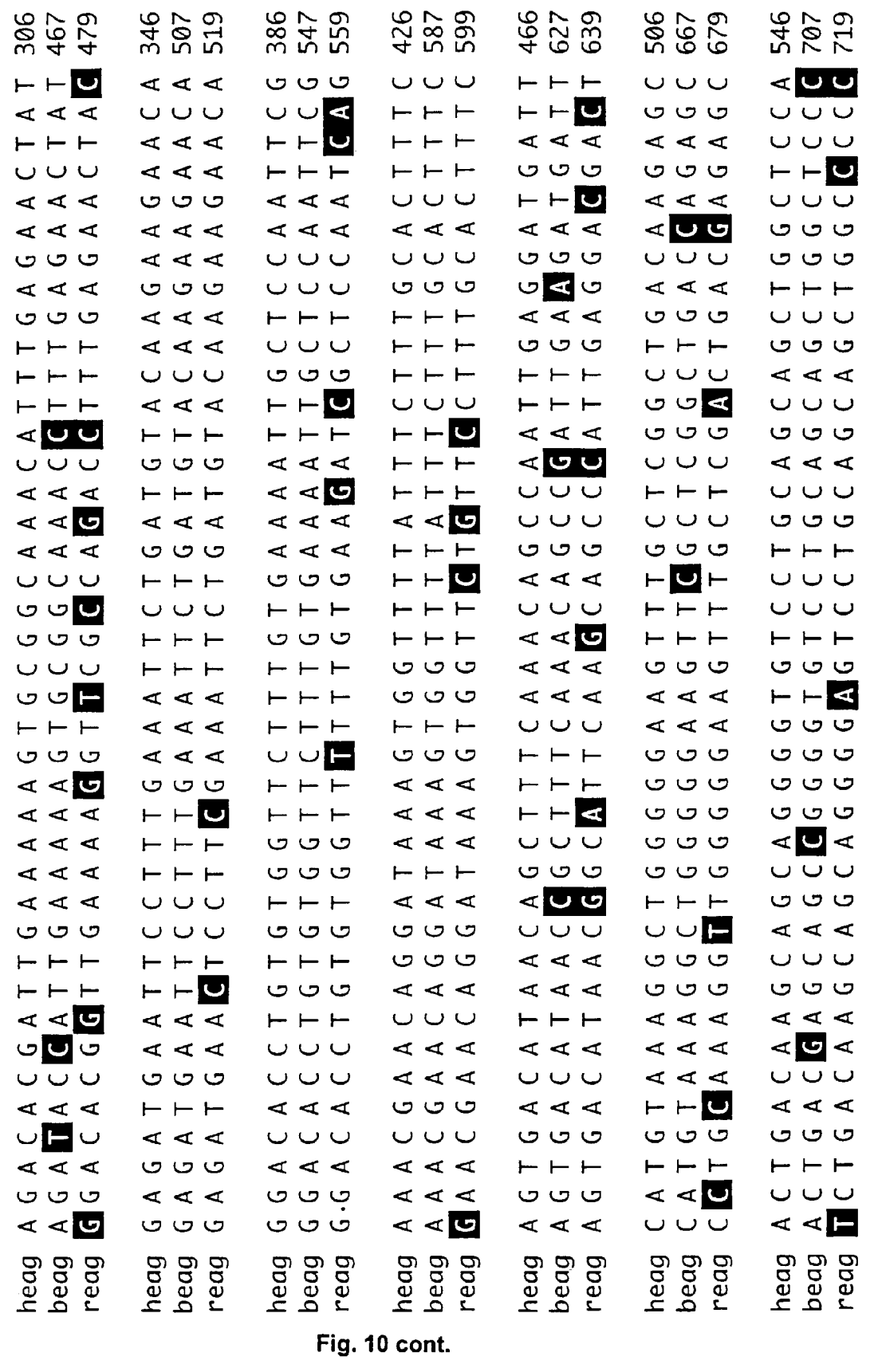
Figure 10:
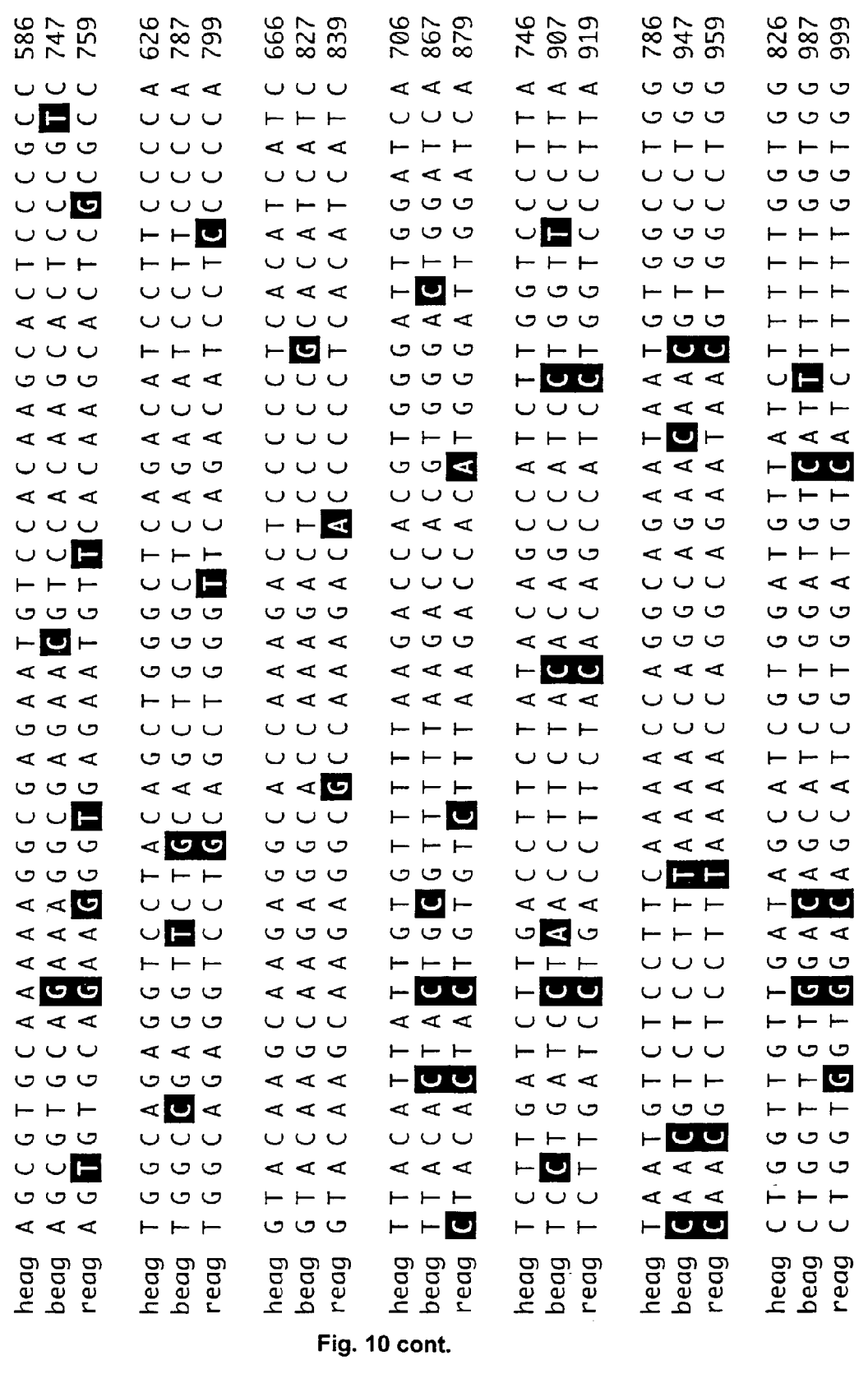
Figure 10:
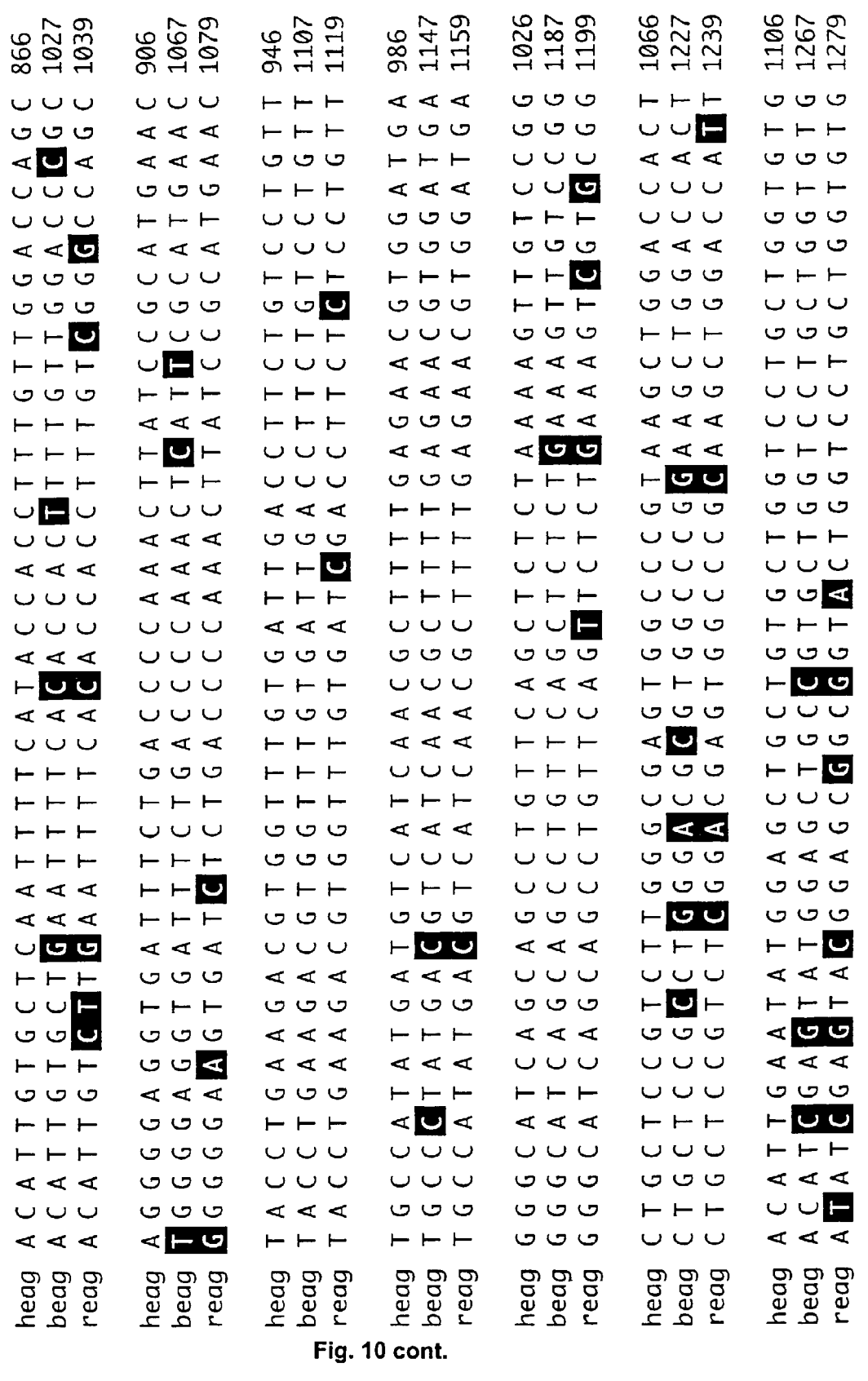
Figure 10:
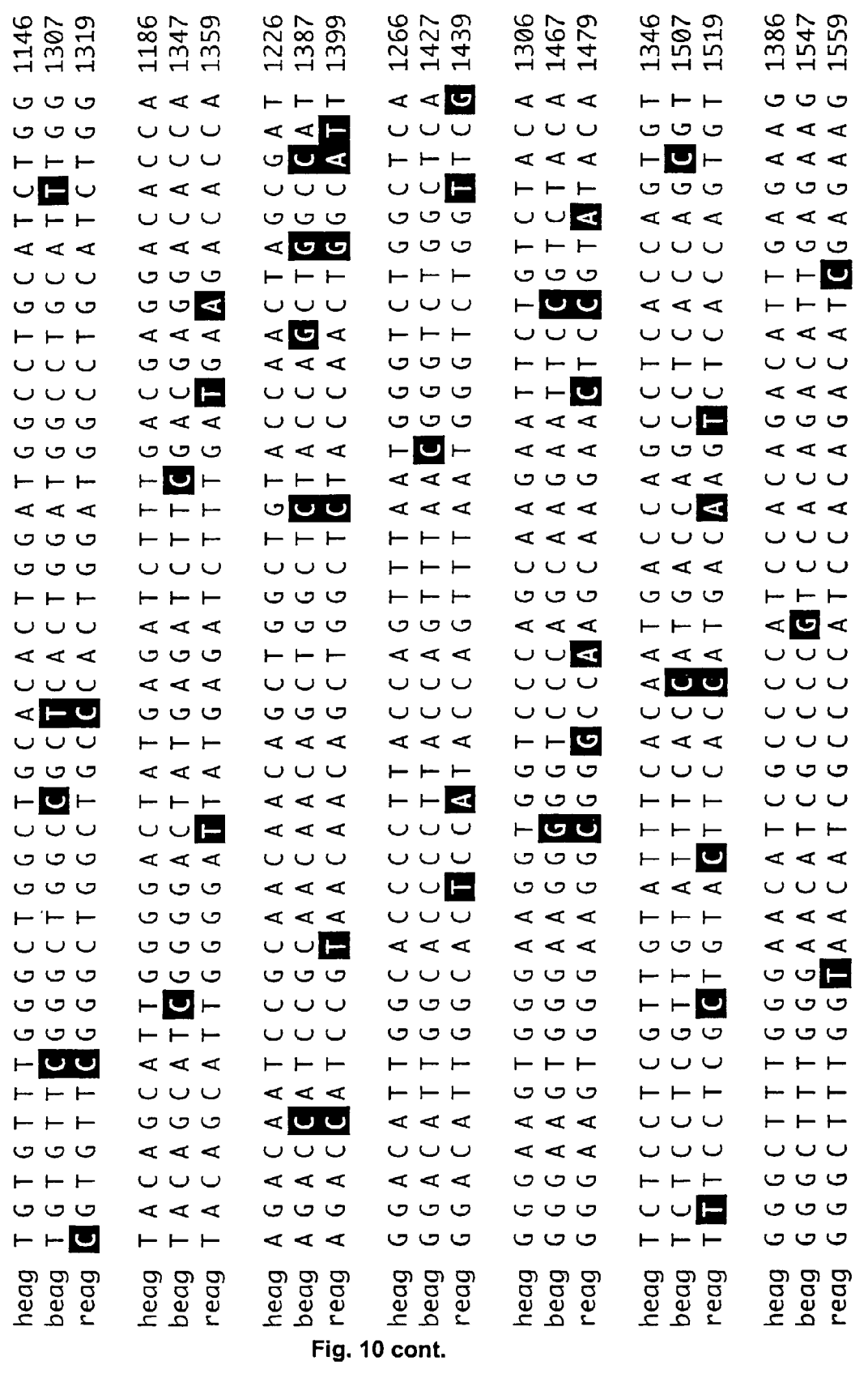
Figure 10:
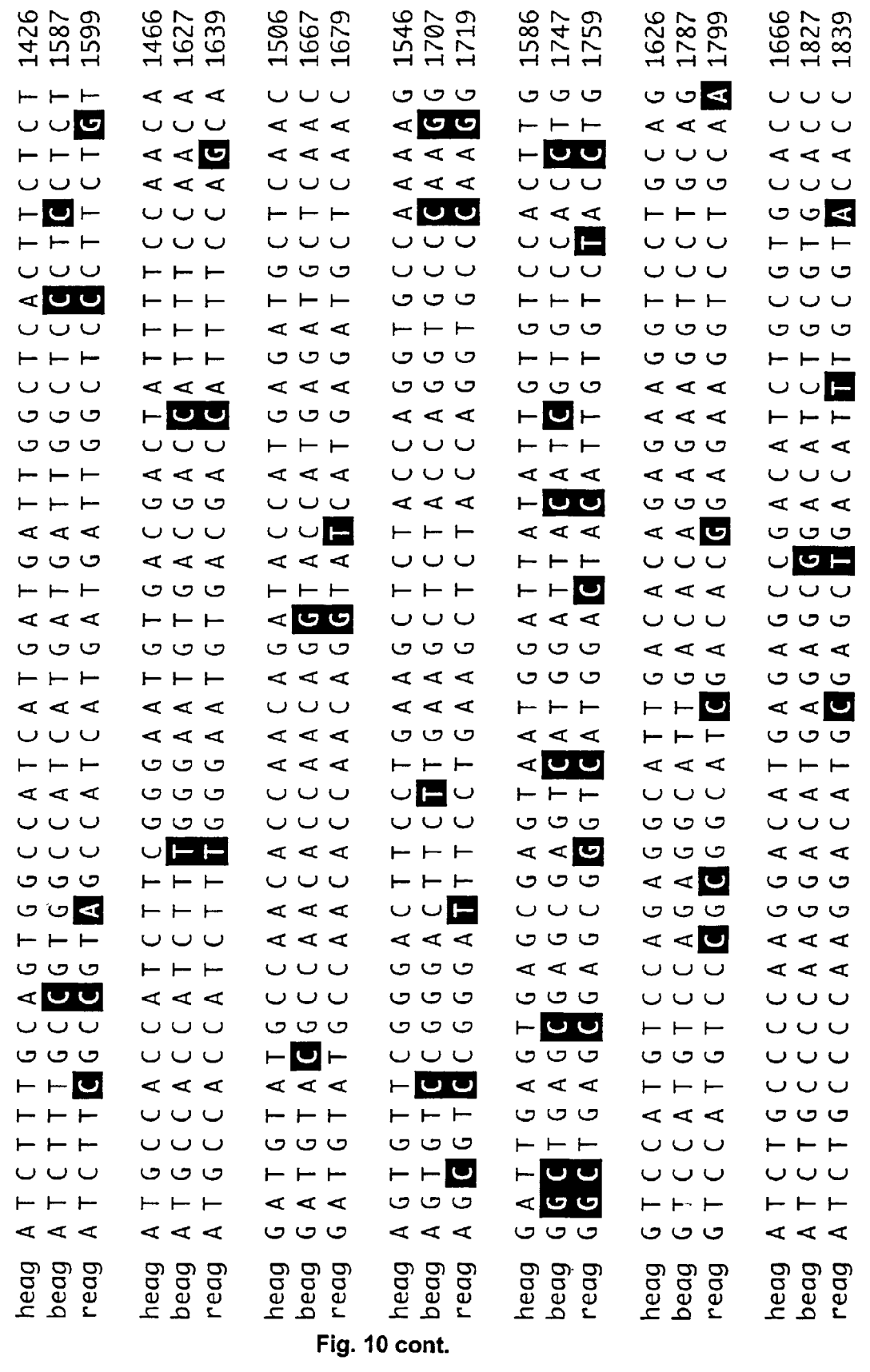
Figure 10:
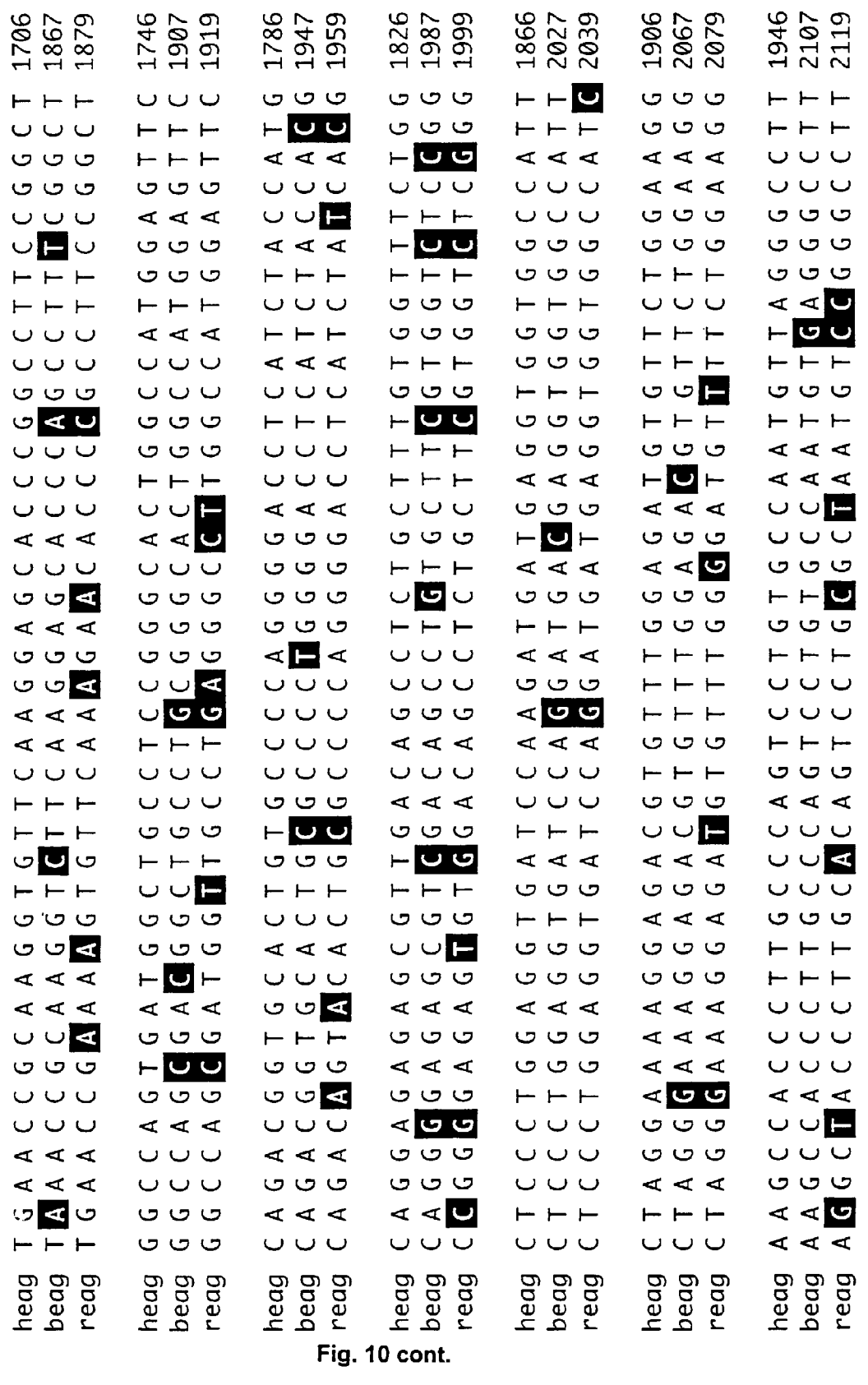
Figure 10:
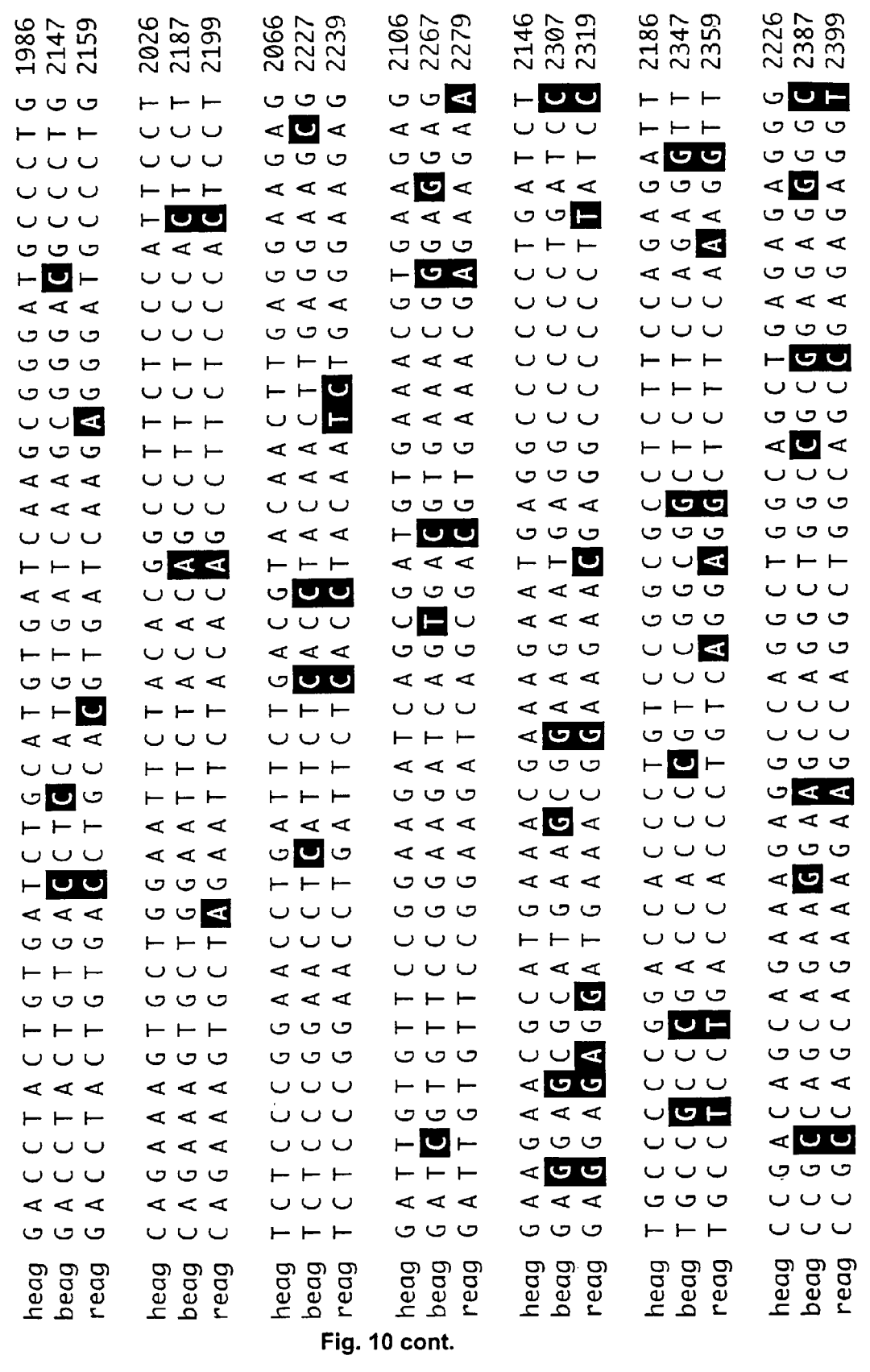
Figure 10:
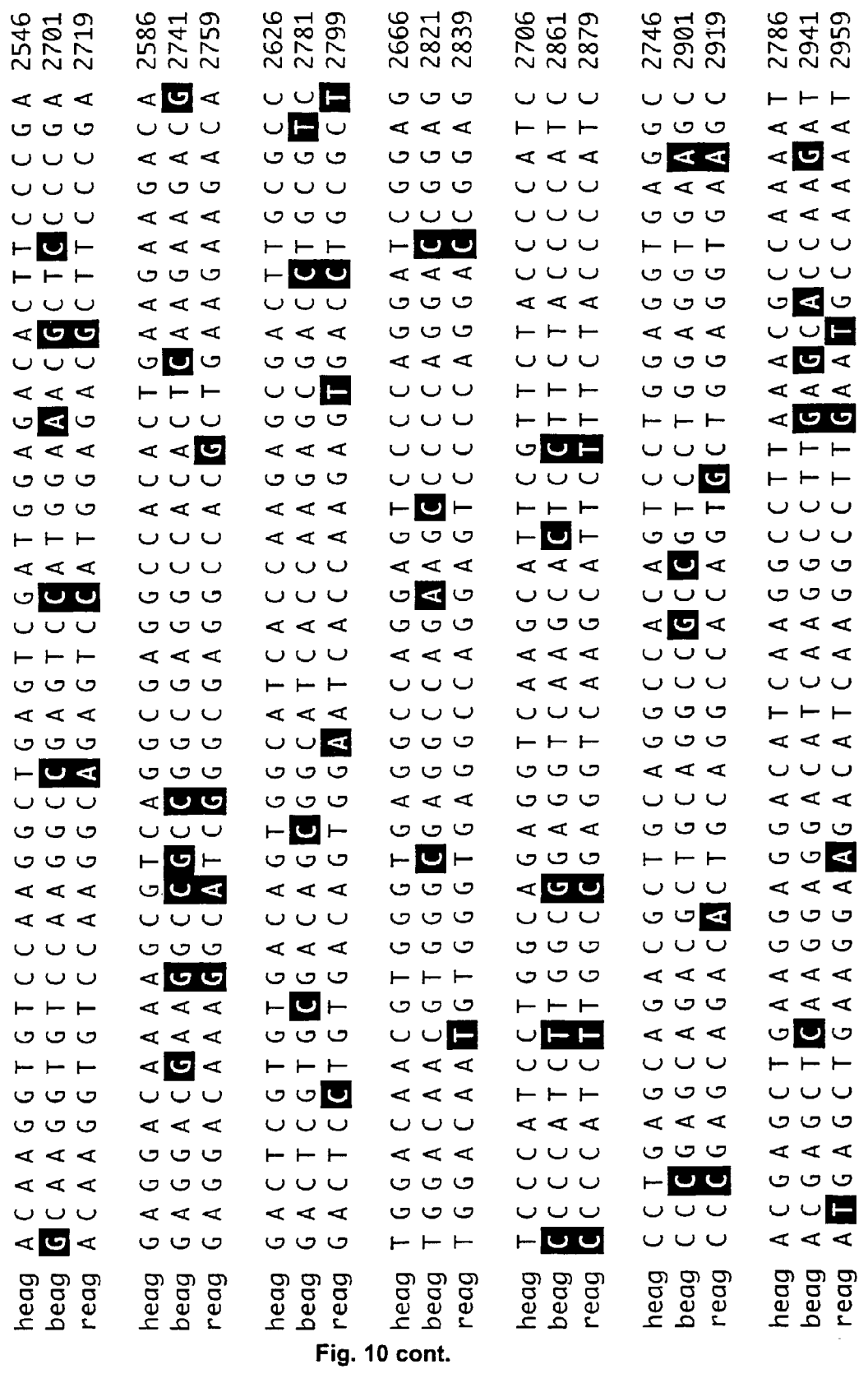
Figure 10:
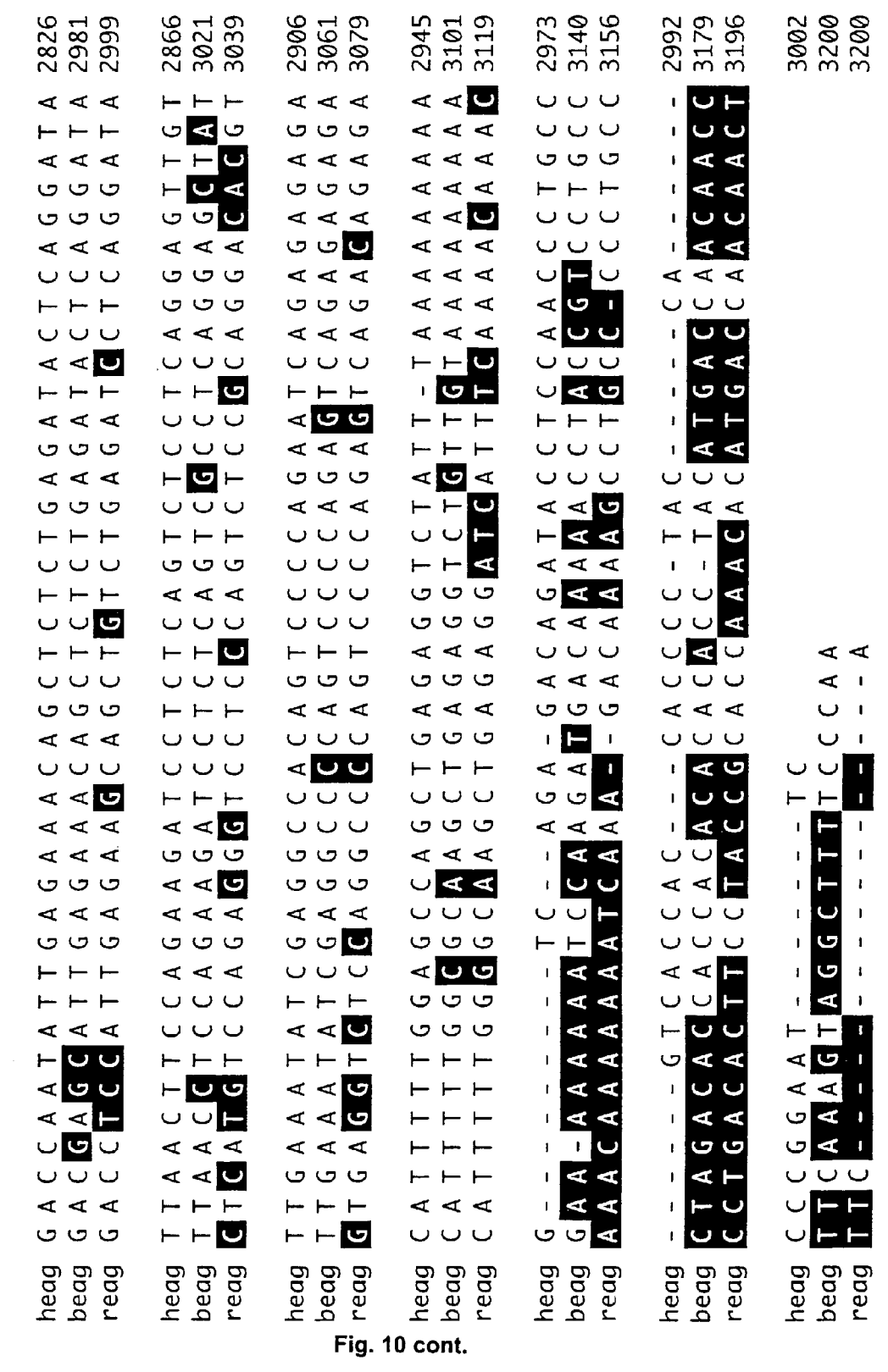

Due to the prior art failures to clone human eag gene from brain libraries and the above recited uncertainties with immortalized cell lines, another source for a library was in need. The 400 bp fragment was therefore used to screen a normal human breast cDNA library. Due to the presence of eag is breast cancer cells, such a library was expected to comprise heag clones. Surprisingly, however, after screening $2 \times 10^6$ phages, no human-eag clones could be identified in said library. This rises the possibility that the channel is expressed only in tumor cells, and not in normal tissue. Specific oligonucleotides, namely 5'-CCAAACACACA-CACCAGC (SEQ ID NO: 5) and 5'-CGTGGATGT-TATCTTTTTGG (SEQ ID NO: 6), were designed to check for heag fragments by PCR amplification directly from the above library, but no evidence for the presence of any eag clones in this library was found. In view of the above discussed prior art results, it came as a further surprise that the same primers detected heag in a normal human brain cDNA library, that was therefore screened. First, the probe obtained from MCF7 cells was used to check $10^6$ phages. This procedure allowed to isolate a 1.6 kbp fragment from human eag. This fragment was then used as a probe for the screening of $2 \times 10^6$ phages from the same library. Several independent clones were isolated, but none of them was a full-length clone. Furthermore, only one clone contained the 5' end of the sequence, while two of them contained the 3' end and part of the 3' non-coding region. It is likely that the abundance of restriction sites in the nucleic acid sequence encoding the channel has induced this extensive fragmentation of the cDNA. For example, when EcoRI was used to extract the inserts of the library that was cloned in λ-gt10 phage at the EcoRI site, this conventional approach systematically failed to find the 5' end of the molecule (there is an EcoRI site at position 400 of the clone). The pooled positive clones were therefore screened again by PCR, trying to amplify the start codon, and only by this means was it possible to isolate one phage that contained this ATG. Two splice variants of heag were cloned, both expressed in brain tissue. The sequences obtained for heag 1 and heag 2 and their deduced amino acid sequences are shown in FIGS. 10 and 11, and compared to other members of the family.

The deduced amino acid sequence is identical to the sequence published after the priority date of the present invention by Occhidoro (27) and is 97.7% identical to reag. As mentioned, a second (81 bp longer) splice variant (heag 2) was also isolated analogous to that reported for bovine and mouse eag channels (28), the splice insertion being identical in all three species. The chromosomal localization of heag was determined by FISH detection (29) to map to chromosome lq32.1-32.3 (see also ref. 26).

To further check the possibility that heag is not expressed in normal mammary gland, as opposed to MCF-7 cancer cells, we performed single-tube RT-PCR experiments using total RNA from human brain, human mammary gland, and MCF-7 cells (FIG. 12), using as primers two oligonucleotides designed to discriminate between the two splice variants of heag. In human brain, two splice variants were detected, while only the short one was expressed in MCF-7 cells (this, together with the lack of amplification in the absence of reverse transcriptase, rules out a possible contamination by genomic DNA of the RNA preparation). No heag signal was detected in normal mammary gland RNA with this highly sensitive technique. This result was totally unexpected, because preliminary results had suggested that expression was present in tumor cells from the same organ. Further, after Southern blot analysis of the RT-PCR products a faint band hybridizing with a heag probe in mammary gland was identified. Accordingly, it is quite difficult to make a strong statement on the total absence of heag message in breast in view of these contradictory experimental data.

Furthermore, electrophyiological properties (21, 30) of heag were tested in *Xenopus oocytes*. As described above, they did not differ significantly from those or reag with the above mentioned exceptions, e.g. a shift in activation of 40 mV to more depolarized potentials when both channels were measured under identical conditions. The electrophysiological observations of heag channels expressed in *Xenopus oocytes* correlate well to hose reported by Bijlenga et al. (31).

The present invention also relates to a nucleic acid molecule specifically hybridizing to the nucleic acid molecule of the invention which comprises the sequence 5'-GG-GAGGATGACCACATGGCT (SEQ ID NO: 7).

This embodiment of the present invention is particularly useful for specific antisense therapies for inhibiting cell proliferation as will be discussed in more detail herein below (e.g. in Example 5). In addition, this embodiment of the nucleic acid molecule of the invention can, naturally, also be used as a probe for specifically detecting heag mRNA in tissues, for example, by employing the Northern Blot technology. The analysis of heag mRNA expression in various tissues by Northern blot revealed a strong hybridization signal of approximately 9.2 kb in brain and a weak signal of similar size in placenta. Heart, lung, liver, skeletal muscle, kidney and pancreas were negative even following long exposures. In addition, total RNA from human brain, heart, trachea, adrenal gland, liver, kidney, skeletal muscle and mammary gland, and spinal cord poly(A)$^+$ RNA, as well as total RNA from the adenovirus-transformed line 293 (a human non-tumoral cell line) were assayed by single-tube RT-PCR and Southern blot. Under these experimental conditions, heag was detected in brain only, where both splice variants were identified (FIG. 15; Example 3).

The preferential expression of heag in brain was intriguing since the first cDNA had been isolated from an epithelial tumor cell line (MCF-7) and not from brain tissue (see above). To elucidate the presence of heag in other tumoral cell lines, total RNA was prepared from HeLa (cervix carcinoma), SHSY-5Y (neuroblastoma), and lines from mammary gland tumors: COLO-824 (carcinoma), EFM-19 (carcinoma), and BT-474 (ductal carcinoma). Total RNA from brain, MCF-7 cells, 293 cells and RNA from cultures of mammary gland epithelial cells (included to circumvent the mixed cell populations in whole mammary gland) served as controls. All cell lines were obtained from DSMZ (Deutsche Sammlung von Mikroorganismen und Zellkulturen) and maintained following the DSMZ catalog guidelines. Normal human mammary epithelial cells were purchased from BioWhittaker. The primers were designed to amplify different bands for heag 1 and heag 2, thus allowing us to rule out false positives due to genomic DNA contamination (controls in the absence of reverse transcriptase were also performed). HeLa, SHSY-5Y, EFM-19 and MCF-7 RNA exhibited an heag band, whereas COLO-824 and BT-474 signals were indistinguishable from background (FIG. 15B). Cultured epithelial cells and 293 cells (FIG. 15A) were negative. As discussed above, it could be shown in accordance with the present invention that reag transfected cells can display oncogenic properties. Thus, to determine whether the expression of heag is advantageous for tumor cells in vivo, subcutaneous implants of CHO cells expressing the channel (CHOhEAG cells) into the flank of female scid (severe combined immunodeficiency, 32) mice were performed and it could be shown that expression of heag represents an advantage for the proliferation of tumor cells in vivo, since CHOhEAG tumors grow faster and are more aggressive than CHOKv tumors. Thus, the embodiment of the nucleic acid molecule of the present invention may be employed in the quantitative and qualitative analysis of the expression level of human eag in various disease states detectable in a tissue that may be indicative of, for example, cancer (in particular mamma carcinoma, neuroblastoma), psoriasis, neurodegenerative diseases such as Alzheimer's disease, Parkinson's disease, lateral amyotrophic sclerosis or multiple sclerosis.

In a preferred embodiment of the nucleic acid molecule of the invention, said nucleic acid molecule is DNA, such as genomic DNA. Whereas the present invention also comprises synthetic or semi-synthetic DNA molecules or derivatives thereof, such as peptide nucleic acid, the most preferred DNA molecule of the invention is cDNA.

In a further preferred embodiment of the present invention, said nucleic acid molecule is RNA, preferably mRNA.

Another preferred embodiment of the nucleic acid molecule of the invention encodes a fusion protein. For example, the nucleic acid molecule of the invention can be fused in frame to a detectable marker such as FLAG or GFP.

The invention further relates to a vector, particularly plasmid, cosmids, viruses and bacteriophages comprising the nucleic acid molecule of the invention. Such vectors may comprise further genes such as marker genes which allow for the selection of said vector in a suitable host cell and under suitable conditions. Thus the polynucleotide of the invention can be operatively linked in said vector to expression control sequences allowing expression in prokaryotic or eukaryotic cells. Expression of said polynucleotide comprises transcription of the polynucleotide into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers. Possible regulatory elements permitting expression in prokaryotic host cells comprise, e.g., the lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pCDM8, pRc/CMV, pcDNA1, pcDNA3 (In-vitrogene), pSPORT1 (GIBCO BRL).

Preferably, said vector is an expression vector and/or a gene transfer or targeting vector. Expression vectors and gene targeting or transfer vectors are well-known in the art and can be adapted for specific purposes of the invention by the person skilled in the art. Thus, expression vectors derived from viruses such as retroviruses, vaccinia virus, adeno-associated virus, herpes viruses, or bovine papilloma virus, may be used for delivery of the polynucleotides or vectors of the invention into targeted cell populations. Methods which are well known to those skilled in the art can be used to construct recombinant viral vectors; see, for example, the techniques described in Sambrook, Molecular Cloning, A Laboratory Manual, Cold Spring Harbor Laboratory (1989) N.Y. and Ausubel, Current Protocols in Molecular Biology, Green Publishing Associates and Wiley Interscience, N.Y. (1989). Alternatively, the polynucleotides and vectors of the invention can be reconstituted into liposomes for delivery to target cells.

The invention furthermore relates to a host transformed with the vector of the invention. Said host may be a prokaryotic or eukaryotic cell; see supra. The polynucleotide or vector of the invention which is present in the host cell may either be integrated into the genome of the host cell or it may be maintained extrachromosomally. In this respect, it is also to be understood that the recombinant DNA molecule of the invention can be used for "gene targeting" and/or "gene replacement", for restoring a mutant gene or for creating a mutant gene via homologous recombination; see for example Mouellic, Proc. Natl. Acad. Sci. USA, 87 (1990), 4712-4716; Joyner, Gene Targeting, A Practical Approach, Oxford University Press. Preferably, the host is a mammalian cell, a fungal cell, a plant cell, an insect cell or a bacterial cell. Preferred fungal cells are, for example, those of the genus *Saccharomyces*, in particular those of the species *S. cerevisiae*. The term "prokaryotic" is meant to include all bacteria which can be transformed or transfected with a polynucleotide for the expression of the protein of the present invention. Prokaryotic hosts may include gram negative as well as gram positive bacteria such as, for example, *E. coli, S. typhimurium, Serratia marcescens* and *Bacillus subtilis*. Methods for preparing fused, operably linked genes and expressing them in bacteria or animal cells are well-known in the art (Maniatis, et al., Molecular Cloning: A Laboratory Manual, Cold Spring Harbor Laboratory, Cold Spring Harbor, N.Y., 1989). The genetic constructs and methods described therein can be utilized for expression the protein of the present invention in prokaryotic hosts. In general, expression vectors containing promoter sequences which facilitate the efficient transcription of the inserted polynucleotide are used in connection with the host. The expression vector typically contains an origin of replication, a promoter, and a terminator, as well as specific genes which are capable of providing phenotypic selection of the transformed cells. The transformed prokaryotic hosts can be grown in fermentors and cultured according to techniques known in the art to achieve optimal cell growth. The polypeptides of the invention can then be isolated from the grown medium, cellular lysates, or cellular membrane fractions. The isolation and purification of the microbially or otherwise expressed polypeptides of the invention may be by any conventional means such as, for example, preparative chromatographic separations and immunological separations such as those involving the use of monoclonal or polyclonal antibodies. As regards mammalian cells, HEK 293, CHO, HeLa and NIH 3T3 are preferred. As regards insect cells, it is most preferred to use *Spodoptera frugiperda* cells, whereas the most preferred bacterial cells are *E.coli* cells.

The invention also relates to a method of producing the (poly)peptide encoded by the nucleic acid molecule of the invention comprising culturing the host of the invention and isolating the produced (poly)peptide.

Depending on the vector constructing employed, the (poly)peptide of the invention may be exported to the culture medium or maintained within the host. Suitable protocols for obtaining the (poly)peptide produced are well-known in the art for both ways of (poly)peptide production.

The present invention furthermore relates to a (poly)peptide encoded by the nucleic acid molecule of the invention or produced by the method of the invention. The new channel is envisaged to show a structure having a short amino-terminal region, probably intracellular, five membrane-spanning segments, a hydrophobic hairpin entering the membrane, a sixth transmembrane segment, and a long C-terminal cytoplasmic part comprising a cyclic-nucleotide binding consensus sequence, a nuclear localization consensus sequence, and a hydrophobic domain probably forming a coiled-coil structure. The polypeptide of the invention may also be a functional fragment of the human $K^+$ ion channel. By "functional fragment" polypeptides are meant that exhibit any of the activity of heag as described above. Using recombinant DNA technology, fragments of the (poly)peptide of the invention can be produced. These fragments can be tested for the desired function, for example, as indicated above, using a variety of assay systems such as those described in the present invention. Preferably, said fragments comprise the C-terminal portion of the novel ion channel.

The present invention also relates to an antibody specifically directed to the (poly)peptide of the invention. The antibody of the invention specifically discriminates between the human eag channel and the prior art channels such as mouse and rat eag and preferably binds to epitopes in the C-terminal part of the ion channel. The term "antibody", as used in accordance with the invention, also relates to antibody fragments or derivatives such as $F(ab)_2$, Fab', Fv or scFv fragments; see, for example, Harlow and Lane, "Antibodies, A Laboratory Manual", CSH Press 1988, Cold Spring Harbor, N.Y. Preferably, the antibody of the invention is a monoclonal antibody.

The invention also relates to a pharmaceutical composition comprising the nucleic acid molecule of the invention, the vector of the invention, the polypeptide of the invention and/or the antibody of the invention and a pharmaceutically acceptable carrier and/or diluent and/or excipient.

Examples of suitable pharmaceutical carriers and diluents as well as of excipients are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the patient in need thereof at a suitable dose. Administration of the suitable compositions may be effected by different ways, e.g., by oral, intravenous, intraperitoneal, subcutaneous, intramuscular, topical or intradermal administration. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently. Generally, the regimen as a regular administration of the pharmaceutical composition should be in the range of 1 μg to 10 mg units per day. If the regimen is a continuous infusion, it should also be in the range of 1 μg to 10 mg units per kilogram of body weight per minute, respectively. Progress can be monitored by periodic assessment. Dosages will vary but a preferred dosage for intravenous administration of DNA is from approximately $10^6$ to $10^{12}$ copies of the DNA molecule. The compositions of the invention may be administered locally or systemically. Administration will generally be parenterally, e.g., intravenously; DNA may also be administered directly to the target site, e.g., by biolistic delivery to an internal or external target site or by catheter to a site in an artery.

It is envisaged by the present invention that the various polynucleotides and vectors of the invention are administered either alone or in any combination using standard vectors and/or gene delivery systems, and optionally together with a pharmaceutically acceptable carrier or excipient. Subsequent to administration, said polynucleotides or vectors may be stably integrated into the genome of the subject. On the other hand, viral vectors may be used which are specific for certain cells or tissues and persist in said cells or tissues. Suitable pharmaceutical carriers and excipients are, as has been stated above, well known in the art. The pharmaceutical compositions prepared according to the invention can be used for the prevention or treatment or delaying of different kinds of diseases, which are related to the undesired (over)expression of the above identified nucleic acid molecule of the invention. In a preferred embodiment the pharmaceutical composition comprises antisense oligodesoxynucleotides, as for example described in example 5, capable of regulating, preferably decreasing heavy expression.

Furthermore, it is possible to use a pharmaceutical composition of the invention which comprises the polynucleotide or vector of the invention in gene therapy. Suitable gene delivery systems may include liposomes, receptor-mediated delivery systems, naked DNA, and viral vectors such as herpes viruses, retroviruses, adenoviruses, and adeno-associated viruses, among others. Gene therapy, which is based on introducing therapeutic genes, for example for vaccination into cells by ex-vivo or in-vivo techniques is one of the most important applications of gene transfer. Suitable vectors, methods or gene-delivery systems for in-vitro or in-vivo gene therapy are described in the literature and are known to the person skilled in the art; see, e.g., Giordano, Nature Medicine 2 (1996), 534-539; Schaper, Circ. Res. 79 81996), 911-919; Anderson, Science 256 (1992), 808-813; Isner, Lancet 348 (1996), 370-374; Muhlhauser, Circ. Res. 77 (1995), 1077-1086; Onodera, Blood 91 (1998), 30-36; Verzeletti, Hum. Gene Ther. 9 (1998), 2243-2251; Verma, Nature 389 (1997), 239-242; Anderson, Nature 392 (Supp. 1998), 25-30; Wang, Gene Therapy 4 (1997), 393-400; Wang, Nature Medicine 2 (1996), 714-716; WO 94/29469; WO 97/00957; U.S. Pat. Nos. 5,580,859; 5,589,466; 4,394,448 or Schaper, Current Opinion in Biotechnology 7 (1996), 635-640, and references cited therein. The nucleic acid molecules and vectors of the invention may be designed for direct introduction or for introduction via liposomes, or viral vectors (e.g. adenoviral, retroviral) into the cell. Additionally, a baculoviral system can be used as eukaryotic expression system for the nucleic acid molecules of the invention. Delivery of nucleic acids to a specific site in the body for gene therapy may also be accomplished using a biolistic delivery system, such as that described by Williams (Proc. Natl. Acad. Sci. USA 88 (1991), 2726-2729).

Standard methods for transfecting cells with recombinant DNA are well known to those skilled in the art of molecular biology, see, e.g., WO 94/29469. Gene therapy may be carried out by directly administering the recombinant DNA molecule or vector of the invention to a patient or by transfecting cells with the polynucleotide or vector of the invention ex vivo and infusing the transfected cells into the patient. Furthermore, research pertaining to gene transfer into cells of the germ line is one of the fastest growing fields in reproductive biology. Gene therapy, which is based on introducing therapeutic genes into cells by ex vivo or in vivo techniques is one of the most important applications of gene transfer. Suitable vectors and methods for in vitro or in vivo gene therapy are described in the literature and are known to the person skilled in the art; see, e.g., WO 94/29469, WO 97/00957 or Schaper (Current Opinion in Biotechnology 7 (1996), 635-640) and references cited above. The polynucleotides and vectors comprised in the pharmaceutical composition of the invention may be designed for direct introduction or for introduction via liposomes, or viral vectors (e.g. adenoviral, retroviral) containing said recombinant DNA molecule into the cell. Preferably, said cell is a germ line cell, embryonic cell, stem cell or egg cell or derived therefrom. An embryonic cell can be for example an embryonic stem cell as described in, e.g., Nagy, Proc. Natl. Acad. Sci. USA 90 (1993) 8424-8428.

It is to be understood that the introduced polynucleotides and vectors of the invention express the (poly)peptide of the invention after introduction into said cell and preferably remain in this status during the lifetime of said cell. For example, cell lines which stably express the polynucleotide under the control of appropriate regulatory sequences may be engineered according to methods well known to those skilled in the art. Rather than using expression vectors which contain viral origins of replication, host cells can be transformed with the polynucleotide or vector of the invention and a selectable marker, either on the same or separate vectors. Following the introduction of foreign DNA, engineered cells may be allowed to grow for 1-2 days in an enriched media, and then are switched to a selective medium. The selectable marker in the recombinant plasmid confers resistance to the selection and allows for the selection of cells having stably integrated the plasmid into their chromosomes and grow to form foci which in turn can be cloned and expanded into cell lines. Such engineered cell lines are particularly useful in screening methods or methods for identifying an inhibitor of the polypeptide of the present invention as described below.

A number of selection systems may be used, including but not limited to the herpes simplex virus thymidine kinase (Wigler, Cell 11(1977), 223), hypoxanthine-guanine phosphoribosyltransferase (Szybalska, Proc. Natl. Acad. Sci. USA 48 (1962), 2026), and adenine phosphoribosyltransferase (Lowy, Cell 22 (1980), 817) in tk, hgprt or aprt cells, respectively. Also, antimetabolite resistance can be used as the basis of selection for dhfr, which confers resistance to methotrexate (Wigler, Proc. Nati. Acad. Sci. USA 77 (1980), 3567; O'Hare, Proc. Natl. Acad. Sci. USA 78 (1981), 1527), gpt, which confers resistance to mycophenolic acid (Mulligan, Proc. Natl. Acad. Sci. USA 78 (1981), 2072), neo, which confers resistance to the aminoglycoside G-418 (Colberre-Garapin, J. Mol. Biol. 150 (1981), 1), hygro, which confers resistance to hygromycin (Santerre, Gene 30 (1984), 147), Shble, which confers resistance to Zeocin® (Mulsant, Somat. Cell. Mol. Genet. 14 (1988), 243-252 or puromycin (pat, puromycin N-acetyl transferase). Additional selectable genes have been described, for example, trpB, which allows cells to utilize indole in place of tryptophan; hisD, which allows cells to utilize histinol in place of histidine (Hartman, Proc. Natl. Acad. Sci. USA 85 (1988), 8047); and ODC (ornithine decarboxylase) which confers resistance to the ornithine decarboxylase inhibitor, 2-(difluoromethyl)-DL-ornithine, DFMO (McConlogue, 1987, In: Current Communications in Molecular Biology, Cold Spring Harbor Laboratory ed.). Cells to be used for ex vivo gene therapy are well known to those skilled in the art. For example, such cells include for example cancer cells present in blood or in a tissue or preferably the corresponding stem cells.

Furthermore, the invention relates to a diagnostic composition comprising the nucleic acid molecule of the invention, the vector of the invention, the polypeptide of the invention and/or the antibody of the invention.

The diagnostic composition of the invention is useful in detecting the onset or progress of diseases related to the undesired expression or overexpression of the nucleic acid molecule of the invention. As has been pointed out herein above, such diseases are interrelated or caused by an increased or ongoing cellular proliferation. Accordingly, the diagnostic composition of the invention may be used for assessing the onset or the disease status of cancer. Having thus an early criterium for tumor activity, suitable countermeasures can immediately be applied. Such an immediate action will, of course, significantly improve the prognosis of the patient. These considerations equally apply to the diagnosis of metastases and recurrent tumors.

On the other hand, not all types of tumors may be characterized by an undesired expression or overexpression of the nucleic acid molecule of the invention. Alternatively, said (over)expression may occur only in certain stages, such as early stages, of tumor development. Therefore, the diagnostic composition of the invention may also or alternatively be employed as a means for the classification of tumors or of the developmental status of a tumor. Naturally, the or most of the applications of the composition of the invention described here for tumors also apply to other diseases interrelated with or caused by the undesired (over)expression of the nucleic acid molecule of the invention.

Furthermore, a disease as recited throughout this specification also could be caused by a malfunction of the polypeptide of the present invention. Said disease could be interrelated or caused by, for example, an increased or reduced gene dosis of the polypeptide of the present invention, an increased or reduced activity of said polypeptide e.g. due to a modification in the primary amino acid sequence as compared to the corresponding wild-type polypeptide in a cell or tissue or a loss of the regulation of the activity of said polypeptide. Said disease might further be caused by an incorrect expression of the polypeptide during cell cycle progression or cell development. For example, mutated binding sites to intracellular or extracellular compounds, e.g. ions or second messengers or regulatory proteins, might result in a malfunction of the polypeptide of the present invention as it changes the binding characteristics for said compounds regulating the activity of said polypeptide. Malfunction could also be caused by defective modifications sites, for example, phosphorylation or glycosylation sites. It also might be caused by incorrect splicing events and therefore by expression of a truncated or extended polypeptides, for example, if heag 1 is expressed instead of heagh 2 or vice versa.

Thus, in a further embodiment the diagnostic composition described above could also be used to detect a malfunction of the polypeptide of the present invention.

In a further embodiment, the invention relates to a method for preventing or treating a disease which is caused by the malfunction of the polypeptide of the invention, comprising introducing an inhibitor of the expression of the nucleic acid molecule of the present invention or an inhibitor or a modifying agent of the malfunction of the (poly)peptide of the present invention or a nucleic acid molecule coding heag or a polypeptide having heag activity into a mammal affected by said disease or being suspected of being susceptible to said disease. Methods for introduction of a nucleic acid molecule of the present invention encoding heag into a cell or subject, i.e. gene therapy, are described within this specification as well as methods for the identification of inhibitors of the expression of a nucleic acid molecule of the present invention. Furthermore, inhibitors or modifying agents of the malfunction of the polypeptide of the present invention can be identified according to methods for the identification of inhibitors inhibitors of the polypeptide of the present invention known to a person skilled in the art (see below). For example, some genetic changes causing a malfunction of the polypeptide of the present invention lead to altered protein conformational states. Mutant proteins could possess a tertiary structure that renders them far less capable of fasciliating ion transport. Restoring the normal or regulated conformation of mutated proteins is the most elegant and specific means to correct these molecular defects. Pharmacological manipulations thus may aim at restoration of wild-type conformation of the protein. Thus, the polynucleotides and encoded proteins of the present invention may also be used to design and/or identify molecules which are capable of activating the wild-type function of a derivative of the polypeptide of the present invention displaying said malfunction.

The doses and routes for the administration for the treatment of a patient in need thereof have already been discussed herein above in connection with the pharmaceutical composition of the invention. Diseases that may be treated using the method of the present-invention comprise any diseases that are correlated with cellular proliferation. Preferred diseases that fall into this category are tumor diseases such as cancer (breast cancer, neuroblastoma etc.), psoriasis, and degenerative diseases, especially those of the nervous system such as Alzheimer's disease, multiple sclerosis, lateral amyotrophic sclerosis, and Parkinson's disease.

Preferably, said inhibitor of the expression or overexpression of said nucleic acid molecule is the nucleic acid molecule of the invention that hybridizes to the nucleic acid molecule encoding the ion channel of the invention or fragment thereof. For example, this nucleic acid molecule can be an antisense oligodesoxynucleotide (ODN). The inventors could show that antisense ODNs treatment significantly reduces DNA synthesis of several tumor cells, e.g. EFM cells, SHSY-5Y cells and HeLa cells (Example 5). Thus, in a preferred embodiment the nucleic acid molecule comprises antisense ODNs.

In a further preferred embodiment, said inhibitor of polypeptide function is the antibody of the invention or a drug. Said drug can be histamine receptor H1 inhibitor. Preferably, said drug inhibits active heag, for example, acts as use-dependent, probably open-channel blocker, preferably said drug is astemizole or terfenadine. Further suitable drugs can be identified or designed by the person skilled in the art on the basis of the teachings of the present invention. Preferably, the drug will have an affinity to heag channel in the mM range, more preferable in the nM range or lower. Preferably, the drug has no effect on other channels, for example on cardiac channels.

In a further preferred embodiment of the invention, said method further comprises prior to the introduction step,
(a) obtaining cells from the mammal infected by said disease and, after said introduction step, wherein said introduction is effected into said cells,
(b) reintroducing said cells into said mammal or into a mammal of the same species.

This embodiment of the present invention is particularly useful for gene therapy purposes which will reduce the treatment duration largely and increase the effectivity and reduce (even eliminate) side effects. In addition, this embodiment of the method of the invention can also be employed in the context or in combination with conventional medical therapy. The removal from and the reintroduction into said mammal may be carried out according to standard procedures.

Preferably, the above referenced cell is a germ cell, an embryonic cell or an egg cell or a cell derived from any of these cells.

The invention further relates to a method of designing a drug for the treatment of a disease which is caused by the undesired expression or overexpression of the nucleic acid molecule of the invention comprising:
(a) identification of a specific and potent drug;
(b) identification of the binding site of said drug by site-directed mutagenesis and chimeric protein studies;
(c) molecular modeling of both the binding site in the (poly)peptide and the structure of said drug; and
(d) modifications of the drug to improve its binding specificity for the (poly)peptide.

The term "specific and potent drug" as used herein refers to a drug that potently and specifically blocks heag function.

All techniques employed in the various steps of the method of the invention are conventional or can be derived by the person skilled in the art from conventional techniques without further ado. Thus, biological assays based on the herein identified features of the ion channel of the invention may be employed to assess the specificity or potency of the drugs wherein the decrease of one or more activities of the ion channel may be used to monitor said specificity or potency. Steps (b) and (d) can be carried out according to conventional protocols described, for example, in K. L. Choi, C. Mossman, J. Aubé & G. Yellen. The International Quaternary Ammonium Receptor Site of Shaker Potassium Channels. Neuron 10, 533-541 (1993), C.-C. Shieh & G. E. Kirsch: Mutational Analysis of Ion Conduction and Drug Binding Sites in the Inner Mouth of Voltage-Gated $K^+$-Channels. Biophys. J. 67, 2316-2325 (1994), or C. Miller: The Charybdotoxin Family of $K^+$-Channel-Blocking Peptide. Neuron 15, 5-10 (1995).

For example, identification of the binding site of said drug by site-directed mutagenesis and chimerical protein studies can be achieved by modifications in the (poly)peptide primary sequence that affect the drug affinity; this usually allows to precisely map the binding pocket for the drug.

As regards step (c), the following protocols may be envisaged: Once the effector site for drugs has been mapped, the precise residues interacting with different parts of the drug can be identified by combination of the information obtained from mutagenesis studies (step (b)) and computer simulations of the structure of the binding site (since a potassium channel has recently been crystallized in the art, this can now be done by the person skilled in the art without further ado) provided that the precise three-dimensional structure of the drug is known (if not, it can be predicted by computational simulation). If said drug is itself a peptide, it can be also mutated to determine which residues interact with other in the heag molecule.

Finally, in step (d) the drug can be modified to improve its binding affinity or its potency and specificity. If, for instance, there are electrostatic interactions between a particular residue of heag and some region of the drug molecule, the overall charge in that region can be modified to increase that particular interaction; additionally, if those interactions occur with a region of heag that is not conserved with other channel proteins, it is conceivable that an improvement of that interaction while other binding factors are weakened will improve the specificity of the drug.

Identification of binding sites may be assisted by computer programs. Thus, appropriate computer programs can be used for the identification of interactive sites of a putative inhibitor and the polypeptide of the invention by computer assisted searches for complementary structural motifs (Fassina, Immunomethods 5 (1994), 114-120). Further appropriate computer systems for the computer aided design of protein and peptides are described in the prior art, for example, in Berry, Biochem. Soc. Trans. 22 (1994), 1033-1036; Wodak, Ann. N.Y. Acad. Sci. 501 (1987), 1-13; Pabo, Biochemistry 25 (1986), 5987-5991. Modifications of the drug can be produced, for example, by peptidomimetics and other inhibitors can also be identified by the synthesis of peptidomimetic combinatorial libraries through successive chemical modification and testing the resulting compounds. Methods for the generation and use of peptidomimetic combinatorial libraries are described in the prior art, for example in Ostresh, Methods in Enzymology 267 (1996), 220-234 and Domer, Bioorg. Med. Chem. 4 (1996), 709-715. Furthermore, the three-dimensional and/or crystallographic structure of inhibitors of the polypeptide of the invention can be used for the design of peptidomimetic inhibitors, e.g., in combination with the (poly)peptide of the invention (Rose, Biochemistry 35 (1996), 12933-12944; Rutenber, Bioorg. Med. Chem. 4 (1996), 1545-1558).

An exemplary strategy for identifying a specific inhibitor that may be used in accordance with the present invention is provided in the appended examples.

The invention also relates to a method of identifying an inhibitor of the expression of the nucleic acid of the inven tion or of a function of the (poly)peptide of the invention comprising:

(a) testing a compound for the inhibition or reduction of translation wherein said compound is selected from antisense oligonucleotides and ribozymes; or (b) testing a compound for the inhibition of transcription wherein said compound binds to the promoter region of the gene encoding the (poly)peptide of the invention and preferably with transcription factor responsive elements thereof; or (c) testing peptides or antibodies suspected to block the proliferative activity of the (poly)peptide of the invention for said blocking activity.

As regards alternative (b) referred to above, it may be advantageous to first characterize the promoter region and locate transcription factor responsive sequences in it. Then it would be possible to genetically manipulate the promoter to render it more sensitive to repressors or less sensitive to enhancers. Turning now to alternative (c), it may be advantageous to first locate the part or parts of the ion channel of the invention implicated in the generation of proliferation disorders. Compounds that have been positive in one of the test systems are, prima facie, useful as inhibitors.

Peptidomimetics, phage display and combinatorial library techniques are well-known in the art and can be applied by the person skilled in the art without further ado to the improvement of the drug or inhibitor that is identified by the basic method referred to herein above.

In a further embodiment, the present invention relates to a method of inhibiting cell proliferation comprising applying an inhibitor to expression of the nucleic acid of the invention or the (poly)peptide of the invention. The method of the invention may be carried out in vitro, ex vivo or when application is to a subject, in vivo.

The present invention also relates to a method of prognosing cancer and/or neurodegenerative diseases and/or psoriasis comprising assessing the expression of the nucleic acid molecule of the invention-or assessing the quantitative presence of the (poly)peptide of the invention. In a preferred embodiment said cancer is a mamma carcinoma or neuroblastoma, in a more preferred embodiment said cancer is breast adenocarcinoma, breast carcinoma ductal type, or cervix carcinoma. In a further embodiment said neurodegenerative diseases is Alzheimer's disease, Parkinson's disease, lateral amytrophic sclerosis or multiple sclerosis.

The method of the invention may be carried out in vitro, in vivo, or ex vivo. Suitable protocols for carrying out the method of the invention are well-known in the art and include, as regards in vitro techniques, Northern blotting for the assessment of the level of mRNA or the analysis of tissue by microscopic techniques using, for example, antibodies that specifically recognize the (poly)peptide of the invention. One or more these techniques may be combined with PCR based techniques which may also or in combination with further (conventional) techniques be used for the above recited assessment.

In a preferred embodiment of the above-mentioned methods of the invention, said mammal is a human, rat or mouse.

The present invention further relates to the use of the nucleic acid molecules of the invention in gene therapy. As has been pointed out here above, gene therapy may be designed to inhibit cell proliferation and thus treat any disease affected thereby such as cancer or psoriasis in a specific way. The invention particularly envisages two independent lines carrying out such gene therapy protocols:

(a) Mutagenesis of the channel together with chemical engineering of H1 antagonists (preferably of astemizole) in order to obtain a drug specific for human eag;

(b) Quantitative and qualitative analysis of the expression levels of eag in cancer tissue, in order to design a diagnostic and/or prognostic method. This would also allow the design of genetic therapies against specific tumors.

For example, the nucleic acid molecule may be introduced in vivo into cells using a retroviral vector (Naldini et al., Science 272 (1996), 263-267; Mulligan, Science 260 (1993), 926-932) or another appropriate vector. Likewise, in accordance with the present invention cells from a patient can be isolated, modified in vitro using standard tissue culture techniques and reintroduced into the patient. Such methods comprise gene therapy or gene transfer methods which have been referred to herein above.

Finally, the present invention relates to a kit comprising the nucleic acid molecule specifically hybridizing to the nucleic acid molecule encoding the (poly)peptide of the invention, the vector of the invention, the polypeptide of the invention and/or the antibody of the invention.

The kit of the invention can, inter alia, be employed in a number of diagnostic methods referred to above. The kit of the invention may contain further ingredients such as selection markers and components for selective media suitable for the generation of transformed host cells and transgenic plant cells, plant tissue or plants. Furthermore, the kit may include buffers and substrates for reporter genes that may be present in the recombinant gene or vector of the invention. The kit of the invention may advantageously be used for carrying out the method of the invention and could be, inter alia, employed in a variety of applications referred to herein, e.g., in the diagnostic field or as research tool. The parts of the kit of the invention can be packaged individually in vials or in combination in containers or multicontainer units. Manufacture of the kit follows preferably standard procedures which are known to the person skilled in the art.

Several documents are cited throughout the text of this specification. Each of the documents cited herein (including any manufacturer's specifications, instructions, etc.) are hereby incorporated herein by reference; however, there is no admission that any document cited is indeed prior art as to the present invention.

The figures show:

FIG. 1. Proliferation of wild-type (circles) and reag-expressing CHO cells as a function of time. Cells were plated in 96-well dishes and at the indicated times the tetrazolium salt MTT$^6$ (50 µg/ml) was added to the plates. After four hours incubation in humidified atmosphere (37 C.°, 5% $CO_2$), the reaction was stopped by addition of 2 volumes of 10% SDS in 1M HCl. The blue formazan crystals produced in living cells were solubilized overnight, and the resulting color was measured as optical density at the indicated wavelength. Possible non-specific effects of the transfection on the cell proliferation can be neglected, since a) the results were comparable in three independent cell lines from different species (rat, hamster and human); b) transfection with different independent clones gave the same results, and c) transfection with a, different potassium channel (Kv1.4) in the same vector (thus with a tendency to recombine at the same site) gave results comparable to WT and did not reproduce the effects of the reag transfection.

FIG. 2. Proliferation of wild type (circles) and reag expressing (triangles) CHO cells, in the presence of 0.5% FCS. This serum concentration is not able to sustain growth of normal cells, but transfected cells complete almost three cycles. Methods as for FIG. 1.

FIG. 3. DNA synthesis in CHO cells expressing different potassium channels, in the presence of normal (10%) or low (0.5%) concentrations of FCS. In control cells, WT or cells transfected with Kv1.4, the levels of DNA synthesis drop significantly in the presence of low serum concentration, whereas reag expressing cells maintain the same replication levels as in high serum concentrations.

Figure 4B:
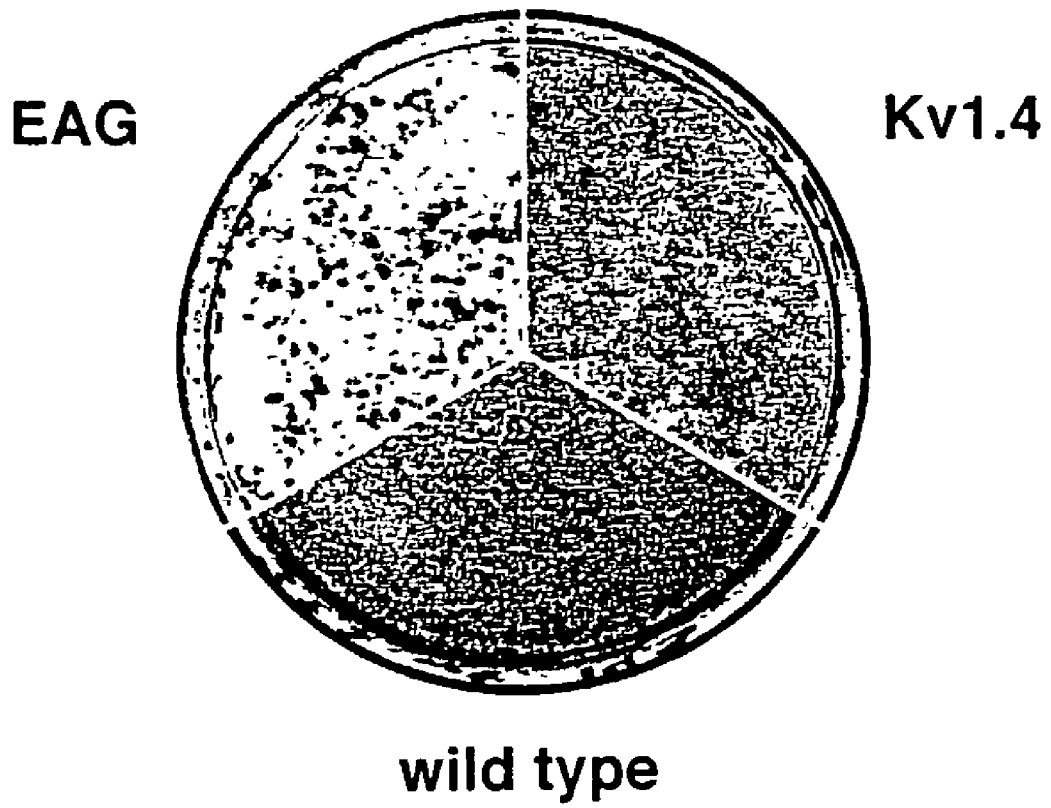

FIG. 4. (A) Photographs of plates with wild type, Kv1.4 transfected or reag transfected NIH3T3 cells. The cells were seeded at low density, and allowed to grow under standard conditions until wild-type cells reached confluence. The cells were then fixed with methanol and stained with Giemsa blue. Under those conditions, both wild type and Kv1.4-expressing cells grow in a monolayer, whereas reag expressing cells form foci. (B) Foci formation of reag -transfected NIH-3T3 cells compared to cells transfected with rKv1.4 and to wild type cells. The vector control (pcDNA3 transfected cells) yielded a similar phenotype as wild type cells (not shown). Transient transfection was carried out using calcium phosphate (33). Cells were maintained in rich medium until control cells reached confluence, then fixed with methanol and stained with Giemsa blue.

FIG. 5. Currents elicited by depolarizations in MCF7 cells under voltage clamp conditions. Left traces are whole cell currents, right traces have been obtained in an excised outside-out patch. Both the macroscopic currents and the I-V relationships (C and D) are reminiscent of reag currents.

Figure 6:
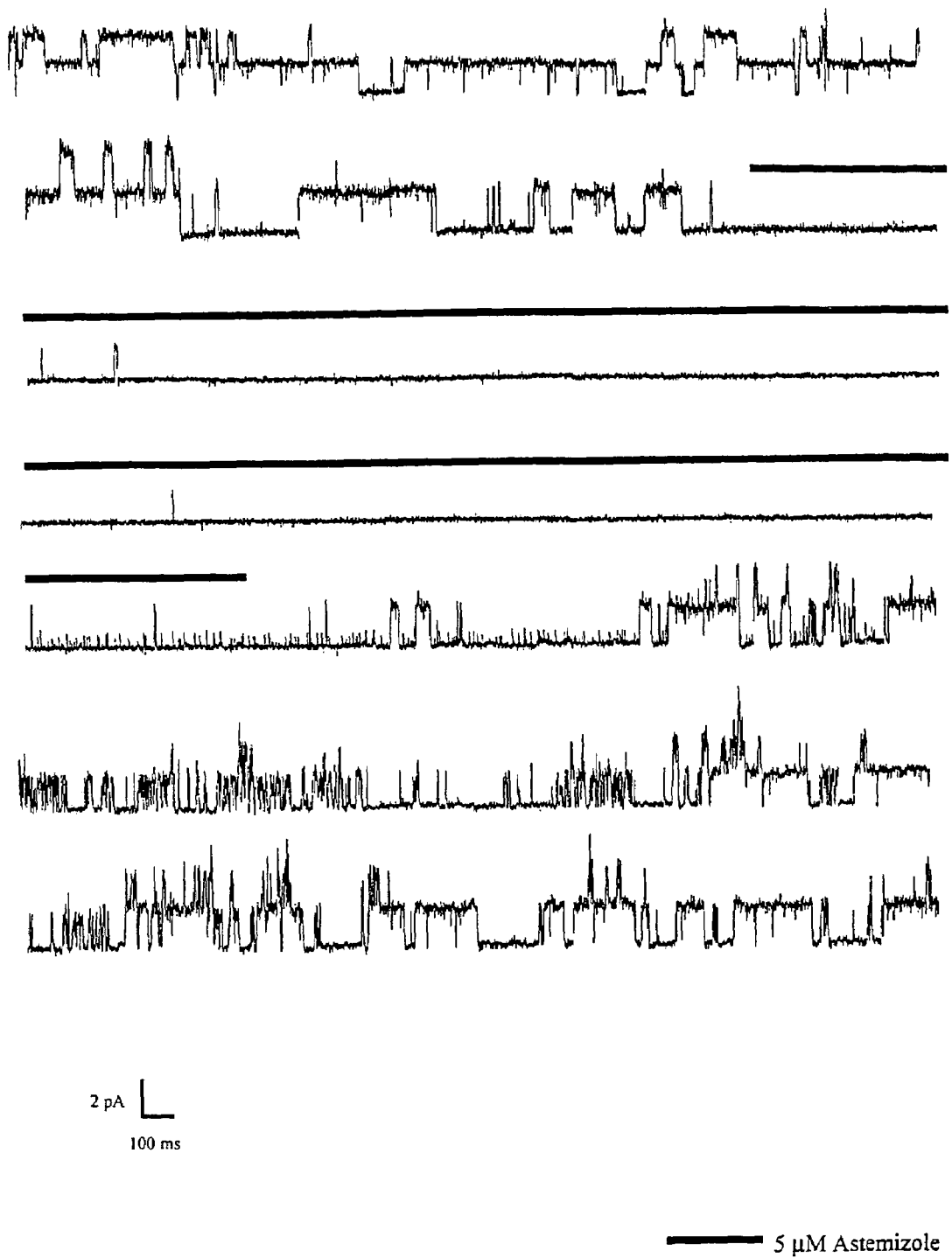

FIG. 6. Single channel activity in an outside-out membrane patch voltage-clamped at 0 mV, in the presence or the absence of 5 μM astemizole. The pipette solution contained 140 mM KCl, 10 mM BAPTA, 10 mM HEPES pH 7.2; the bath solution contained 140 mM NaCl, 2 mM $CaCl_2$, 2 MM $MgCl_2$, 2.5 mM KCl, 10 HEPES pH 7.2.

FIG. 7. A. DNA synthesis in MCF7 cells under different eag blockers. B. HEK293 DNA synthesis levels in the presence of astemizole, glibenclamide and terfenadine.

Figure 8:
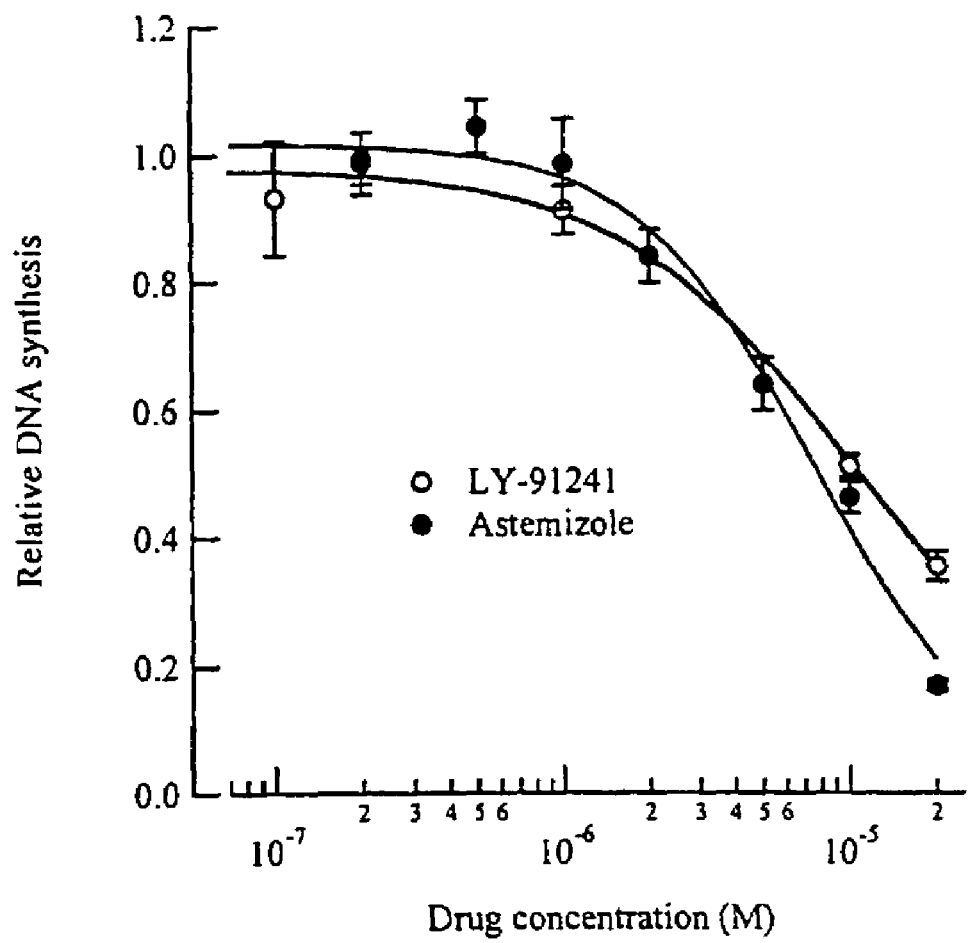

FIG. 8. Dose-response curve for the effects of two H1 antagonists on DNA synthesis in MCF7 cells (IC507 and 10 mM for LY 91241 and astemizole respectively).

FIG. 9. Fluorescence images of control (untreated, A) and astemizole-treated (B) MCF7 cells, stained with Hoechst 33342. Notice in B the smaller surface of the nuclei, and a much lower cell density (due to cell death).

FIG. 10. Nucleotide sequence of human-eag cDNA (heag; SEQ ID NO: 1) from human brain compared to the rat sequence (reag; SEQ ID NO: 20) and bovine sequence (beag; SEQ ID NO: 19). Those positions showing a different nucleotide in any of the sequences are shaded.

FIG. 11. Amino acid sequences of both splice variants (heag1 (SEQ ID NO: 3) and heag2 (SEQ ID NO: 4)) obtained from human eag cDNA translation, compared to the corresponding bovine (beag1; SEQ ID NO: 21; beag2; SEQ ID NO: 22), mouse (meag; SEQ ID NO: 23) and rat (reag; SEQ ID NO: 24) sequences. The black boxes indicate a different residue in any of the sequences.

Figure 12:
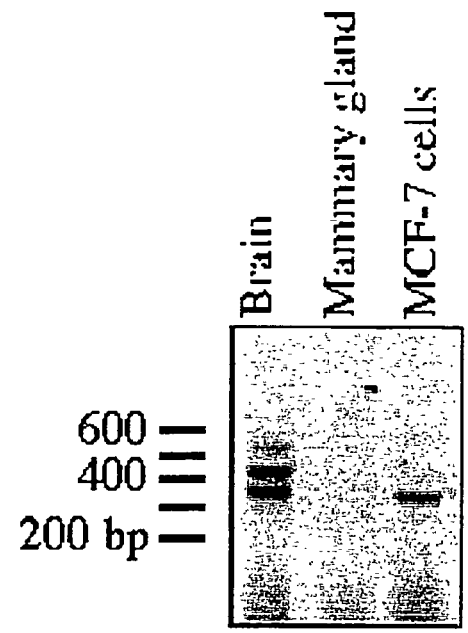

FIG. 12. RT-PCR from human brain, human mammary gland and MCF-7 cells total RNA. The amplification produced two specific fragments corresponding to the expected sizes for heag 1 and 2 in brain, and the band corresponding to heag 1 in MCF-7 cells, while no amplification was detected in normal breast RNA.

Figure 13:
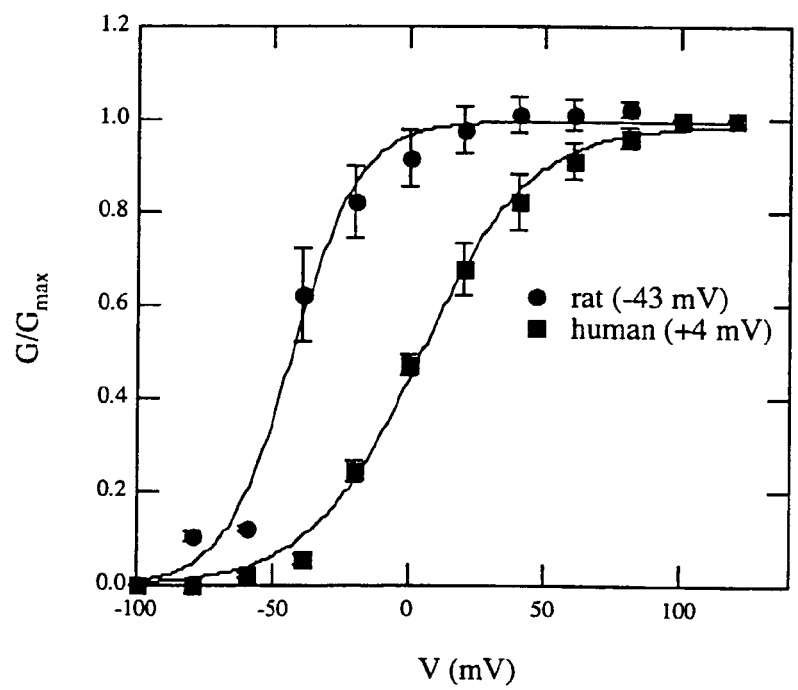

FIG. 13. Voltage-dependence of activation in high extracellular potassium, two-electrode voltage-clamp: In the conductance-voltage plot, the voltage for half-activation is shifted by 40 mV to the right in the heag channel with respect to the reag channel.

FIG. 14. Colony formation in semisolid medium of NIH-3T3 cells transfected with the indicated DNAS. Cells were plated in regular medium containing 0.3% agar onto a layer of 0.55% agar medium. Colonies larger than 0.1 mm in diameter were scored 14 days after transfection. The average number of colonies in at least ten counted microscope fields is expressed per μg DNA used in the transfection (except for the lanes "Transfection buffer" and "No treatment", where the numbers are absolute values). reag and Kv1.4 were transfected using either pcDNA3 or pTracer CMV vectors.

Figure 15:
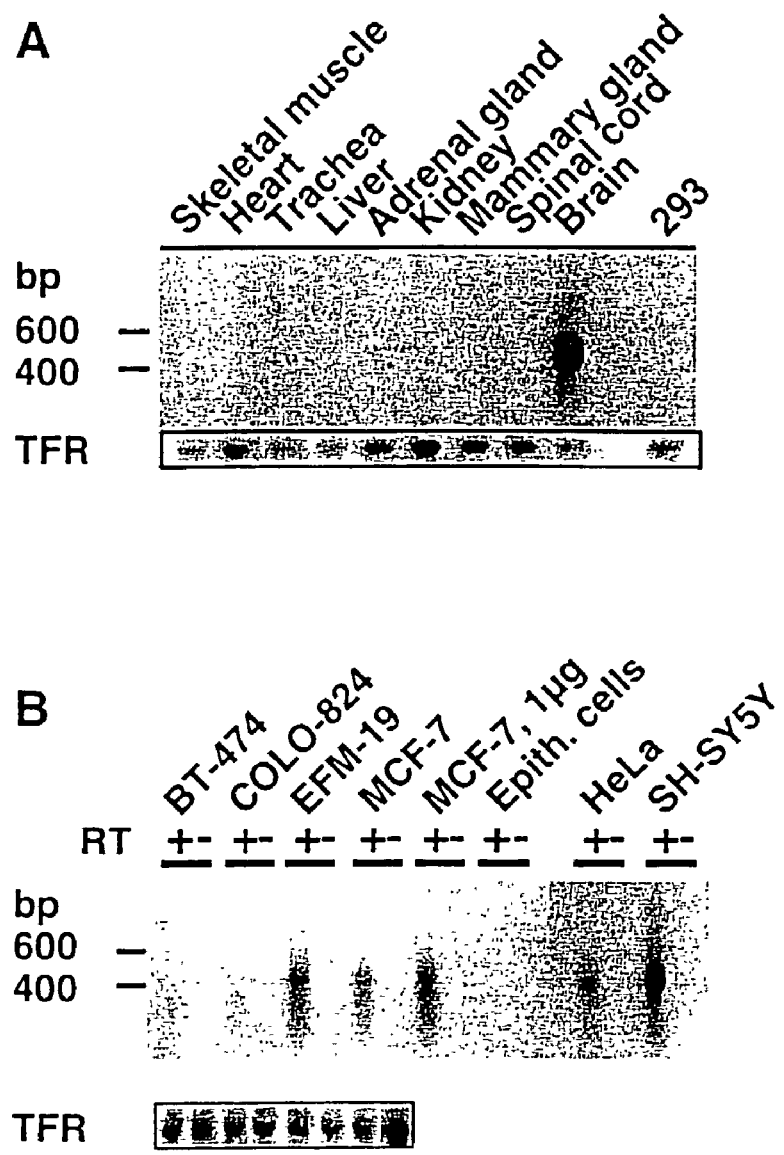
Figure 16:
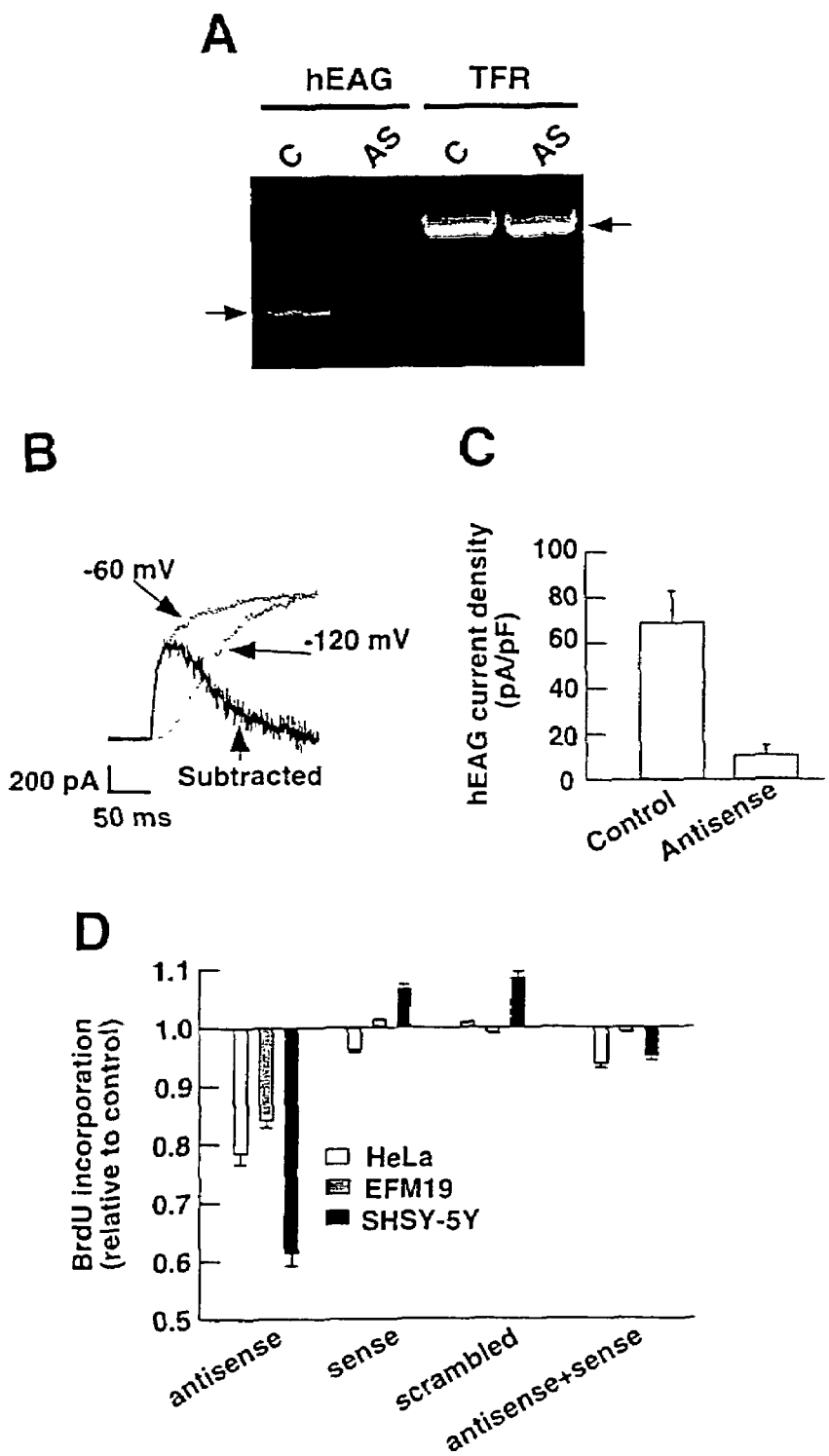

FIG. 15. (A) Southern blot of RT-PCR products of RNAs from different human tissues and 293 cells. Transferrin receptor (TFR) signals are shown at the bottom. (B) Southern blot analysis of RT-PCR products of total RNAs from different human cell lines and mammary epithelial cells in primary culture (Epith. cells). TRF signals are shown at the bottom:

FIG. 16. (A) Treatment of heag expressing tumor cell lines with antisense ODNs. (B) heag current in SHSY-5Y neuroblastoma cells (C) Current density in SHSY-5Y cells treated with antisense ODNs (D) Inhibition of DNA synthesis in human cancer cells (EFM-19, HeLa and SHSY-5Y) by antisense ODNs directed against heag.

Figure 17:
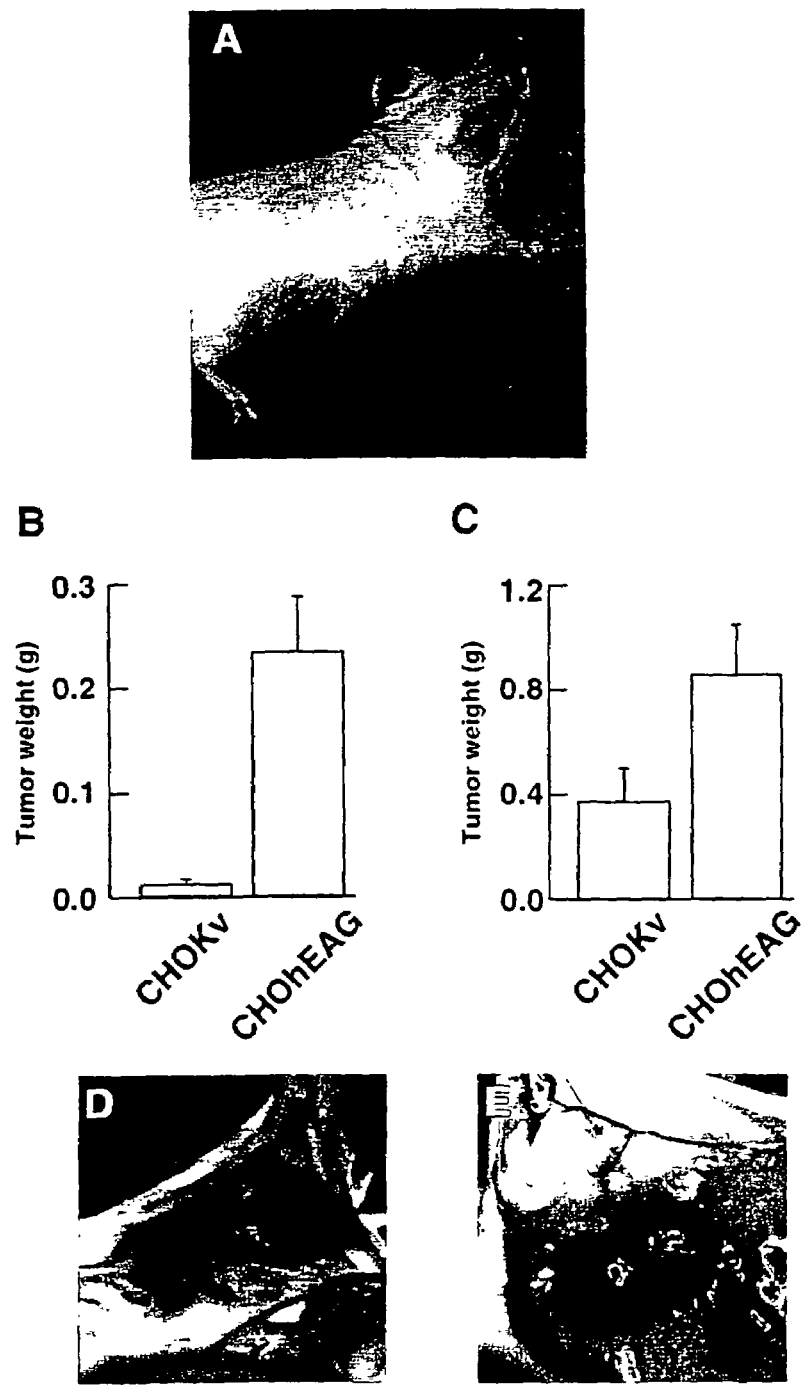
Figure 17:
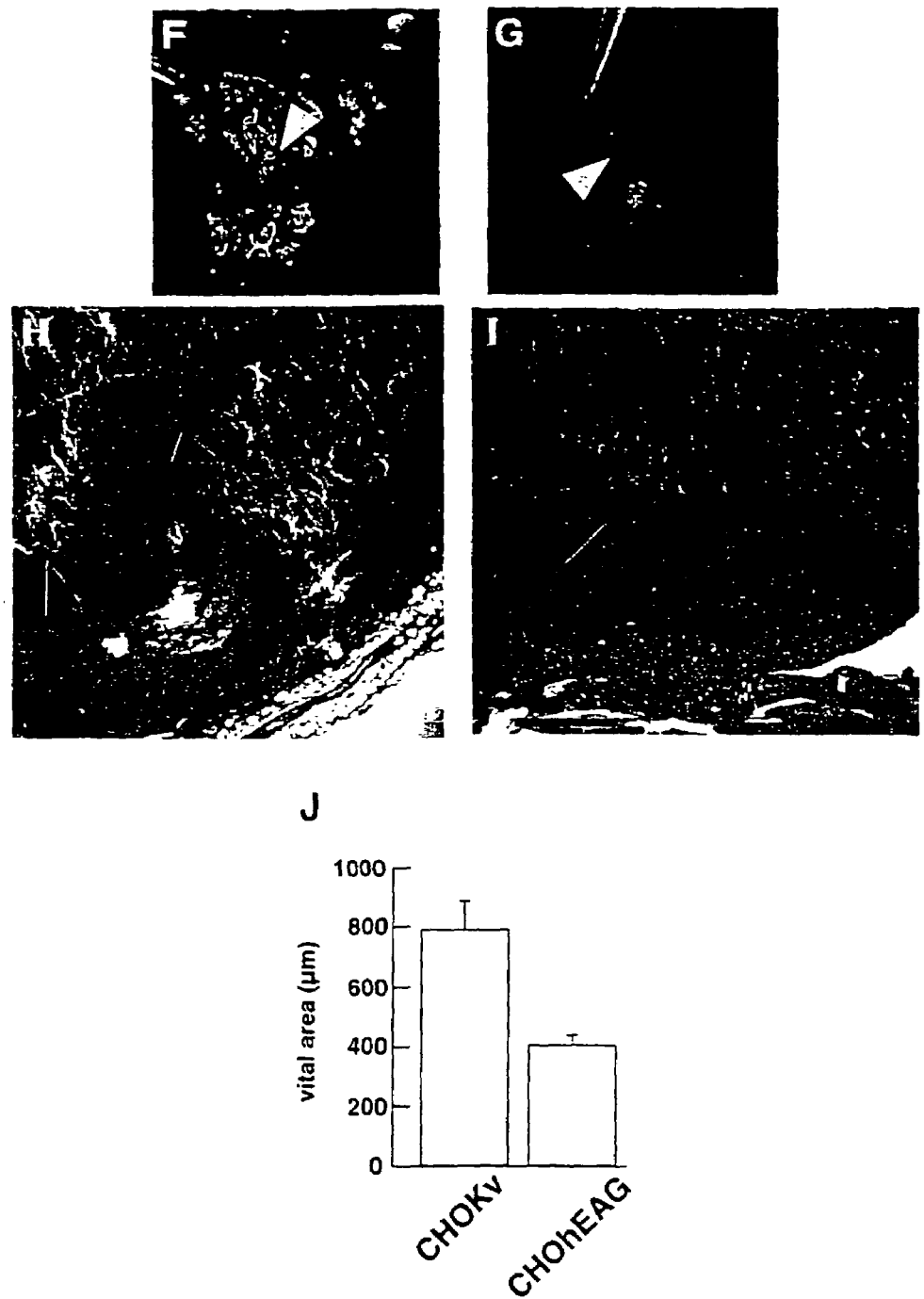

FIG. 17. (A) Subcutaneous implantation of CHOhEAG cells induced aggressive tumors that grew rapidly and soon broke the skin of the carrier mice. The photograph was taken in the third week post-implantation of $2 \times 10^6$ cells. (B,C) The average mass of CHOhEAG tumors was significantly greater than that of the CHOKv tumors both two weeks (B; mean±S.E.M.; p=0.002) or three weeks post-implantation (C; mean±S.E.M.; p=0.03) (D) CHOhEAG and (E) CHOKv tumors photographed in situ. The main macroscopic differences are the darker color and the fixation to the skin of the CHOhEAG tumor. (F, G) CHOhEAG (F) and CHOKv (G) tumors were cut open to show the great extent of necrosis (arrowheads) in the former. (H, I) The greater degree of necrosis and the fixation to the skin are also evident microscopically after paraffin embedding and hematoxylin-eosin staining. The histology is comparable in both micrographs, but in (H) a much bigger necrotic area is observed (arrowheads), and there is no border between the subcutaneous fat and the tumor. (Scale bars, 100 μm) (J) As a quantitative measurement of these images, the average width of the vital area in CHOKv tumors was significantly larger than that of CHOhEAG tumors (mean±S.E.M.; p<0.0005).

Figure 18:
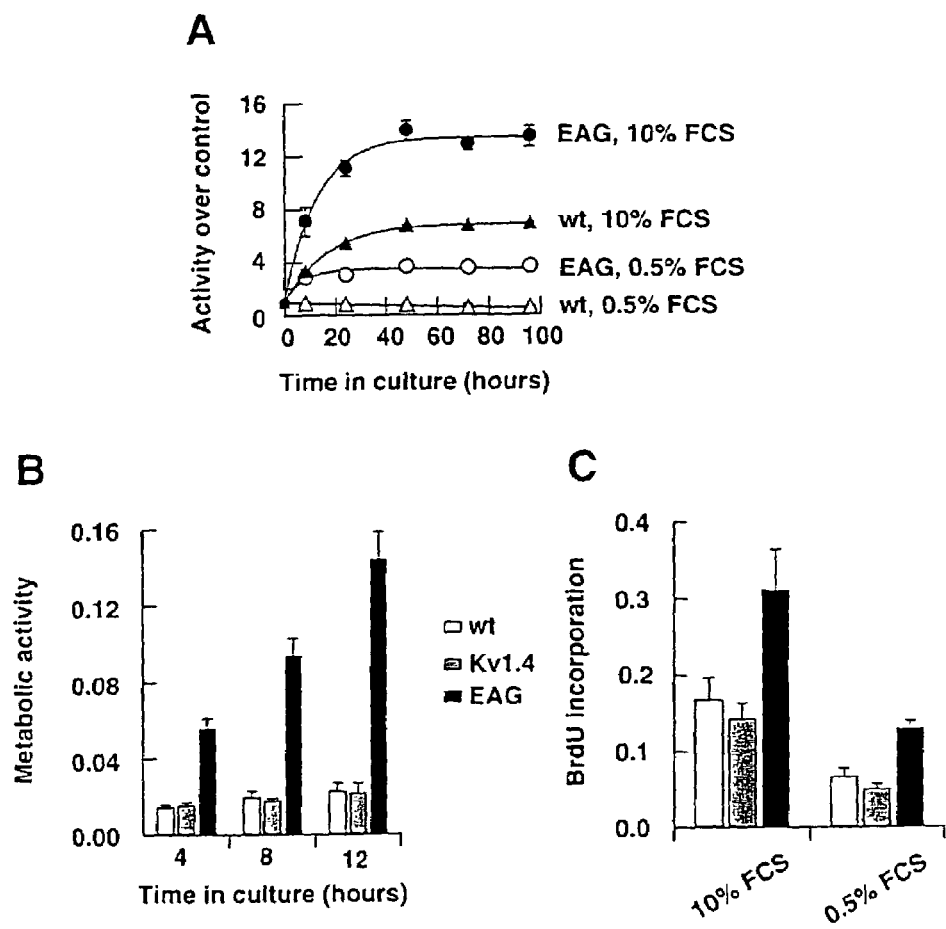

FIG. 18: Proliferation assays of rEAG-transfected CHO cells (A-C). Growth curves of CHO cells transfected with rEAG (circles) as compared to naive cells (triangles) in 10% (filled symbols) or 0.5% (open symbols) fetal calf serum. The values are referred to the ones measured after 12 h in culture (time 0 in the plot), and represent mean±S.E.M. of eight wells in the same plate. Cell lines were established by selection through the GA-418 resistance encoded in the pcDNA3 vector. MTT hydrolysis (22) was used to measure metabolic activity of viable cells. Serum was carefully diluted 12 hours after plating. (B) Increase in metabolic activity during the first 12 hours after removal of S-phase block. For cell synchronization, 2 mM thymidine was added to the culture medium for 12 h. Thymidine was removed from the medium for additional 12 h, and then a second arresting pulse was applied for 12 h. Cells were then trypsinized and plated for metabolic activity and DNA synthesis determination. (C) BrdU incorporation' during the first 12 hours after removal of S-phase block for 12 h incubation in 10% FCS, or in the presence of 0.5% FCS (24 h incubation). BrdU incorporation was measured using the Boehringer-Mannheim "BrdU labeling and detection kit", following the indications of the manufacturer. The bars represent mean±S.D. for wild-type CHO cells (open bars), Kv1.4-transfected (shaded bars) and eag-transfected (solid bars). The incorporation of BrdU is quantified as optical density at 405 nm (reference 490 nm) produced on ABTS™ substrate by peroxides coupled to the anti BrdU antibody.

The examples illustrate the invention.

EXAMPLE 1

Cloning of the K$^+$ Ion Channel mRNA was purified from total RNA obtained from MCF-7 cells following standard procedures. Then, cDNA was prepared by reverse transcription with Superscript II reverse transcriptase; this cDNA was used as a template for PCR amplification using degenerate oligonucleotides designed to match highly conserved eag sequences. After amplification, a SacII/SacII fragment from rat eag was used as a probe for Southern blot analysis of the results. Those bands showing positive hybridization were subsequently cloned in pGEM-T vector (Promega) and sequenced. All of them gave sequences corresponding to HERG.

Specific oligonucleotides engineered to avoid HERG cDNA amplification were then designed, taking into account rat, mouse and bovine eag. We looked for sequences having high homology between the various eag clones but with maximal divergence to the HERG sequence.

The sequences of the oligonucleotides were the following:
5'-CAGAA(T,C)AA(T,C)GTGGC(A,C,T,G,)TGGCT (SEQ ID NO: 8).
5'-TCACT(G,A)AAGATCTATA(A,G)TC (SEQ ID NO: 9).

After PCR amplification, the band of the expected size was cloned into pGEM-T and sequenced. The sequence obtained showed high homology to rat eag (nucleotides 942-1108).

This band was labeled and used as a probe to screen a mammary gland cDNA library. After screening of 2×10$^6$ phages, no positive clones were found.

We then used specific oligonucleotides to analyze cDNA using PCR from human heart and human brain (obtained from total RNA purchased from Clontech). Two PCR products from brain were sequenced, and the sequence corresponded to two alternatively spliced variants of eag. To further test the possibility of cloning the full length molecule from the human brain, we performed PCR analysis of a human cDNA library, and compared this result to the same experiment in the human mammary gland library (both from Clontech). Only the brain library gave positive results.

Subsequently, the amplified fragment was employed to screen the human brain library (2 rounds, 10$^6$ phages) and several clones that were cloned into the pBSK-vector were found and sequenced. All of them corresponded to the central part of the molecule, but were missing the 5' and 3' ends. The longest of these positive clones was used to prepare a probe and re-screen the library (again two rounds, 2×10$^6$ clones).

The sequences obtained in this case corresponded to part of the coding sequence (approximately 400 bp 5' were missing until the initiation codon) and a long 3' untranslated sequence. Since the fragment close to the 5' end of the molecule started in all cases with an EcoRI site, it was suspected that the site was actually present in the heag sequence, and that is was lost in the subcloning of the fragments into vectors for sequencing.

To obtain the full length sequence, we pooled those phages that carried fragments close to the 5' end and analyzed them by PCR amplification, using the sequence 3' to the mentioned EcoRI site and a sequence from lambda gt10 as primers for the PCR. After successive fractionation of the pools, two phages that carried the 5' end of the coding sequence were obtained, and one of them contained part of the 5' untranslated region.

Once we knew the complete sequence, we assembled the whole clone starting from two phages, one of them containing the 3' UTR and most of the coding sequence, and the other containing the 5' end. The first fragment was extracted from the phage by SphI/HindIII digestion, and subcloned into pBKS- to produce pBKSheag 1. In this was, a 1.2 kbp SphI-SphI fragment was also removed from the clone, and it was necessary to reintroduce it afterwards. The fragment containing the 5' end was extracted by HindIII/MunI digestion. This fragment was ligated with a HindIII/MunI digest of pBKSheag 1. Only using this procedure were we able to obtain the full length clone in a single plasmid. We then needed to reintroduce the SphI-SphI fragment since we had deleted one of the SphI sites. Subsequently, an EagI/NotI fragment was subcloned into the NotI site of pCDNA3 vector, to eliminate the contaminating phage sequences and to obtain a vector suitable for functional expression of the channel. Finally obtained sequences are depicted in sequence listing as SEQ ID No. 1 and SEQ ID No. 2.

EXAMPLE 2

Identification of Inhibitors That Specifically Bloc the Action of Human Eag.

Another member of the eag family, HERG[11-16], has been related to a familiar form of long QT syndrome (LQT). This has allowed to identify several blockers of HERG based on their ability to induce LQT-type arrythmias. Thus, certain histamine H1 receptor blockers, such as astemizole and terfenadine, as well as class III antiarrythmic drugs (dofetilide, E-4031) are potent and specific blockers of HERG[15,17]. However, for eag channels, specific blockers have not yet been described. Due to the sequence similarity between HERG and eag channels, both groups of drugs on reag were tested in accordance with the present invention. The H1 blockers also affect reag, whereas the channel is rather insensitive to class III antiarrythmics (dofetilide). This provides a useful tool to selectively block eag-type channels and to discard possible effects of HERG channels (which are also present in MCF7 cells). The effect of one of these drugs (astemizole 5 µM) is shown on single putative human eag channels in FIG. 6.

It was further tested whether several reag and other potassium channel blockers are able to inhibit growth of MCF7 cells. As a "positive" control glibenclamide, a blocker of the ATP-sensitive potassium channel was also included, since it has been described to inhibit the proliferation of this cell line . To determine the rate of DNA synthesis, cells were plated on 96-well microtiter plates at a density of ≈10$^5$ cells/ml and in the absence of growth factors. After 24 hours starvation, cells were stimulated by addition of 10% FCS in the presence of BrdU. The amount of BrdU incorporated into the newly synthesized DNA was determined using a commercial antibody (Boehringer Mannheim). The drugs tested were added either at the same time or 12 hours prior to the stimulation. In a different human cell line, HEK293, the addition of 10 μM astemizole or 100 μM glibenclamide did not reduce significantly the DNA synthesis, while terfenadine (10 μM) produced a strong inhibition. For this reason, only effects of astemizole (and its closely related analog LY91241) were considered, and those produced by terfenadine (although MCF7 cells are significantly more sensitive to growth inhibition by terfenadine than the control cells) discarded. In MCF7 cells, 5 μM astemizole reduced the DNA synthesis by 40%, while the same concentration of the HERG-specific blocker dofetilide produced no significant effects. Ten times higher concentrations (50 μM) of other potassium channel blockers (quinidine or glibenclamide) where required to induce a similar effect. A dose-response curve for astemizole effects on DNA synthesis in MCF7 cells is depicted in FIG. 8. The half-maximal effect was obtained for 10 μM astemizole.

In an attempt to clarify the mechanism underlying the proliferation inhibition in MCF7 cells, the nuclear morphology of cells treated with 5 μM astemizole were checked, using the supravital nuclear stain Hoechst 33342. After 24 hours of treatment, most cells showed nuclear condensation and fragmentation, typical features of apoptotic cell death (FIG. 9).

In conclusion, a human counterpart of the reag channels are present in human cancer cells, and they have the ability to induce malignant transformation in several different cell types.

EXAMPLE 3

Expression of Heag in Different Human Tissues 500 ng total RNA from different tissues (or 5 ng polyA$^+$ RNA, for spinal cord) were reverse transcribed and amplified using a pair of oligonucleotides of the sequences, 5'-CGCATGAACTACCTGAAGACG (SEQ ID NO: 10) (forward) and 5'-TCTGTGGATGGGGCGATGTTC (SEQ ID NO: 11) (reverse). The amplified DNA was analyzed by Southern blot using a specific human eag probes (a 1.5 kb EcoRI fragment from the core of the channel). Among the RNAs tested, only brain total RNA gave positive signals. RNAs from spinal cord, adrenal gland, skeletal muscle, heart trachea, liver, kidney and mammary gland were negative. The integrity of the RNA was checked using transferrin amplification. Using the same approach, the expression of heag in several tumoral human cell lines was checked, in: MCF-7 (breast adenocarinoma), BT-474 (breast ductal carcinoma, from a solid tumor), EFM-19 (breast carcinoma, ductal type, from pleural fluid), COLO-824 (breast carcinoma, ductal type, from pleural fluid), SHSY5Y (neuroblastoma).

In contrast to normal tissues, all the cancer cell lines tested were found positive for heag expression.

Further, Southern blot of RT-PCR products of RNAs from different human tissues and 293 cells show that only in RNA from brain the two bands corresponding to heag A and B could be amplified and identified. Transferrin receptor (TFR) signals are shown at the bottom (FIG. 15A). Furthermore, a Southern blot analysis of RT-PCR products of total RNAs from different human cell lines and mammary epithelial cells in primary culture (Epith. cells). TRF signals are shown at the bottom. RNAs from different cell lines (34) and commercial RNAs from human tissues (Clontech) were subjected to single-tube RT-PCR (35). Total RNA was used with the exception of spinal cord, where poly(A)$^+$ RNA was used (primer sequences were: forward: 5'-CGCATGAAC-TACCTGAAGACG (SEQ ID NO: 10) and reverse: 5'-TCT-GTGGATGGGGCGATGTTC (SEQ ID NO: 11). 5'-TCAGCCCAGCAGAAGCATTAT (SEQ ID NO: 17) and reverse: 5'-CTGGCAGCGTGTGAGAGC (SEQ ID NO: 18) were used to control RNA and PCR performance.). Specific primers for TFR were used to control RNA and PCR performance. These ODNs were designed according to the published TFR sequence (36), starting at exon 11 and spanning to exon 19 (37). This, together with the amplification of two heag splice fragments and controls in the absence of reverse transcriptase, excludes a false positive due to genomic DNA contamination. 50 μl (heag) or 15 μl (TFR) of PCR reactions were analyzed in 2% agarose gels. DNA was transferred to membranes and consecutively hybridized at high stringency with [$^{32}$P]-dCTP labeled random primed probes consisting of a 980 bp heag fragment and the TFR fragment amplified from brain RNA.

EXAMPLE 4

Expression of Heag In Vivo

To determine whether the expression of heag is advantageous for tumor cells in vivo, the inventors preformed subcutaneous implants of CHO cells expressing the channel (CHOhEAG cells) into the flank of female scid (severe combined immunodeficiency, 33) mice. CHOKv cells were used as a control. Therefore, 2×10$^6$ CHOhEAG or CHO-Kv1.4 cells suspended in 100 μl PBS were implanted subcutaneously on the flank of 6-8 week old female Fox Chase scid mice (C.B-17/Icr sicd/scid) obtained from Bomholtgard, Ry, Denmark. The presence of tumors was checked every second day by tactile inspection of every mouse. After two or three weeks, the animals were sacrificed by cervical dislocation and the tumors dissected and fixed in paraformaldehyde for subsequent paraffin inclusion and staining. The identity of the CHOhEAG cells was established by UV illumination of the tumors to evoke fluorescence from the green fluorescence protein encoded in the pTracer vector (Invitrogen). One week after the implantation, all CHOhEAG-injected mice carried tumors detectable by palpation, while no mass greater than 1 mm was observed in the controls. During the second week post-implantation, the heag -expressing tumors reached in excess of 5 mm in diameter and visibly emerged through the skin in most cases (FIG. 17A); the mice were sacrificed after two (N=6) or three weeks (N=-7). Only one of the 11 control animals used was free of visible tumors; all 13 CHOhEAG-injected animals showed tumors. The average mass (FIGS. 17B, C) of the heag -expressing tumors was significantly larger than that of controls, especially two weeks following implantation (FIG. 17B). From macroscopic observation, the tumors appeared friable and hemorragic; the CHOhEAG tumors were darker than the controls and were adhered to the skin (FIGS. 17D, E) in all CHOhEAG-injected mice at two weeks. Six of seven mice exhibited similar characteristics at three weeks. In contrast, the tumor could be easily dissected from the skin inall of the control mice after two weeks, and in five out of six mice at three weeks. The tissue below the tumor appeared unaffected in all cases. The dark color was due to great extent of intratumoral necrosis (FIGS. 17F, G, arrows), confirmed by histology (FIGS. 17H, I, arrowheads), indicating a faster growth of CHOhEAG tumors. The thickness of the vital area in the EAG-expressing tumors was significantly smaller than in the controls (FIG. 17J). The rapid growth of the tumor can account for the massive intratumoral necrosis in the CHOhEAG group. This could also explain the enhanced difference found in the mass of the tumors two weeks after implantation, since CHOhEAG tumors would cease growth due to massive necrosis. These data strongly suggest that expression of heag tumors grow faster and are more aggressive than CHOKv tumors.

EXAMPLE 5

Inhibition of Heag

It is assumed that expression of heag in some tumor cells is not the consequence of their abnormal growth, but that this $K^+$ channel is necessary for their proliferation. Therefore, inhibition of heag expression with antisense oligodeoxynucleotides (ODNs) should decrease the proliferation rate in these tumor cells. Therefore, a 19-mer antisense phosphorothioate ODN (5'-CAGCCATGGTCATCCTCCC) (SEQ ID NO: 15) spanning the putative initiation codon of heag was used to test inhibition of proliferation. The sense ODN and a scrambled sequence (gtcggtaccagtaggaggg) (SEQ ID NO: 16) were used as controls. Data shown in FIG. 16A confirms the efficiency of the antisense ODN treatment in reducing the heag mRNA content in EFM cells. A reduction in heag mediated $K^+$ currents in SHSY-5Y cells by treatment with antisense ODN is shown in FIGS. 16B and C.

Treatment of heag expressing tumor cell lines with antisense ODNs significantly reduced the yield of amplified PCR products. EFM-19 cells were treated with 10 µg/ml DAC30 (lanes "C") or 10 µg/ml DAC30 (Eurogentec) plus 1 µM antisense ODN (lanes "AS") overnight, total RNA was extracted and assayed under the same conditions as described in Example 3, with ODNs designed to either amplify heag or the transferrin receptor. The arrows in FIG. 16A mark the expected sizes of the amplified fragments. Further, to dissect the heag current in SHSY-5Y neuroblastoma cells, the inventors utilized the voltage-dependence of the activation of eag (30) in the presence of extracellular $Mg^{2+}$. The current was measured after a depolarization to +60 mV from −120 mV (FIG. 16B, gray lines). The first part of the subtracted trace (FIG. 16B, black line) corresponds to eag current that has not yet activated when the holding potential is very negative (−120 mV), but becomes evident if the holding potential is −60 mV. The average current between 19 and 21 ms was chosen to determine the current density. The current density in SHSY-5Y cells treated with antisense ODNs was significantly reduced as compared to control cells (The electrophysiological determinations were performed using standard protocols in the whole cell configuration of the patch-clamp technique (Hamill, O. P., Marty, A., Neher, E., Sakmann, B., Sigworth, F. J. Pflügers Arch-Eur. J. Physiol 391, 85 (1981)), with an extracellular solution containing (mM) 140 NaCl, 2.5 KCl, 2 CaCl2, 2 MgCl2, 10 Hepes/NaOH pH 7.2, 10 glucose. The pipette solution was (mM) 140 KCl, 10 BAPTA, 10 Hepes/KOH pH 7.2.). The cells were treated overnight with antisense ODN 1 µM containing fluorescein-labeled ODN. The currents were determined 1 to 3 days later in cells showing fluorescence in their nuclei. The bars in FIG. 16C represent mean±S.E.M. for 9 cells (control) or 25 cells (antisense). Only the outward currents were evaluated in the analysis. Furthermore, the inhibition of DNA synthesis in human cancer cells (EFM-19, HeLa and SHSY-5Y) by antisense ODNs directed against heag was investigated. DNA synthesis is expressed relative to BrdU incorporation in the absence of ODNs. The uptake conditions into cells using fluorescein labeled antisense ODN was optimized. Cells were seeded in 96-well plates at a density of 105 cells/ml. One day after plating, the cells were washed with culture medium and the ODN was added (final concentration 10 µM). The ODN had previously been mixed with 20 µg/ml of the transfection ragement DAC-30 (Eurogentec) in serum-free medium and allowed to incubate at room temperature for 20-30 min. The mixture was then added as a 1:1 dilution in culture medium and maintained in contact with cells overnight. After this incubation, the cells were washed and labeled with BrdU (100 µM) for 2 h. Incorporation was detected using the kit from Boehringer Mannheim and measured as OD units at 405 nm (reference 490 nm) after subtraction of the non-specific background incorporation. (FIG. 16D). The bars indicate mean±S.D. for eight wells per condition in a representative experiment.

Glossary and List of Abbreviations

Cell lines:

| | | |
|---|---|---|
| CHO | CHO-K1 (ATCC CCL 61) | Chinese hamster *Cricetulus griseus* ovary |
| HEK293 | 293 (ATCC CRL 1573) | Transformed primary human embryonal kidney |
| NIH3T3 | (ATCC CRL 1658) | Embryo Swiss mouse fibroblasts |
| MCF7 | (ATCC HTB 22) | Human breast adenocarcinoma |
| WT | Wild-type cells | |

Genes and gene products

| | |
|---|---|
| eag | ether-à-go-go potassium channel |
| HERG | Human-Eag-Related Gene. Codes for an inwardly rectifying potassium channel mainly expressed in heart. |
| Kv1.4 | Inactivating voltage-dependent potassium channel. Initially cloned from rat brain, it is present in many other tissues. |

Others

| | |
|---|---|
| EGF | Epidermal growth factor |
| PDGF | Platelet-derived growth factor |
| FCS | Fetal calf serum |
| I-V relation | Current-Voltage relation |
| LQT | Long Q-T (interval between Q and T waves in the electrocardiogram). Induces severe arrythmias due to repolarization defects. |
| BrdU | 5-Bromo-2'-deoxyuridine. Structure analog of thymidine. |
| IC50 | Concentration that produces 50% inhibition |
| RT-PCR. | Polymerase Chain Reaction of cDNA produced by reverse transcription in the same tube. |

REFERENCES

1. Moody, W. J. (1995). Critical periods of early development created by the coordinate modulation of ion channel properties. *Perspect Dev Neurobiol* 2, 309-315.
2. Woodfork, K. A., Wonderlin, W. F., Peterson, V. A., and Strobl, J. S. (1995). Inhibition of ATP-sensitive potassium channels causes reversible cell-cycle arrest of human breast cancer cells in tissue culture. *J Cell Physiol* 162, 163-71.
3. Lepple Wienhues, A., Berweck, S., Bohmig, M., Leo, C. P., Meyling, B., Garbe, C., and Wiederholt, M. (1996). K$^+$ channels and the intracellular calcium signal in human melanoma cell proliferation. *J Membr Biol* 151, 149-57.
4. Wonderlin, W. F., Woodfork, K. A., and Strobl, J. S. (1995). Changes in membrane potential during the progression of MCF-7 human mammary tumor cells through the cell cycle. *J Cell Physiol* 165, 177-85.
5. Brüggemann, A., Stühmer, W., and Pardo, L. A. (1997). Mitosis-promoting factor-mediated suppression of a cloned delayed rectifier potassium channel expressed in *Xenopus* oocytes. *Proc Nat Acad Sci USA* 94, 537-542.
6. Mosmann, T. (1983). Rapid colorimetric assay for cellular growth and survival: application to proliferation and cytotoxicity assays. *J. Immunol. Meth.* 65, 55-63.
7. Muir, D., Varon, S., and Manthorpe, M. (1990). An enzyme-linked immunosorbent assay for bromodeoxyuridine incorporation using fixed microcultures. *Anal. Biochem.* 185, 377-82.
8. Magaud, J. P., Sargent, I., and Mason, D. Y. (1988). Detection of human white cell proliferative responses by immunoenzymatic measurement of bromodeoxyuridine uptake. *J. Immunol. Meth.* 106, 95-100.
9. Huong, P. L., Kolk, A. H., Eggelte, T. A., Verstijnen, C. P., Gilis, H., and Hendriks, J. T. (1991). Measurement of antigen specific lymphocyte proliferation using 5-bromodeoxyuridine incorporation. An easy and low cost alternative to radioactive thymidine incorporation. *J. Immunol. Meth.* 140, 243-8.
10. Ellwart, J., and Dormer, P. (1985). Effect of 5-fluoro-2'-deoxyuridine (FdUrd) on 5-bromo-2'-deoxyuridine (BrdUrd) incorporation into DNA measured with a monoclonal BrdUrd antibody and by the BrdUrd/Hoechst quenching effect. *Cytometry* 6, 513-20.
11. Benson, D. W., MacRae, C. A., Vesely, M. R., Walsh, E. P., Seidman, J. G., Seidman, C. E., and Satler, C. A. (1996). Missense mutation in the pore region of HERG causes familial long QT syndrome. *Circulation* 93, 1791-5.
12. Curran, M. E., Splawski, I., Timothy, K. W., Vincent, G. M., Green, E. D., and Keating, M. T. (1995). A molecular basis for cardiac arrhythmia: HERG mutations cause long QT syndrome. *Cell* 80, 795-803.
13. Sanguinetti, M. C., Jiang, C., Curran, M. E., and Keating, M. T. (1995). A mechanistic link between an inherited and an acquired cardiac arrhythmia: HERG encodes the IKr potassium channel. *Cell* 81, 299-307.
14. Spector, P. S., Curran, M. E., Keating, M. T., and Sanguinetti, M. C. (1996). Class III antiarrhythmic drugs block HERG, a human cardiac delayed rectifier K$^+$ channel. Open-channel block by methanesulfonanilides. *Circ Res* 78, 499-503.
15. Trudeau, M. C., Warmke, J. W., Ganetzky, B., and Robertson, G. A. (1995). HERG, a human inward rectifier in the voltage-gated potassium channel family. *Science* 269, 92-5.
16. Suessbrich, H., Waldegger, S., Lang, F., and Busch, A. E. (1996). Blockade of HERG channels expressed in *Xenopus* oocytes by the histamine receptor antagonists terfenadine and astemizole. *FEBS Lett* 385, 77-80.
17. For example, see: DeCoursey, T. E., Chandy, K. G., Gupta, S., Cahalan, M. D. Nature 307, 465 (1984); Mauro, T., Dixon, D. B., Komuves, L., Hanley, K., Pappone, P. A. J. Invest. Dermat. 108, 864 (1997).
18. Rouzaire-Dubois, B. and Dubois, J. M. *J. Physiol.* 510, 93 (1998).
19. Arcangeli, A., L. Bianchi, et al. *J. Physiol.* 489, 455-471 (1995). Bianchi, L. et al., *Cancer Res.* 58, 815-822 (1998).
20. Brüggemann, A., Stühmer, W., Pardo, L. A. Proc. Natl. Acad. Sci. USA. 94, 537 (1997). Pardo, L. A., Brüggemann, A., Camacho, J., Stührner, W. J. Cell. Biol. 143, 767 (1998).
21. Ludwig, J., et al., *EMBO J.* 13, 4451 (1994).
22. Mosmann, T. J. Immunol. Meth. 65, 55 (1983). Cells were incubated with MTT (Thiazolyl blue) 50 µg/ml for 4 h, and the formazan crystals were solubilized in 10% SDS, 10 mM HCl for 12-14 h. The optical density at 570 nm was measured using an ELISA reader, with a reference wavelength of 650 nm.
23. Stein, G. S. et al., in Cell Growth and Apoptosis. A Practical Approach, G. P. Studzinski, Ed. (IRL Press, Oxford, 1995) pp. 193-203.
24. Jainchill, J. L., Aaronson, S. A., Todaro, G. J. J. Virol. 4, 549 (1969).
25. Hermouet, S., Merendino, J. J., Jr., Gutkind, S., Spiegel, A. M. Proc. Natl. Acad. Sci. USA 88,10455 (1991).
26. GenBank Accession Numbers for the sequences reported in this paper are AF078741 (heag A) and AF078742 (heag B).
27. Occhiodoro, T. et al., FEBS Lett. 434, 177 (1998).
28. Warmke, J. W. and Ganetzki, B. Proc. Natl. Acad. Sci. USA. 91, 3438 (1994). Frings, S., et al., J. Gen. Physiol. 111, 583 (1998).
29. Heng, H. H. Q., Squire, J., Tsui, L.-C. Proc. Natl. Acad. Sci. USA, 89, 9509 (1992); Heng, H. H. Q., and Tsui, L.-C. Chromosoma, 102, 325 (1993). We acknowledge Dr. Henry Heng (SeeDNA Biotech, Downsview, Ontario, Canada) for FISH analysis.
30. Terlau, H., et al., Pflügers Arch. —Eur. J. Physiol., 432, 301 (1996). Terlau, H., Heinemann, S. H., Stühmer, W., Pongs, O., Ludwig, J. J. Physiol., 502, 537-543 (1997). Meyer, R. and Heinemann, S. H. J. Physiol. 508, 49 (1998).
31. Bijlenga, P., et al. J. Physiol. 512, 317 (1998).
32. Bosma, G. C., et al. Nature 301, 527-530 (1987)
33. Chen, C. and Okayama, H. Mol. Cell Biol. 7,2745 (1987).
34. Chomczynski, P. and Sacchi, N. Anal. Biochem. 162, 156 (1987).
35. Soto, F., et al., Proc. Natl. Acad. Sci. USA. 93, 3684 (1996).
36. McClelland, A., Kühn, L. C., Ruddle, F. H. Cell 39, 267 (1984). Schneider, C., Owen, M. J., Banville, D., Williams, J. G. Nature 311, 675 (1984).
37. Evans, P. and Kemp, J. Gene 199, 123 (1997).

This application incorporates by reference international application PCT/EP99/02695, filed Apr. 21, 1999, which designated the United States.

The invention claimed is:

1. A method of prognosing cancer in a mammal, comprising assessing the quantitative presence of a polypeptide having the function of the human $K^+$ eag ion channel and encoded by a nucleic acid sequence selected from the group consisting of:
   (a) a nucleic acid sequence encoding the polypeptide having the amino acid sequence SEQ ID NO:3;
   (b) a nucleic acid sequence that hybridizes to the complementary strand of the nucleic acid sequence of (a) at 4×SSC at 65° C. or at 4×SSC at 42° C. in 50% formamide, followed by washing in 0.1×SSC at 65° C. for one hour; and
   (c) a nucleic acid sequence that is degenerate to the nucleic acid sequence of (b); in cells of the mammal to be tested, wherein the presence of the polypeptide in the cells compared to normal cells indicates cancer.

2. The method according to claim 1, wherein the cancer is breast carcinoma, neuroblastoma or cervical carcinoma.

3. The method according to claim 2, wherein the breast carcinoma is breast adenocarcinoma or breast carcinoma ductal type.

4. The method according to any one of claims 1 to 3, wherein the mammal is a human.

5. The method according to claim 1, wherein the nucleic acid sequence is the nucleic acid sequence of part (a).

6. The method according to claim 1, wherein the nucleic acid sequence is the nucleic acid sequence of part (b).

7. The method according to claim 1, wherein the assessment of the quantitative presence of the polypeptide is carried out, in vitro or ex vivo.

8. The method according to claim 1, wherein the quantitative presence of the polypeptide is assessed by using an antibody that specifically recognizes the polypeptide.

9. The method according to claim 1, wherein the quantitative presence of the polypeptide is assessed by analyzing tissue by microscopic techniques.

* * * * *

SEQUENCE LISTING

<160> NUMBER OF SEQ ID NOS: 24

<210> SEQ ID NO 1
<211> LENGTH: 3002
<212> TYPE: DNA
<213> ORGANISM: Homo sapiens

<400> SEQUENCE: 1

| | | | | | |
|---|---|---|---|---|---|
| aattccgggc | ccgccggacc | ccgagctgct | gggaggatga | ccatggctgg | gggcaggagg | 60 |
| ggactagtgg | cccctcaaaa | cacgtttctg | gagaatattg | ttcggcggtc | caatgatact | 120 |
| aattttgtgt | tggggaatgc | tcagatagtg | gactggccta | ttgtgtacag | caatgatgga | 180 |
| ttttgcaagc | tgtctggcta | tcacagggca | gaagtgatgc | aaaaaagcag | cacctgcagt | 240 |
| tttatgtatg | gggagctgac | tgataaagac | acgattgaaa | aagtgcggca | aacatttgag | 300 |
| aactatgaga | tgaattcctt | tgaaattctg | atgtacaaga | gaacaggac | acctgtgtgg | 360 |
| ttctttgtga | aaattgctcc | aattcgaaac | gaacaggata | agtggttttt | atttctttgc | 420 |
| actttcagtg | acataacagc | tttcaaacag | ccaattgagg | atgattcatg | taaaggctgg | 480 |
| gggaagtttg | ctcggctgac | aagagcactg | acaagcagca | ggggtgtcct | gcagcagctg | 540 |
| gctccaagcg | tgcaaaaagg | cgagaatgtc | cacaagcact | cccgcctggc | agaggtccta | 600 |
| cagctgggct | cagacatcct | tccccagtac | aagcaagagg | caccaaagac | tccccctcac | 660 |
| atcatcttac | attattgtgt | ttttaagacc | acgtgggatt | ggatcatctt | gatcttgacc | 720 |
| ttctatacag | ccatcttggt | cccttataat | gtctccttca | aaaccaggca | gaataatgtg | 780 |
| gcctggctgg | ttgttgatag | catcgtggat | gttatctttt | tggtggacat | tgtgctcaat | 840 |
| tttcatacca | cctttgttgg | accagcaggg | gaggtgattt | ctgaccccaa | acttatccgc | 900 |
| atgaactacc | tgaagacgtg | gtttgtgatt | gaccttctgt | cctgtttgcc | atatgatgtc | 960 |
| atcaacgctt | ttgagaacgt | ggatgagggc | atcagcagcc | tgttcagctc | tctaaaagtt | 1020 |
| gtccggctgc | tccgtcttgg | gcgagtggcc | cgtaagctgg | accactacat | tgaatatgga | 1080 |
| gctgctgtgc | tggtcctgct | ggtgtgtgtg | tttgggctgg | ctgcacactg | gatggcctgc | 1140 |
| atctggtaca | gcattgggga | ctatgagatc | tttgacgagg | acaccaagac | aatccgcaac | 1200 |
| aacagctggc | tgtaccaact | agcgatggac | attggcaccc | cttaccagtt | taatgggtct | 1260 |
| ggctcaggga | gtgggaagg | tggtcccagc | aagaattctg | tctacatctc | ctcgttgtat | 1320 |
| ttcacaatga | ccagcctcac | cagtgtgggc | tttgggaaca | tcgccccatc | cacagacatt | 1380 |
| gagaagatct | ttgcagtggc | catcatgatg | attggctcac | ttctctatgc | caccatcttc | 1440 |
| gggaatgtga | cgactatttt | ccaacagatg | tatgccaaca | ccaacagata | ccatgagatg | 1500 |
| ctcaacagtg | ttcgggactt | cctgaagctc | taccaggtgc | caaaaggatt | gagtgagcga | 1560 |
| gtaatggatt | atattgtgtc | cacttggtcc | atgtccagag | gcattgacac | agagaaggtc | 1620 |
| ctgcagatct | gccccaagga | catgagagcc | gacatctgcg | tgcacctgaa | ccgcaaggtg | 1680 |
| ttcaaggagc | acccggcctt | ccggctgccc | agtgatggct | gcctccgggc | actggccatg | 1740 |
| gagttccaga | cggtgcactg | tgccccaggg | gacctcatct | accatgcagg | agagagcgtt | 1800 |
| gacagcctct | gctttgtggt | ttctggctcc | ctggaggtga | tccaagatga | tgaggtggtg | 1860 |
| gccattctag | gaaaaggaga | cgtgtttgga | gatgtgttct | ggaaggaagc | cacccttgcc | 1920 |
| cagtcctgtg | ccaatgttag | ggccttgacc | tactgtgatc | tgcatgtgat | caagcgggat | 1980 |
| gccctgcaga | aagtgctgga | attctacacg | gccttctccc | attccttctc | ccggaacctg | 2040 |

```
attctgacgt acaacttgag gaagaggatt gtgttccgga agatcagcga tgtgaaacgt    2100
gaagaggaag aacgcatgaa acgaaagaat gaggcccccc tgatcttgcc cccggaccac    2160
cctgtccggc gcctcttcca gagattccga cagcagaaag aggccaggct ggcagctgag    2220
agagggggcc gggacctgga tgacctagat gtggagaagg gcaatgtcct tacagagcat    2280
gcctccgcca accacagcct cgtgaaggcc agcgtggtca ccgtgcgtga gagtcctgcc    2340
acgcccgtat ccttccaggc agcctccacc tccggggtgc cagaccacgc aaagctacag    2400
gcgccagggt ccgagtgcct gggccccaag ggggcgggg gcgattgtgc caagcgcaaa    2460
agctgggccc gcttcaaaga tgcttgcggg aagagtgagg actggaacaa ggtgtccaag    2520
gctgagtcga tggagacact tcccgagagg acaaaagcgt caggcgaggc cacactgaag    2580
aagacagact cgtgtgacag tggcatcacc aagagcgact tgcgcctgga caacgtgggt    2640
gaggccagga gtccccagga tcggagtccc atcctggcag aggtcaagca ttcgttctac    2700
cccatccctg agcagacgct gcaggccaca gtcctggagg tgaggcacga gctgaaggag    2760
gacatcaagg cctaaaacgc caaaatgacc aatattgaga aacagctctc tgagatactc    2820
aggatattaa cttccagaag atcctctcag tctcctcagg agttgtttga aatatcgagg    2880
ccacagtccc cagaatcaga gagagacatt tttggagcca gctgagaggt ctatttaaaa    2940
aaaaagtcag agacagatac ctccaaccct gccgtcacca ccaccctac cacccggaat    3000 tc                                                                   3002

<210> SEQ ID NO 2
<211> LENGTH: 3083
<212> TYPE: DNA
<213> ORGANISM: Homo sapiens

<400> SEQUENCE: 2
aattccgggc ccgccggacc ccgagctgct gggaggatga ccatggctgg gggcaggagg      60
ggactagtgg cccctcaaaa cacgtttctg gagaatattg ttcggcggtc caatgatact     120
aattttgtgt tggggaatgc tcagatagtg gactggccta ttgtgtacag caatgatgga     180
ttttgcaagc tgtctggcta tcacagggca gaagtgatgc aaaaaagcag cacctgcagt     240
tttatgtatg gggagctgac tgataaagac acgattgaaa aagtgcggca aacatttgag     300
aactatgaga tgaattcctt tgaaattctg atgtacaaga agaacaggac acctgtgtgg     360
ttctttgtga aaattgctcc aattcgaaac gaacaggata agtggttttt atttctttgc     420
actttcagtg acataacagc tttcaaacag ccaattgagg atgattcatg taaaggctgg     480
gggaagtttg ctcggctgac aagagcactg acaagcagca ggggtgtcct gcagcagctg     540
gctccaagcg tgcaaaaagg cgagaatgtc cacaagcact cccgcctggc agaggtccta     600
cagctgggct cagacatcct tccccagtac aagcaagagg caccaaagac tcccctcac     660 atcatcttac attattgtgt ttttaagacc acgtgggatt ggatcatctt gatcttgacc     720
ttctatacag ccatcttggt cccttataat gtctccttca aaaccaggca gaataatgtg     780
gcctggctgg ttgttgatag catcgtggat gttatctttt ggtggacat tgtgctcaat     840 tttcatacca cctttgttgg accagcaggg gaggtgattt ctgaccccaa acttatccgc     900
atgaactacc tgaagacgtg gttgtgatt gaccttctgt cctgtttgcc atatgatgtc     960
atcaacgctt tgagaacgt ggatgaggtt agtgcccttta tgggtgatcc agggaagatt    1020
ggttttgctg atcagattcc accaccactg gaggggagag agagtcaggg catcagcagc    1080
```

```
ctgttcagct ctctaaaagt tgtccggctg ctccgtcttg ggcgagtggc ccgtaagctg    1140
gaccactaca ttgaatatgg agctgctgtg ctggtcctgc tggtgtgtgt gtttgggctg    1200
gctgcacact ggatggcctg catctggtac agcattgggg actatgagat ctttgacgag    1260
gacaccaaga caatccgcaa caacagctgg ctgtaccaac tagcgatgga cattggcacc    1320
ccttaccagt ttaatgggtc tggctcaggg aagtgggaag gtggtcccag caagaattct    1380
gtctacatct cctcgttgta tttcacaatg accagcctca ccagtgtggg ctttgggaac    1440
atcgccccat ccacagacat tgagaagatc tttgcagtgg ccatcatgat gattggctca    1500
cttctctatg ccaccatctt cgggaatgtg acgactattt ccaacagat gtatgccaac    1560 accaacagat accatgagat gctcaacagt gttcgggact tcctgaagct ctaccaggtg    1620
ccaaaaggat tgagtgagcg agtaatggat tatattgtgt ccacttggtc catgtccaga    1680
ggcattgaca cagagaaggt cctgcagatc tgccccaagg acatgagagc cgacatctgc    1740
gtgcacctga accgcaaggt gttcaaggag caccccggcct tccggctggc cagtgatggc    1800
tgcctccggg cactggccat ggagttccag acggtgcact gtgccccagg ggacctcatc    1860
taccatgcag agagagcgt tgacagcctc tgctttgtgg tttctggctc cctggaggtg    1920
atccaagatg atgaggtggt ggccattcta ggaaaaggag acgtgtttgg agatgtgttc    1980
tggaaggaag ccaccctgc ccagtcctgt gccaatgtta gggccttgac ctactgtgat    2040
ctgcatgtga tcaagcggga tgccctgcag aaagtgctgg aattctacac ggccttctcc    2100
cattccttct cccggaacct gattctgacg tacaacttga ggaagaggat tgtgttccgg    2160
aagatcagcg atgtgaaacg tgaagaggaa gaacgcatga acgaaagaa tgaggccccc    2220 ctgatcttgc ccccggacca ccctgtccgg cgcctcttcc agagattccg acagcagaaa    2280
gaggccaggc tggcagctga gagggggc cgggacctgg atgacctaga tgtggagaag    2340
ggcaatgtcc ttacagagca tgcctccgcc aaccacagcc tcgtgaaggc cagcgtggtc    2400
accgtgcgtg agagtcctgc cacgcccgta tccttccagg cagcctccac ctccggggtg    2460
ccagaccacg caaagctaca ggcgccaggt tccgagtgcc tgggccccaa gggggggggg    2520
ggcgattgtg ccaagcgcaa aagctgggcc cgcttcaaag atgcttgcgg gaagagtgag    2580
gactggaaca aggtgtccaa ggctgagtcg atggagacac ttcccgagag acaaaaagcg    2640
tcaggcgagg ccacactgaa gaagacagac tcgtgtgaca gtggcatcac caagagcgac    2700
ttgcgcctgg acaacgtggg tgaggccagg agtccccagg atcggagtcc catcctggca    2760
gaggtcaagc attcgttcta ccccatccct gagcagacgc tgcaggccac agtcctggag    2820
gtgaggcacg agctgaagga ggacatcaag gccttaaacg ccaaaatgac caatattgag    2880
aaacagctct ctgagatact caggatatta acttccagaa gatcctctca gtctcctcag    2940
gagttgtttg aaatatcgag gccacagtcc ccagaatcag agagagacat ttttggagcc    3000
agctgagagg tctatttaaa aaaaagtca gagacagata cctccaaccc tgccgtcacc    3060
accaccccta ccacccggaa ttc                                            3083
```

<210> SEQ ID NO 3
<211> LENGTH: 962
<212> TYPE: PRT
<213> ORGANISM: Homo sapiens

<400> SEQUENCE: 3

Met Thr Met Ala Gly Gly Arg Arg Gly Leu Val Ala Pro Gln Asn Thr
 1               5                  10                  15

```
-continued

Phe Leu Glu Asn Ile Val Arg Arg Ser Asn Asp Thr Asn Phe Val Leu
             20                  25                  30

Gly Asn Ala Gln Ile Val Asp Trp Pro Ile Val Tyr Ser Asn Asp Gly
             35                  40                  45

Phe Cys Lys Leu Ser Gly Tyr His Arg Ala Glu Val Met Gln Lys Ser
             50                  55                  60

Ser Thr Cys Ser Phe Met Tyr Gly Glu Leu Thr Asp Lys Asp Thr Ile
 65                  70                  75                  80

Glu Lys Val Arg Gln Thr Phe Glu Asn Tyr Glu Met Asn Ser Phe Glu
                 85                  90                  95

Ile Leu Met Tyr Lys Lys Asn Arg Thr Pro Val Trp Phe Phe Val Lys
            100                 105                 110

Ile Ala Pro Ile Arg Asn Glu Gln Asp Lys Val Val Leu Phe Leu Cys
            115                 120                 125

Thr Phe Ser Asp Ile Thr Ala Phe Lys Gln Pro Ile Glu Asp Asp Ser
            130                 135                 140

Cys Lys Gly Trp Gly Lys Phe Ala Arg Leu Thr Arg Ala Leu Thr Ser
145                 150                 155                 160

Ser Arg Gly Val Leu Gln Gln Leu Ala Pro Ser Val Gln Lys Gly Glu
                165                 170                 175

Asn Val His Lys His Ser Arg Leu Ala Glu Val Leu Gln Leu Gly Ser
            180                 185                 190

Asp Ile Leu Pro Gln Tyr Lys Gln Glu Ala Pro Lys Thr Pro Pro His
            195                 200                 205

Ile Ile Leu His Tyr Cys Val Phe Lys Thr Thr Trp Asp Trp Ile Ile
            210                 215                 220

Leu Ile Leu Thr Phe Tyr Thr Ala Ile Leu Val Pro Tyr Asn Val Ser
225                 230                 235                 240

Phe Lys Thr Arg Gln Asn Asn Val Ala Trp Leu Val Val Asp Ser Ile
                245                 250                 255

Val Asp Val Ile Phe Leu Val Asp Ile Val Leu Asn Phe His Thr Thr
            260                 265                 270

Phe Val Gly Pro Ala Gly Glu Val Ile Ser Asp Pro Lys Leu Ile Arg
            275                 280                 285

Met Asn Tyr Leu Lys Thr Trp Phe Val Ile Asp Leu Leu Ser Cys Leu
290                 295                 300

Pro Tyr Asp Val Ile Asn Ala Phe Glu Asn Val Asp Glu Gly Ile Ser
305                 310                 315                 320

Ser Leu Phe Ser Ser Leu Lys Val Val Arg Leu Leu Arg Leu Gly Arg
                325                 330                 335

Val Ala Arg Lys Leu Asp His Tyr Ile Glu Tyr Gly Ala Ala Val Leu
            340                 345                 350

Val Leu Leu Val Cys Val Phe Gly Leu Ala Ala His Trp Met Ala Cys
            355                 360                 365

Ile Trp Tyr Ser Ile Gly Asp Tyr Glu Ile Phe Asp Glu Asp Thr Lys
            370                 375                 380

Thr Ile Arg Asn Asn Ser Trp Leu Tyr Gln Leu Ala Met Asp Ile Gly
385                 390                 395                 400

Thr Pro Tyr Gln Phe Asn Gly Ser Gly Ser Gly Lys Trp Glu Gly Gly
                405                 410                 415

Pro Ser Lys Asn Ser Val Tyr Ile Ser Ser Leu Tyr Phe Thr Met Thr
            420                 425                 430

Ser Leu Thr Ser Val Gly Phe Gly Asn Ile Ala Pro Ser Thr Asp Ile
```

-continued

```
            435                 440                 445
Glu Lys Ile Phe Ala Val Ala Ile Met Met Ile Gly Ser Leu Leu Tyr
            450                 455                 460
Ala Thr Ile Phe Gly Asn Val Thr Thr Ile Phe Gln Gln Met Tyr Ala
465                 470                 475                 480
Asn Thr Asn Arg Tyr His Glu Met Leu Asn Ser Val Arg Asp Phe Leu
                        485                 490                 495
Lys Leu Tyr Gln Val Pro Lys Gly Leu Ser Glu Arg Val Met Asp Tyr
            500                 505                 510
Ile Val Ser Thr Trp Ser Met Ser Arg Gly Ile Asp Thr Glu Lys Val
            515                 520                 525
Leu Gln Ile Cys Pro Lys Asp Met Arg Ala Asp Ile Cys Val His Leu
            530                 535                 540
Asn Arg Lys Val Phe Lys Glu His Pro Ala Phe Arg Leu Ala Ser Asp
545                 550                 555                 560
Gly Cys Leu Arg Ala Leu Ala Met Glu Phe Gln Thr Val His Cys Ala
                        565                 570                 575
Pro Gly Asp Leu Ile Tyr His Ala Gly Glu Ser Val Asp Ser Leu Cys
            580                 585                 590
Phe Val Val Ser Gly Ser Leu Glu Val Ile Gln Asp Asp Glu Val Val
            595                 600                 605
Ala Ile Leu Gly Lys Gly Asp Val Phe Gly Asp Val Phe Trp Lys Glu
            610                 615                 620
Ala Thr Leu Ala Gln Ser Cys Ala Asn Val Arg Ala Leu Thr Tyr Cys
625                 630                 635                 640
Asp Leu His Val Ile Lys Arg Asp Ala Leu Gln Lys Val Leu Glu Phe
                        645                 650                 655
Tyr Thr Ala Phe Ser His Ser Phe Ser Arg Asn Leu Ile Leu Thr Tyr
            660                 665                 670
Asn Leu Arg Lys Arg Ile Val Phe Arg Lys Ile Ser Asp Val Lys Arg
            675                 680                 685
Glu Glu Glu Glu Arg Met Lys Arg Lys Asn Glu Ala Pro Leu Ile Leu
            690                 695                 700
Pro Pro Asp His Pro Val Arg Arg Leu Phe Gln Arg Phe Arg Gln Gln
705                 710                 715                 720
Lys Glu Ala Arg Leu Ala Ala Glu Arg Gly Gly Arg Asp Leu Asp Asp
                        725                 730                 735
Leu Asp Val Glu Lys Gly Asn Val Leu Thr Glu His Ala Ser Ala Asn
            740                 745                 750
His Ser Leu Val Lys Ala Ser Val Val Thr Val Arg Glu Ser Pro Ala
            755                 760                 765
Thr Pro Val Ser Phe Gln Ala Ala Ser Thr Ser Gly Val Pro Asp His
770                 775                 780
Ala Lys Leu Gln Ala Pro Gly Ser Glu Cys Leu Gly Pro Lys Gly Gly
785                 790                 795                 800
Gly Gly Asp Cys Ala Lys Arg Lys Ser Trp Ala Arg Phe Lys Asp Ala
                        805                 810                 815
Cys Gly Lys Ser Glu Asp Trp Asn Lys Val Ser Lys Ala Glu Ser Met
                        820                 825                 830
Glu Thr Leu Pro Glu Arg Thr Lys Ala Ser Gly Glu Ala Thr Leu Lys
            835                 840                 845
Lys Thr Asp Ser Cys Asp Ser Gly Ile Thr Lys Ser Asp Leu Arg Leu
            850                 855                 860
```

```
Asp Asn Val Gly Glu Ala Arg Ser Pro Gln Asp Arg Ser Pro Ile Leu
865                 870                 875                 880

Ala Glu Val Lys His Ser Phe Tyr Pro Ile Pro Glu Gln Thr Leu Gln
                885                 890                 895

Ala Thr Val Leu Glu Val Arg His Glu Leu Lys Glu Asp Ile Lys Ala
                900                 905                 910

Leu Asn Ala Lys Met Thr Asn Ile Glu Lys Gln Leu Ser Glu Ile Leu
                915                 920                 925

Arg Ile Leu Thr Ser Arg Arg Ser Ser Gln Ser Pro Gln Glu Leu Phe
            930                 935                 940

Glu Ile Ser Arg Pro Gln Ser Pro Glu Ser Glu Arg Asp Ile Phe Gly
945                 950                 955                 960

Ala Ser

<210> SEQ ID NO 4
<211> LENGTH: 989
<212> TYPE: PRT
<213> ORGANISM: Homo sapiens

<400> SEQUENCE: 4

Met Thr Met Ala Gly Gly Arg Arg Gly Leu Val Ala Pro Gln Asn Thr
  1               5                  10                  15

Phe Leu Glu Asn Ile Val Arg Arg Ser Asn Asp Thr Asn Phe Val Leu
             20                  25                  30

Gly Asn Ala Gln Ile Val Asp Trp Pro Ile Val Tyr Ser Asn Asp Gly
         35                  40                  45

Phe Cys Lys Leu Ser Gly Tyr His Arg Ala Glu Val Met Gln Lys Ser
     50                  55                  60

Ser Thr Cys Ser Phe Met Tyr Gly Glu Leu Thr Asp Lys Asp Thr Ile
 65                  70                  75                  80

Glu Lys Val Arg Gln Thr Phe Glu Asn Tyr Glu Met Asn Ser Phe Glu
                 85                  90                  95

Ile Leu Met Tyr Lys Lys Asn Arg Thr Pro Val Trp Phe Phe Val Lys
            100                 105                 110

Ile Ala Pro Ile Arg Asn Glu Gln Asp Lys Val Val Leu Phe Leu Cys
        115                 120                 125

Thr Phe Ser Asp Ile Thr Ala Phe Lys Gln Pro Ile Glu Asp Asp Ser
130                 135                 140

Cys Lys Gly Trp Gly Lys Phe Ala Arg Leu Thr Arg Ala Leu Thr Ser
145                 150                 155                 160

Ser Arg Gly Val Leu Gln Gln Leu Ala Pro Ser Val Gln Lys Gly Glu
                165                 170                 175

Asn Val His Lys His Ser Arg Leu Ala Glu Val Leu Gln Leu Gly Ser
            180                 185                 190

Asp Ile Leu Pro Gln Tyr Lys Gln Glu Ala Pro Lys Thr Pro Pro His
        195                 200                 205

Ile Ile Leu His Tyr Cys Val Phe Lys Thr Thr Trp Asp Trp Ile Ile
    210                 215                 220

Leu Ile Leu Thr Phe Tyr Thr Ala Ile Leu Val Pro Tyr Asn Val Ser
225                 230                 235                 240

Phe Lys Thr Arg Gln Asn Asn Val Ala Trp Leu Val Val Asp Ser Ile
                245                 250                 255

Val Asp Val Ile Phe Leu Val Asp Ile Val Leu Asn Phe His Thr Thr
            260                 265                 270
```

```
Phe Val Gly Pro Ala Gly Glu Val Ile Ser Asp Pro Lys Leu Ile Arg
        275                 280                 285

Met Asn Tyr Leu Lys Thr Trp Phe Val Ile Asp Leu Leu Ser Cys Leu
        290                 295                 300

Pro Tyr Asp Val Ile Asn Ala Phe Glu Asn Val Asp Glu Val Ser Ala
305                 310                 315                 320

Phe Met Gly Asp Pro Gly Lys Ile Gly Phe Ala Asp Gln Ile Pro Pro
                    325                 330                 335

Pro Leu Glu Gly Arg Glu Ser Gln Gly Ile Ser Ser Leu Phe Ser Ser
                340                 345                 350

Leu Lys Val Val Arg Leu Leu Arg Leu Gly Arg Val Ala Arg Lys Leu
            355                 360                 365

Asp His Tyr Ile Glu Tyr Gly Ala Ala Val Leu Val Leu Leu Val Cys
        370                 375                 380

Val Phe Gly Leu Ala Ala His Trp Met Ala Cys Ile Trp Tyr Ser Ile
385                 390                 395                 400

Gly Asp Tyr Glu Ile Phe Asp Glu Asp Thr Lys Thr Ile Arg Asn Asn
                    405                 410                 415

Ser Trp Leu Tyr Gln Leu Ala Met Asp Ile Gly Thr Pro Tyr Gln Phe
                420                 425                 430

Asn Gly Ser Gly Ser Gly Lys Trp Glu Gly Gly Pro Ser Lys Asn Ser
            435                 440                 445

Val Tyr Ile Ser Ser Leu Tyr Phe Thr Met Thr Ser Leu Thr Ser Val
        450                 455                 460

Gly Phe Gly Asn Ile Ala Pro Ser Thr Asp Ile Glu Lys Ile Phe Ala
465                 470                 475                 480

Val Ala Ile Met Met Ile Gly Ser Leu Leu Tyr Ala Thr Ile Phe Gly
                    485                 490                 495

Asn Val Thr Thr Ile Phe Gln Gln Met Tyr Ala Asn Thr Asn Arg Tyr
                500                 505                 510

His Glu Met Leu Asn Ser Val Arg Asp Phe Leu Lys Leu Tyr Gln Val
            515                 520                 525

Pro Lys Gly Leu Ser Glu Arg Val Met Asp Tyr Ile Val Ser Thr Trp
        530                 535                 540

Ser Met Ser Arg Gly Ile Asp Thr Glu Lys Val Leu Gln Ile Cys Pro
545                 550                 555                 560

Lys Asp Met Arg Ala Asp Ile Cys Val His Leu Asn Arg Lys Val Phe
                    565                 570                 575

Lys Glu His Pro Ala Phe Arg Leu Ala Ser Asp Gly Cys Leu Arg Ala
                580                 585                 590

Leu Ala Met Glu Phe Gln Thr Val His Cys Ala Pro Gly Asp Leu Ile
            595                 600                 605

Tyr His Ala Gly Glu Ser Val Asp Ser Leu Cys Phe Val Val Ser Gly
        610                 615                 620

Ser Leu Glu Val Ile Gln Asp Asp Glu Val Val Ala Ile Leu Gly Lys
625                 630                 635                 640

Gly Asp Val Phe Gly Asp Val Phe Trp Lys Glu Ala Thr Leu Ala Gln
                    645                 650                 655

Ser Cys Ala Asn Val Arg Ala Leu Thr Tyr Cys Asp Leu His Val Ile
                660                 665                 670

Lys Arg Asp Ala Leu Gln Lys Val Leu Glu Phe Tyr Thr Ala Phe Ser
            675                 680                 685
```

-continued

```
His Ser Phe Ser Arg Asn Leu Ile Leu Thr Tyr Asn Leu Arg Lys Arg
    690                 695                 700
Ile Val Phe Arg Lys Ile Ser Asp Val Lys Arg Glu Glu Glu Glu Arg
705                 710                 715                 720
Met Lys Arg Lys Asn Glu Ala Pro Leu Ile Leu Pro Pro Asp His Pro
                725                 730                 735
Val Arg Arg Leu Phe Gln Arg Phe Arg Gln Gln Lys Glu Ala Arg Leu
            740                 745                 750
Ala Ala Glu Arg Gly Gly Arg Asp Leu Asp Asp Leu Asp Val Glu Lys
        755                 760                 765
Gly Asn Val Leu Thr Glu His Ala Ser Ala Asn His Ser Leu Val Lys
    770                 775                 780
Ala Ser Val Val Thr Val Arg Glu Ser Pro Ala Thr Pro Val Ser Phe
785                 790                 795                 800
Gln Ala Ala Ser Thr Ser Gly Val Pro Asp His Ala Lys Leu Gln Ala
                805                 810                 815
Pro Gly Ser Glu Cys Leu Gly Pro Lys Gly Gly Gly Asp Cys Ala
            820                 825                 830
Lys Arg Lys Ser Trp Ala Arg Phe Lys Asp Ala Cys Gly Lys Ser Glu
        835                 840                 845
Asp Trp Asn Lys Val Ser Lys Ala Glu Ser Met Glu Thr Leu Pro Glu
    850                 855                 860
Arg Thr Lys Ala Ser Gly Glu Ala Thr Leu Lys Lys Thr Asp Ser Cys
865                 870                 875                 880
Asp Ser Gly Ile Thr Lys Ser Asp Leu Arg Leu Asp Asn Val Gly Glu
                885                 890                 895
Ala Arg Ser Pro Gln Asp Arg Ser Pro Ile Leu Ala Glu Val Lys His
            900                 905                 910
Ser Phe Tyr Pro Ile Pro Glu Gln Thr Leu Gln Ala Thr Val Leu Glu
        915                 920                 925
Val Arg His Glu Leu Lys Glu Asp Ile Lys Ala Leu Asn Ala Lys Met
    930                 935                 940
Thr Asn Ile Glu Lys Gln Leu Ser Glu Ile Leu Arg Ile Leu Thr Ser
945                 950                 955                 960
Arg Arg Ser Ser Gln Ser Pro Gln Glu Leu Phe Glu Ile Ser Arg Pro
                965                 970                 975
Gln Ser Pro Glu Ser Glu Arg Asp Ile Phe Gly Ala Ser
            980                 985
```

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 5
ccaaacacac acaccagc                                                    18

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:
      Synthetic DNA -continued

```
<400> SEQUENCE: 6
cgtggatgtt atcttttttgg                                              20

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 7
gggaggatga ccatggct                                                 18

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:
      Synthetic DNA
<221> NAME/KEY: modified_base
<222> LOCATION: (15)
<223> OTHER INFORMATION: a, t, c or g

<400> SEQUENCE: 8
cagaayaayg tggcntggct                                               20

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 9
tcactraaga tctatartc                                                19

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 10
cgcatgaact acctgaagac g                                             21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 11
tctgtggatg gggcgatgtt c                                             21

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence:
```

Synthetic DNA

<400> SEQUENCE: 12
gggaggatga ccatggct                                                     18

<210> SEQ ID NO 13
<211> LENGTH: 2886
<212> TYPE: DNA
<213> ORGANISM: Homo sapiens

<400> SEQUENCE: 13

| | | | | | |
|---|---|---|---|---|---|
| atgaccatgg | ctgggggcag | gaggggacta | gtggcccctc | aaaacacgtt | tctggagaat | 60 |
| attgttcggc | ggtccaatga | tactaatttt | gtgttgggga | atgctcagat | agtggactgg | 120 |
| cctattgtgt | acagcaatga | tggattttgc | aagctgtctg | gctatcacag | ggcagaagtg | 180 |
| atgcaaaaaa | gcagcacctg | cagttttatg | tatggggagc | tgactgataa | agacacgatt | 240 |
| gaaaaagtgc | ggcaaacatt | tgagaactat | gagatgaatt | cctttgaaat | tctgatgtac | 300 |
| aagaagaaca | ggacacctgt | gtggttcttt | gtgaaaattg | ctccaattcg | aaacgaacag | 360 |
| gataaagtgg | ttttatttct | ttgcactttc | agtgacataa | cagctttcaa | acagccaatt | 420 |
| gaggatgatt | catgtaaagg | ctgggggaag | tttgctcggc | tgacaagagc | actgacaagc | 480 |
| agcagggtg | tcctgcagca | gctggctcca | agcgtgcaaa | aaggcgagaa | tgtccacaag | 540 |
| cactcccgcc | tggcagaggt | cctacagctg | ggctcagaca | tccttcccca | gtacaagcaa | 600 |
| gaggcaccaa | agactccccc | tcacatcatc | ttacattatt | gtgttttaa | gaccacgtgg | 660 |
| gattggatca | tcttgatctt | gaccttctat | acagccatct | tggtccctta | taatgtctcc | 720 |
| ttcaaaacca | ggcagaataa | tgtggcctgg | ctggttgttg | atagcatcgt | ggatgttatc | 780 |
| tttttggtgg | acattgtgct | caattttcat | accacctttg | ttggaccagc | aggggaggtg | 840 |
| atttctgacc | ccaaacttat | ccgcatgaac | tacctgaaga | cgtggtttgt | gattgacctt | 900 |
| ctgtcctgtt | tgccatatga | tgtcatcaac | gcttttgaga | cgtggatga | gggcatcagc | 960 |
| agcctgttca | gctctctaaa | agttgtccgg | ctgctccgtc | ttgggcgagt | ggcccgtaag | 1020 |
| ctggaccact | acattgaata | tggagctgct | gtgctggtcc | tgctggtgtg | tgtgtttggg | 1080 |
| ctggctgcac | actggatggc | ctgcatctgg | tacagcattg | gggactatga | gatctttgac | 1140 |
| gaggacacca | agacaatccg | caacaacagc | tggctgtacc | aactagcgat | ggacattggc | 1200 |
| acccctacc | agtttaatgg | gtctggctca | gggaagtggg | aaggtggtcc | cagcaagaat | 1260 |
| tctgtctaca | tctcctcgtt | gtatttcaca | atgaccagcc | tcaccagtgt | gggctttggg | 1320 |
| aacatcgccc | catccacaga | cattgagaag | atctttgcag | tggccatcat | gatgattggc | 1380 |
| tcacttctct | atgccaccat | cttcgggaat | gtgacgacta | ttttccaaca | gatgtatgcc | 1440 |
| aacaccaaca | gataccatga | gatgctcaac | agtgttcggg | acttcctgaa | gctctaccag | 1500 |
| gtgccaaaag | gattgagtga | gcgagtaatg | gattatattg | tgtccacttg | gtccatgtcc | 1560 |
| agaggcattg | acacagagaa | ggtcctgcag | atctgcccca | aggacatgag | agccgacatc | 1620 |
| tgcgtgcacc | tgaaccgcaa | ggtgttcaag | gagcacccgg | ccttccggct | ggccagtgat | 1680 |
| ggctgcctcc | gggcactggc | catggagttc | cagacggtgc | actgtgcccc | aggggacctc | 1740 |
| atctaccatg | caggagagag | cgttgacagc | ctctgctttg | tggtttctgg | ctccctggag | 1800 |
| gtgatccaag | atgatgaggt | ggtggccatt | ctaggaaaag | gagacgtgtt | tggagatgtg | 1860 |
| ttctggaagg | aagccaccct | tgcccagtcc | tgtgccaatg | ttagggcctt | gacctactgt | 1920 |
| gatctgcatg | tgatcaagcg | ggatgccctg | cagaaagtgc | tggaattcta | cacggccttc | 1980 |

-continued

| | |
|---|---|
| tcccattcct tctcccggaa cctgattctg acgtacaact tgaggaagag gattgtgttc | 2040 |
| cggaagatca gcgatgtgaa acgtgaagag gaagaacgca tgaaacgaaa gaatgaggcc | 2100 |
| cccctgatct tgcccccgga ccaccctgtc cggcgcctct tccagagatt ccgacagcag | 2160 |
| aaagaggcca ggctggcagc tgagagaggg ggccgggacc tggatgacct agatgtggag | 2220 |
| aagggcaatg tccttacaga gcatgcctcc gccaaccaca gcctcgtgaa ggccagcgtg | 2280 |
| gtcaccgtgc gtgagagtcc tgccacgccc gtatccttcc aggcagcctc cacctccggg | 2340 |
| gtgccagacc acgcaaagct acaggcgcca gggtccgagt gcctgggccc caaggggggc | 2400 |
| gggggcgatt gtgccaagcg caaaagctgg gcccgcttca agatgcttg cgggaagagt | 2460 |
| gaggactgga acaaggtgtc caaggctgag tcgatggaga cacttcccga gaggacaaaa | 2520 |
| gcgtcaggcg aggccacact gaagaagaca gactcgtgtg acagtggcat caccaagagc | 2580 |
| gacttgcgcc tggacaacgt gggtgaggcc aggagtcccc aggatcggag tcccatcctg | 2640 |
| gcagaggtca gcattcgtt ctaccccatc cctgagcaga cgctgcaggc cacagtcctg | 2700 |
| gaggtgaggc acgagctgaa ggaggacatc aaggccttaa acgccaaaat gaccaatatt | 2760 |
| gagaaacagc tctctgagat actcaggata ttaacttcca gaagatcctc tcagtctcct | 2820 |
| caggagttgt tgaaatatc gaggccacag tccccagaat cagagagaga cattttttgga | 2880 |
| gccagc | 2886 |

<210> SEQ ID NO 14
<211> LENGTH: 2967
<212> TYPE: DNA
<213> ORGANISM: Homo sapiens

<400> SEQUENCE: 14

| | |
|---|---|
| atgaccatgg ctgggggcag gaggggacta gtggcccctc aaaacacgtt tctggagaat | 60 |
| attgttcggc ggtccaatga tactaatttt gtgttgggga atgctcagat agtggactgg | 120 |
| cctattgtgt acagcaatga tggatttgc aagctgtctg gctatacag gcagaagtg | 180 |
| atgcaaaaaa gcagcacctg cagttttatg tatggggagc tgactgataa agacacgatt | 240 |
| gaaaaagtgc ggcaaacatt tgagaactat gagatgaatt cctttgaaat tctgatgtac | 300 |
| aagaagaaca ggacacctgt gtggttcttt gtgaaaattg ctccaattcg aaacgaacag | 360 |
| gataaagtgg ttttatttct ttgcactttc agtgacataa cagctttcaa acagccaatt | 420 |
| gaggatgatt catgtaaagg ctgggggaag tttgctcggc tgacaagagc actgacaagc | 480 |
| agcagggtg tcctgcagca gctggctcca agcgtgcaaa aaggcgagaa tgtccacaag | 540 |
| cactcccgcc tggcagaggt cctacagctg ggctcagaca tccttcccca gtacaagcaa | 600 |
| gaggcaccaa agactccccc tcacatcatc ttacattatt gtgtttttaa gaccacgtgg | 660 |
| gattggatca tcttgatctt gaccttctat acagccatct tggtccctta taatgtctcc | 720 |
| ttcaaaacca ggcagaataa tgtggcctgg ctggttgttg atagcatcgt ggatgttatc | 780 |
| tttttggtgg acattgtgct caattttcat accaccttg ttggaccagc aggggaggtg | 840 |
| atttctgacc ccaaacttat ccgcatgaac tacctgaaga cgtggtttgt gattgacctt | 900 |
| ctgtcctgtt tgccatatga tgtcatcaac gcttttgaga acgtggatga ggttagtgcc | 960 |
| tttatgggtg atccagggaa gattggtttt gctgatcaga ttccaccacc actggagggg | 1020 |
| agagagagtc agggcatcag cagcctgttc agctctctaa aagttgtccg gctgctccgt | 1080 |
| cttgggcgag tggcccgtaa gctggaccac tacattgaat atgagctgc tgtgctggtc | 1140 |

```
ctgctggtgt gtgtgtttgg gctggctgca cactggatgg cctgcatctg gtacagcatt    1200
ggggactatg agatctttga cgaggacacc aagacaatcc gcaacaacag ctggctgtac    1260
caactagcga tggacattgg caccccttac cagtttaatg ggtctggctc agggaagtgg    1320
gaaggtggtc ccagcaagaa ttctgtctac atctcctcgt tgtatttcac aatgaccagc    1380
ctcaccagtg tgggctttgg gaacatcgcc ccatccacag acattgagaa gatctttgca    1440
gtggccatca tgatgattgg ctcacttctc tatgccacca tcttcgggaa tgtgacgact    1500
attttccaac agatgtatgc caacaccaac agataccatg agatgctcaa cagtgttcgg    1560
gacttcctga gctctacca ggtgccaaaa ggattgagtg agcgagtaat ggattatatt    1620
gtgtccactt ggtccatgtc cagaggcatt gacacagaga aggtcctgca gatctgcccc    1680
aaggacatga gagccgacat ctgcgtgcac ctgaaccgca aggtgttcaa ggagcacccg    1740
gccttccggc tggccagtga tggctgcctc cgggcactgg ccatggagtt ccagacggtg    1800
cactgtgccc caggggacct catctaccat gcaggagaga gcgttgacag cctctgcttt    1860
gtggtttctg gctccctgga ggtgatccaa gatgatgagg tggtggccat tctaggaaaa    1920
ggagacgtgt ttgagatgt gttctggaag gaagccaccc ttgcccagtc ctgtgccaat    1980
gttagggcct tgacctactg tgatctgcat gtgatcaagc gggatgccct gcagaaagtg    2040
ctggaattct acacggcctt ctcccattcc ttctcccgga acctgattct gacgtacaac    2100
ttgaggaaga ggattgtgtt ccggaagatc agcgatgtga acgtgaaga ggaagaacgc    2160 atgaaacgaa agaatgaggc cccctgatc ttgcccccgg accaccctgt ccggcgcctc    2220
ttccagagat tccgacagca gaaagaggcc aggctggcag ctgagagagg gggccgggac    2280
ctggatgacc tagatgtgga gaagggcaat gtccttacag agcatgcctc cgccaaccac    2340
agcctcgtga aggccagcgt ggtcaccgtg cgtgagagtc ctgccacgcc cgtatccttc    2400
caggcagcct ccacctccgg ggtgccagac cacgcaaagc tacaggcgcc agggtccgag    2460
tgcctgggcc ccaaggggg cggggcgat tgtgccaagc gcaaaagctg ggcccgcttc    2520
aaagatgctt gcgggaagag tgaggactgg aacaaggtgt ccaaggctga gtcgatggag    2580
acacttcccg agaggacaaa agcgtcaggc gaggccacac tgaagaagac agactcgtgt    2640
gacagtggca tcaccaagag cgacttgcgc ctggacaacg tgggtgaggc caggagtccc    2700
caggatcgga gtcccatcct ggcagaggtc aagcattcgt tctaccccat ccctgagcag    2760
acgctgcagg ccacagtcct ggaggtgagg cacgagctga aggaggacat caaggcctta    2820
aacgccaaaa tgaccaatat tgagaaacag ctctctgaga tactcaggat attaacttcc    2880
agaagatcct ctcagtctcc tcaggagttg tttgaaatat cgaggccaca gtccccagaa    2940
tcagagagag acattttttgg agccagc                                         2967
```

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Antisense
      phosphorothioate ODN

<400> SEQUENCE: 15

```
cagccatggt catcctccc                                                    19
```

<210> SEQ ID NO 16
<211> LENGTH: 19
<212> TYPE: DNA

```
<213> ORGANISM: Artificial Sequence
<220> FEATURE:
<223> OTHER INFORMATION: Description of Artificial Sequence: Synthetic
      scrambled sequence

<400> SEQUENCE: 16
gtcggtacca gtaggaggg                                                  19

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 17
tcagcccagc agaagcatta t                                               21

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 18
ctggcagcgt gtgagagc                                                   18

<210> SEQ ID NO 19
<211> LENGTH: 3041
<212> TYPE: DNA
<213> ORGANISM: Bovine sp.

<400> SEQUENCE: 19
gtgccgggac gcccccaga ccccgagctg ccggaggat gaccatggct gggggcagga        60
agggactggt ggccccgcaa aacacgtttc tggagaatat tgtccggcgg tccaatgata     120
ctaactttgt tttggggaat gcccagatag tggactggcc tatcgtgtac agcaatgatg     180
gattttgcaa gctgtctggc tatcacaggg cggaagtgat gcaaaaaagc agtacatgca     240
gttttatgta tggggagctg accgataaag ataccattga aaaagtgcgg caaaccttg     300 agaactatga gatgaattcc tttgaaattc tgatgtacaa gagaacagg acacctgtgt     360 ggttctttgt gaaaattgct ccaattcgaa cgaacagga taaagtggtt ttatttcttt     420
gcactttcag tgacataacc gctttcaaac agccgattga agatgattca tgtaaaggct     480
gggggaagtt cgctcggctg accagagcac tgacgagcag ccggggtgtc ctgcagcagc     540
tggctcccag cgtgcagaaa ggcgagaacg tccacaagca ctcccgtctg gccgaggttc     600
tgcagctggg ctcagacatc cttccccagt acaagcaaga ggcaccaaag actccccgc     660 acatcatctt acactactgc gttttttaaga ccacgtggga ctggatcatc ctgatcctaa     720
ccttctacac agccatcctg gttccttaca acgtctcctt taaaaccagg cagaacaacg     780
tggcctggct ggttgtggac agcatcgtgg atgtcatttt tttggtggac attgtgctga     840
attttcacac cacttttgtt ggaccgctg gggaggtgat ttctgacccc aaactcattc     900
gcatgaacta cctgaagacg tggtttgtga ttgaccttct gtcctgtttg ccctatgacg     960
tcatcaacgc ttttgagaac gtggatgagg gcatcagcag cctgttcagc tctctgaaag    1020
ttgtccggct gctccgcctg ggacgcgtgg cccggaagct ggaccactac atcgagtatg    1080
gagctgccgt gctggtcctg ctggtgtgtg tgttcgggct ggccgctcac tggatggcct    1140
```

```
gcatttggta cagcatcggg gactatgaga tcttcgacga ggacaccaag accatccgca   1200
acaacagctg gctctaccag ctggccatgg acattggcac cccttaccag tttaacgggt   1260
ctggctcagg gaagtgggaa gggggtccca gcaagaattc cgtctacatc tcctcgttgt   1320
atttcaccat gaccagcctc accagcgtgg gctttgggaa catcgccccg tccacagaca   1380
ttgagaagat ctttgccgtg gccatcatga tgattggctc cctcctctat gccaccatct   1440
ttgggaatgt gacgaccatt ttccaacaga tgtacgccaa caccaacagg taccatgaga   1500
tgctcaacag tgtccgggac ttcttgaagc tctaccaggt gcccaagggg ctgagcgagc   1560
gagtcatgga ttacatcgtg tccacctggt ccatgtccag aggcattgac acagagaagg   1620
tcctgcagat ctgccccaag gacatgagag cggacatctg cgtgcaccta aaccgcaagg   1680
tcttcaagga gcacccagcc tttcggctgg ccagcgacgg ctgcctgcgg gcactggcca   1740
tggagttcca gacggtgcac tgcgcccctg ggacctcat ctaccacgca ggggagagcg   1800
tcgacagcct gtgcttcgtg gtctccggct ccctggaggt gatccaggat gacgaggtgg   1860
tggccattct agggaaagga gacgtgtttg agacgtgtt ctggaaggaa gccacccttg   1920
cccagtcctg tgccaatgtg agggccttga cctactgtga cctccatgtg atcaagcggg   1980
acgccctgca gaaagtgctg gaattctaca cagccttctc ccactccttc tcccggaacc   2040
tcattctcac ctacaacttg aggaagcgga tcgtgttccg gaagatcagt gacgtgaaac   2100
gggaggagga ggagcgcatg aagcggaaga atgaggcccc cctgatcctg ccgcccgacc   2160
accccgtccg gcggctcttc cagaggttcc gccagcagaa ggaagccagg ctggccgcgg   2220
agaggggcgg gcgggacttg gacgacctgg acgtggagaa gggcagcgtc ctcaccgagc   2280
acagccacca cggcctggcg aaggccagcg tcgtcaccgt ccgagagagc cctgccacgc   2340
ccgtggcctt cccggcggcc gctgccccgg cggggctgga tcacgcccgg ctgcaggcgc   2400
ctggggccga gggcctgggc cccaaggccg gcggggccga ctgcgccaag cgcaagggct   2460
gggcccgctt caaggatgcc tgcgggcagg ctgaggactg gagcaaggtg tccaaggccg   2520
agtccatgga aacgctcccc gagaggacga aggccgccgg cgaggccaca ctcaagaaga   2580
cggactcgtg cgacagcggc atcaccaaga gcgacctgcg tctggacaac gtgggcgagg   2640
ccagaagccc ccaggaccgg agccccatct tggcggaggt caagcactcc ttctaccccca   2700 tccccgagca gacgctgcag gccgccgtcc tggaggtgaa gcacgagctc aaggaggaca   2760
tcaaggcctt gagcaccaag atgacgagca ttgagaaaca gctctctgag atactcagga   2820
tattaacctc cagaagatcc tctcagtcgc ctcaggagct atttgaaata tcgaggcccc   2880
agtccccaga gtcagagaga gacattttttg gcgcaagctg agaggtctgt tgtaaaaaaa   2940
aagaaaaaaa atccaagatg acaaaaacct accgtcctgc cctagacacc accacacaca   3000
cacctacatg accaacaacc ttcaaagtag gcttttccca a                      3041
```

<210> SEQ ID NO 20
<211> LENGTH: 3041
<212> TYPE: DNA
<213> ORGANISM: Rattus sp.

<400> SEQUENCE: 20

```
tgcggtgaga cacggcgccg gacgcccca gagcccagc agtagggagg atgaccatgg    60
ctggcggccg gcggggacta gtggccccgc agaacacatt tctggagaac atcgtgcggc   120
ggtccaacga cactaatttt gtgttgggga atgcccagat cgtggactgg cccatcgtgt   180
acagcaatga tggattctgc aagctgtctg gctaccaccg agcggaagtg atgcaaaaga   240
```

```
gtagcgcctg cagttttatg tatggagagc tgaccgacaa ggacacggtt gaaaaggttc    300
gccagacctt tgagaactac gagatgaact ccttcgaaat tctgatgtac aagaagaaca    360
ggacacctgt gtggttttt gtgaagatcg ctccaatcag gaacgaacag ataaagtgg     420 ttctgttcct ttgcactttc agtgacataa cggcattcaa gcagcccatt gaggacgact    480
cctgcaaagg ttgggggaag tttgctcgac tgacgagagc tctgacaagc agcaggggag    540
tcctgcagca gctggccccc agtgtgcaga agggtgagaa tgttcacaag cactcgcgcc    600
tggcagaggt cctgcagctg ggttcagaca tcctccccca gtacaagcaa gaggcgccaa    660
agacaccccc tcacatcatc ctacactact gtgtctttaa gaccacatgg gattggatca    720
tcttgatcct gaccttctac acagccatcc tggtcccctta caacgtctcc tttaaaacca    780
ggcagaataa cgtggcctgg ctggtggtgg acagcatcgt ggatgtcatc tttttggtgg    840
acattgtctt gaattttcac accacctttg tcgggccagc gggggaagtg atctctgacc    900
ccaaacttat ccgcatgaac tacctgaaga cgtggtttgt gatcgacctt ctctcctgtt    960
tgccatatga cgtcatcaac gcttttgaga acgtggatga gggcatcagc agcctgttca   1020
gttctctgaa agtcgtgcgg ctgctccgtc tcggacgagt ggcccgcaag ctggaccatt   1080
atatcgagta cggagcggcg gtactggtcc tgctggtgtg cgtgttcggg ctggctgccc   1140
actggatggc ctgcatctgg tacagcattg gggattatga gatctttgat gaagacacca   1200
agaccatccg taacaacagc tggctctacc aactggcatt ggacattggc actccatacc   1260
agtttaatgg gtctggttcg gggaagtggg aaggcgggcc aagcaagaac tccgtataca   1320
tttcctcgct gtacttcacc atgacaagtc tcaccagtgt gggctttggt aacatcgccc   1380
catccacaga catcgagaag atcttcgccg tagccatcat gatgattggc tcccttctgt   1440
atgccaccat ctttgggaat gtgacgacca ttttccagca gatgtatgcc aacaccaaca   1500
ggtatcatga gatgctcaac agcgtccggg atttcctgaa gctctaccag gtgcccaagg   1560
ggctgagcga gcgggtcatg gactacattg tgtctacctg gtccatgtcc cgcggcatcg   1620
acacggagaa ggtcctgcaa atctgccccca aggacatgcg agctgacatt tgcgtacacc   1680
tgaaccgaaa agtgttcaaa gaacaccccg ccttccggct ggccagcgat ggttgcctga   1740
gggccttggc catggagttc cagacagtac actgcgcccc aggggacctc atctatcacg   1800
ccggggagag tgtggacagc ctctgcttcg tggtctcggg ctccctggag gtgatccagg   1860
atgatgaggt ggtggccatc ctagggaaag gagatgtgtt tggggatgtt ttctggaagg   1920
aggctaccct tgcacagtcc tgcgctaatg tccgggcctt gacctactgt gacctgcacg   1980
tgatcaagag ggatgccctg cagaaagtgc tagaattcta cacagccttc tcccactcct   2040 tctccccggaa cctgattctc acctacaatc tgaggaagag gattgtgttc cggaagatca   2100
gcgacgtgaa acgagaagaa gaggagagga tgaaacggaa gaacgaggcc cccccttatcc   2160 tgcctcctga ccaccctgtc aggaggctct tccaaaggtt ccgccagcag aaagaagcca   2220
ggctggcagc cgagagaggt ggccgggacc tggatgacct ggatgtagag aagggcaatg   2280
ccctcacgga ccatacctca gccaaccaca gcctggtgaa ggccagtgtg gtcacggtgc   2340
gtgagagtcc cgccacgcct gtgtccttcc aggcagcctc cacctccaca gtgtcagacc   2400
acgccaagct gcatgcaccg ggatctgagt gcctaggtcc caaggcaggc ggtggcgacc   2460
ctgccaagcg caaaggctgg gcccggttca agatgcctg tgggaagggt gaggattgga   2520
acaaggtgtc caaggcagag tccatggaga cgcttcccga gaggacaaag gcatcgggcg   2580
```

```
aggccacgct gaagaagaca gactcctgtg acagtggaat caccaagagt gacctgcgct    2640
tggacaatgt gggtgaggcc aggagtcccc aggaccggag ccccatcttg gccgaggtca    2700
agcattcttt ctaccccatc cccgagcaga cactgcaggc cacagtgctg gaggtgaagc    2760
atgagctgaa ggaagacatc aaggccttga atgccaaaat gacctccatt gagaagcagc    2820
tgtctgagat cctcaggata ctcatgtcca gagggtcctc ccagtctccg caggacacgt    2880
gtgaggtctc caggccccag tcccagagt cagacagaga cattttggg gcaagctgag     2940 aggatcattt caaaacaaac aaacaaaaaa atcaaagaca aagcctgcc ccctgcccct     3000 gacacttcct accgcaccaa acacatgacc aacaactttc a                       3041
```

<210> SEQ ID NO 21
<211> LENGTH: 960
<212> TYPE: PRT
<213> ORGANISM: Bovine sp.

<400> SEQUENCE: 21

```
Met Thr Met Ala Gly Gly Arg Lys Gly Leu Val Ala Pro Gln Asn Thr
  1               5                  10                  15

Phe Leu Glu Asn Ile Val Arg Arg Ser Asn Asp Thr Asn Phe Val Leu
             20                  25                  30

Gly Asn Ala Gln Ile Val Asp Trp Pro Ile Val Tyr Ser Asn Asp Gly
         35                  40                  45

Phe Cys Lys Leu Ser Gly Tyr His Arg Ala Glu Val Met Gln Lys Ser
     50                  55                  60

Ser Thr Cys Ser Phe Met Tyr Gly Glu Leu Thr Asp Lys Asp Thr Ile
 65                  70                  75                  80

Glu Lys Val Arg Gln Thr Phe Glu Asn Tyr Glu Met Asn Ser Phe Glu
                 85                  90                  95

Ile Leu Met Tyr Lys Lys Asn Arg Thr Pro Val Trp Phe Phe Val Lys
            100                 105                 110

Ile Ala Pro Ile Arg Asn Glu Gln Asp Lys Val Val Leu Phe Leu Cys
        115                 120                 125

Thr Phe Ser Asp Ile Thr Ala Phe Lys Gln Pro Ile Glu Asp Asp Ser
    130                 135                 140

Cys Lys Gly Trp Gly Lys Phe Ala Arg Leu Thr Arg Ala Leu Thr Ser
145                 150                 155                 160

Ser Arg Gly Val Leu Gln Gln Leu Ala Pro Ser Val Gln Lys Gly Glu
                165                 170                 175

Asn Val His Lys His Ser Arg Leu Ala Glu Val Leu Gln Leu Gly Ser
            180                 185                 190

Asp Ile Leu Pro Gln Tyr Lys Gln Glu Ala Pro Lys Thr Pro Pro His
        195                 200                 205

Ile Ile Leu His Tyr Cys Val Phe Lys Thr Thr Trp Asp Trp Ile Ile
    210                 215                 220

Leu Ile Leu Thr Phe Tyr Thr Ala Ile Leu Val Pro Tyr Asn Val Ser
225                 230                 235                 240

Phe Lys Thr Arg Gln Asn Asn Val Ala Trp Leu Val Val Asp Ser Ile
                245                 250                 255

Val Asp Val Ile Phe Leu Val Asp Ile Val Leu Asn Phe His Thr Thr
            260                 265                 270

Phe Val Gly Pro Ala Gly Glu Val Ile Ser Asp Pro Lys Leu Ile Arg
        275                 280                 285

Met Asn Tyr Leu Lys Thr Trp Phe Val Ile Asp Leu Leu Ser Cys Leu
```

-continued

```
                290                 295                 300
Pro Tyr Asp Val Ile Asn Ala Phe Glu Asn Val Asp Glu Gly Ile Ser
305                 310                 315                 320

Ser Leu Phe Ser Ser Leu Lys Val Val Arg Leu Leu Arg Leu Gly Arg
                325                 330                 335

Val Ala Arg Lys Leu Asp His Tyr Ile Glu Tyr Gly Ala Ala Val Leu
                340                 345                 350

Val Leu Leu Val Cys Val Phe Gly Leu Ala Ala His Trp Met Ala Cys
                355                 360                 365

Ile Trp Tyr Ser Ile Gly Asp Tyr Glu Ile Phe Asp Glu Asp Thr Lys
370                 375                 380

Thr Ile Arg Asn Asn Ser Trp Leu Tyr Gln Leu Ala Met Asp Ile Gly
385                 390                 395                 400

Thr Pro Tyr Gln Phe Asn Gly Ser Gly Ser Gly Lys Trp Glu Gly Gly
                405                 410                 415

Pro Ser Lys Asn Ser Val Tyr Ile Ser Ser Leu Tyr Phe Thr Met Thr
                420                 425                 430

Ser Leu Thr Ser Val Gly Phe Gly Asn Ile Ala Pro Ser Thr Asp Ile
                435                 440                 445

Glu Lys Ile Phe Ala Val Ala Ile Met Met Ile Gly Ser Leu Leu Tyr
                450                 455                 460

Ala Thr Ile Phe Gly Asn Val Thr Thr Ile Phe Gln Gln Met Tyr Ala
465                 470                 475                 480

Asn Thr Asn Arg Tyr His Glu Met Leu Asn Ser Val Arg Asp Phe Leu
                485                 490                 495

Lys Leu Tyr Gln Val Pro Lys Gly Leu Ser Glu Arg Val Met Asp Tyr
                500                 505                 510

Ile Val Ser Thr Trp Ser Met Ser Arg Gly Ile Asp Thr Glu Lys Val
                515                 520                 525

Leu Gln Ile Cys Pro Lys Asp Met Arg Ala Asp Ile Cys Val His Leu
                530                 535                 540

Asn Arg Lys Val Phe Lys Glu His Pro Ala Phe Arg Leu Ala Ser Asp
545                 550                 555                 560

Gly Cys Leu Arg Ala Leu Ala Met Glu Phe Gln Thr Val His Cys Ala
                565                 570                 575

Pro Gly Asp Leu Ile Tyr His Ala Gly Glu Ser Val Asp Ser Leu Cys
                580                 585                 590

Phe Val Val Ser Gly Ser Leu Glu Val Ile Gln Asp Asp Glu Val Val
                595                 600                 605

Ala Ile Leu Gly Lys Gly Asp Val Phe Gly Asp Val Phe Trp Lys Glu
                610                 615                 620

Ala Thr Leu Ala Gln Ser Cys Ala Asn Val Arg Ala Leu Thr Tyr Cys
625                 630                 635                 640

Asp Leu His Val Ile Lys Arg Asp Ala Leu Gln Lys Val Leu Glu Phe
                645                 650                 655

Tyr Thr Ala Phe Ser His Ser Phe Ser Arg Asn Leu Ile Leu Thr Tyr
                660                 665                 670

Asn Leu Arg Lys Arg Ile Val Phe Arg Lys Ile Ser Asp Val Lys Arg
                675                 680                 685

Glu Glu Glu Glu Arg Met Lys Arg Lys Asn Glu Ala Pro Leu Ile Leu
                690                 695                 700

Pro Pro Asp His Pro Val Arg Arg Leu Phe Gln Arg Phe Arg Gln Gln
705                 710                 715                 720
```

-continued

Lys Glu Ala Arg Leu Ala Ala Glu Arg Gly Gly Arg Asp Leu Asp Asp
                725                 730                 735

Leu Asp Val Glu Lys Gly Ser Val Leu Thr Glu His Ser His His Gly
            740                 745                 750

Leu Ala Lys Ala Ser Val Val Thr Val Arg Glu Ser Pro Ala Thr Pro
        755                 760                 765

Val Ala Phe Pro Ala Ala Ala Pro Ala Gly Leu Asp His Ala Arg
    770                 775                 780

Leu Gln Ala Pro Gly Ala Glu Gly Leu Gly Pro Lys Ala Gly Gly Ala
785                 790                 795                 800

Asp Cys Ala Lys Arg Lys Gly Trp Ala Arg Phe Lys Asp Ala Cys Gly
                805                 810                 815

Gln Ala Glu Asp Trp Ser Lys Val Ser Lys Ala Glu Ser Met Glu Thr
            820                 825                 830

Leu Pro Glu Arg Thr Lys Ala Ala Gly Glu Ala Thr Leu Lys Lys Thr
        835                 840                 845

Asp Ser Cys Asp Ser Gly Ile Thr Lys Ser Asp Leu Arg Leu Asp Asn
    850                 855                 860

Val Gly Glu Ala Arg Ser Pro Gln Asp Arg Ser Pro Ile Leu Ala Glu
865                 870                 875                 880

Val Lys His Ser Phe Tyr Pro Ile Pro Glu Gln Thr Leu Gln Ala Ala
                885                 890                 895

Val Leu Glu Val Lys His Glu Leu Lys Glu Asp Ile Lys Ala Leu Ser
            900                 905                 910

Thr Lys Met Thr Ser Ile Glu Lys Gln Leu Ser Glu Ile Leu Arg Ile
        915                 920                 925

Leu Thr Ser Arg Arg Ser Ser Gln Ser Pro Gln Glu Leu Phe Glu Ile
    930                 935                 940

Ser Arg Pro Gln Ser Pro Glu Ser Glu Arg Asp Ile Phe Gly Ala Ser
945                 950                 955                 960

<210> SEQ ID NO 22
<211> LENGTH: 987
<212> TYPE: PRT
<213> ORGANISM: Bovine sp.

<400> SEQUENCE: 22

Met Thr Met Ala Gly Gly Arg Lys Gly Leu Val Ala Pro Gln Asn Thr
1               5                   10                  15

Phe Leu Glu Asn Ile Val Arg Arg Ser Asn Asp Thr Asn Phe Val Leu
            20                  25                  30

Gly Asn Ala Gln Ile Val Asp Trp Pro Ile Val Tyr Ser Asn Asp Gly
        35                  40                  45

Phe Cys Lys Leu Ser Gly Tyr His Arg Ala Glu Val Met Gln Lys Ser
    50                  55                  60

Ser Thr Cys Ser Phe Met Tyr Gly Glu Leu Thr Asp Lys Asp Thr Ile
65                  70                  75                  80

Glu Lys Val Arg Gln Thr Phe Glu Asn Tyr Glu Met Asn Ser Phe Glu
                85                  90                  95

Ile Leu Met Tyr Lys Lys Asn Arg Thr Pro Val Trp Phe Phe Val Lys
            100                 105                 110

Ile Ala Pro Ile Arg Asn Glu Gln Asp Lys Val Val Leu Phe Leu Cys
        115                 120                 125

Thr Phe Ser Asp Ile Thr Ala Phe Lys Gln Pro Ile Glu Asp Asp Ser

```
            130                 135                 140
Cys Lys Gly Trp Gly Lys Phe Ala Arg Leu Thr Arg Ala Leu Thr Ser
145                 150                 155                 160

Ser Arg Gly Val Leu Gln Gln Leu Ala Pro Ser Val Gln Lys Gly Glu
                165                 170                 175

Asn Val His Lys His Ser Arg Leu Ala Glu Val Leu Gln Leu Gly Ser
            180                 185                 190

Asp Ile Leu Pro Gln Tyr Lys Gln Glu Ala Pro Lys Thr Pro Pro His
            195                 200                 205

Ile Ile Leu His Tyr Cys Val Phe Lys Thr Thr Trp Asp Trp Ile Ile
210                 215                 220

Leu Ile Leu Thr Phe Tyr Thr Ala Ile Leu Val Pro Tyr Asn Val Ser
225                 230                 235                 240

Phe Lys Thr Arg Gln Asn Asn Val Ala Trp Leu Val Val Asp Ser Ile
                245                 250                 255

Val Asp Val Ile Phe Leu Val Asp Ile Val Leu Asn Phe His Thr Thr
                260                 265                 270

Phe Val Gly Pro Ala Gly Glu Val Ile Ser Asp Pro Lys Leu Ile Arg
                275                 280                 285

Met Asn Tyr Leu Lys Thr Trp Phe Val Ile Asp Leu Leu Ser Cys Leu
290                 295                 300

Pro Tyr Asp Val Ile Asn Ala Phe Glu Asn Val Asp Glu Val Ser Ala
305                 310                 315                 320

Phe Met Gly Asp Pro Gly Lys Ile Gly Phe Ala Asp Gln Ile Pro Pro
                325                 330                 335

Pro Leu Glu Gly Arg Glu Ser Gln Gly Ile Ser Ser Leu Phe Ser Ser
            340                 345                 350

Leu Lys Val Val Arg Leu Leu Arg Leu Gly Arg Val Ala Arg Lys Leu
            355                 360                 365

Asp His Tyr Ile Glu Tyr Gly Ala Ala Val Leu Val Leu Leu Val Cys
            370                 375                 380

Val Phe Gly Leu Ala Ala His Trp Met Ala Cys Ile Trp Tyr Ser Ile
385                 390                 395                 400

Gly Asp Tyr Glu Ile Phe Asp Glu Asp Thr Lys Thr Ile Arg Asn Asn
                405                 410                 415

Ser Trp Leu Tyr Gln Leu Ala Met Asp Ile Gly Thr Pro Tyr Gln Phe
                420                 425                 430

Asn Gly Ser Gly Ser Gly Lys Trp Glu Gly Gly Pro Ser Lys Asn Ser
            435                 440                 445

Val Tyr Ile Ser Ser Leu Tyr Phe Thr Met Thr Ser Leu Thr Ser Val
450                 455                 460

Gly Phe Gly Asn Ile Ala Pro Ser Thr Asp Ile Glu Lys Ile Phe Ala
465                 470                 475                 480

Val Ala Ile Met Met Ile Gly Ser Leu Leu Tyr Ala Thr Ile Phe Gly
                485                 490                 495

Asn Val Thr Thr Ile Phe Gln Gln Met Tyr Ala Asn Thr Asn Arg Tyr
            500                 505                 510

His Glu Met Leu Asn Ser Val Arg Asp Phe Leu Lys Leu Tyr Gln Val
            515                 520                 525

Pro Lys Gly Leu Ser Glu Arg Val Met Asp Tyr Ile Val Ser Thr Trp
530                 535                 540

Ser Met Ser Arg Gly Ile Asp Thr Glu Lys Val Leu Gln Ile Cys Pro
545                 550                 555                 560
```

```
Lys Asp Met Arg Ala Asp Ile Cys Val His Leu Asn Arg Lys Val Phe
                565                 570                 575
Lys Glu His Pro Ala Phe Arg Leu Ala Ser Asp Gly Cys Leu Arg Ala
            580                 585                 590
Leu Ala Met Glu Phe Gln Thr Val His Cys Ala Pro Gly Asp Leu Ile
        595                 600                 605
Tyr His Ala Gly Glu Ser Val Asp Ser Leu Cys Phe Val Val Ser Gly
    610                 615                 620
Ser Leu Glu Val Ile Gln Asp Asp Val Val Ala Ile Leu Gly Lys
625                 630                 635                 640
Gly Asp Val Phe Gly Asp Val Phe Trp Lys Glu Ala Thr Leu Ala Gln
                645                 650                 655
Ser Cys Ala Asn Val Arg Ala Leu Thr Tyr Cys Asp Leu His Val Ile
            660                 665                 670
Lys Arg Asp Ala Leu Gln Lys Val Leu Glu Phe Tyr Thr Ala Phe Ser
        675                 680                 685
His Ser Phe Ser Arg Asn Leu Ile Leu Thr Tyr Asn Leu Arg Lys Arg
    690                 695                 700
Ile Val Phe Arg Lys Ile Ser Asp Val Lys Arg Glu Glu Glu Glu Arg
705                 710                 715                 720
Met Lys Arg Lys Asn Glu Ala Pro Leu Ile Leu Pro Pro Asp His Pro
                725                 730                 735
Val Arg Arg Leu Phe Gln Arg Phe Arg Gln Gln Lys Glu Ala Arg Leu
            740                 745                 750
Ala Ala Glu Arg Gly Gly Arg Asp Leu Asp Asp Leu Asp Val Glu Lys
        755                 760                 765
Gly Ser Val Leu Thr Glu His Ser His His Gly Leu Ala Lys Ala Ser
    770                 775                 780
Val Val Thr Val Arg Glu Ser Pro Ala Thr Pro Val Ala Phe Pro Ala
785                 790                 795                 800
Ala Ala Ala Pro Ala Gly Leu Asp His Ala Arg Leu Gln Ala Pro Gly
                805                 810                 815
Ala Glu Gly Leu Gly Pro Lys Ala Gly Gly Ala Asp Cys Ala Lys Arg
            820                 825                 830
Lys Gly Trp Ala Arg Phe Lys Asp Ala Cys Gly Gln Ala Glu Asp Trp
        835                 840                 845
Ser Lys Val Ser Lys Ala Glu Ser Met Glu Thr Leu Pro Glu Arg Thr
    850                 855                 860
Lys Ala Ala Gly Glu Ala Thr Leu Lys Lys Thr Asp Ser Cys Asp Ser
865                 870                 875                 880
Gly Ile Thr Lys Ser Asp Leu Arg Leu Asp Asn Val Gly Glu Ala Arg
                885                 890                 895
Ser Pro Gln Asp Arg Ser Pro Ile Leu Ala Glu Val Lys His Ser Phe
            900                 905                 910
Tyr Pro Ile Pro Glu Gln Thr Leu Gln Ala Ala Val Leu Glu Val Lys
        915                 920                 925
His Glu Leu Lys Glu Asp Ile Lys Ala Leu Ser Thr Lys Met Thr Ser
    930                 935                 940
Ile Glu Lys Gln Leu Ser Glu Ile Leu Arg Ile Leu Thr Ser Arg Arg
945                 950                 955                 960
Ser Ser Gln Ser Pro Gln Glu Leu Phe Glu Ile Ser Arg Pro Gln Ser
                965                 970                 975
```

```
Pro Glu Ser Glu Arg Asp Ile Phe Gly Ala Ser
            980                 985
```

<210> SEQ ID NO 23
<211> LENGTH: 989
<212> TYPE: PRT
<213> ORGANISM: Mus sp.

<400> SEQUENCE: 23

```
Met Thr Met Ala Gly Gly Arg Lys Gly Leu Val Ala Pro Gln Asn Thr
 1               5                  10                  15

Phe Leu Glu Asn Ile Val Arg Arg Ser Asn Asp Thr Asn Phe Val Leu
            20                  25                  30

Gly Asn Ala Gln Ile Val Asp Trp Pro Ile Val Tyr Ser Asn Asp Gly
        35                  40                  45

Phe Cys Lys Leu Ser Gly Tyr His Arg Ala Glu Val Met Gln Lys Ser
    50                  55                  60

Ser Ala Cys Ser Phe Met Tyr Gly Glu Leu Thr Asp Lys Asp Thr Val
 65                  70                  75                  80

Glu Lys Val Arg Gln Thr Phe Glu Asn Tyr Glu Met Asn Ser Phe Glu
                85                  90                  95

Ile Leu Met Tyr Lys Lys Asn Arg Thr Pro Val Trp Phe Phe Val Lys
            100                 105                 110

Ile Ala Pro Ile Arg Asn Glu Gln Asp Lys Val Val Leu Phe Leu Cys
        115                 120                 125

Thr Phe Ser Asp Ile Thr Ala Phe Lys Gln Pro Ile Glu Asp Asp Ser
    130                 135                 140

Cys Lys Gly Trp Gly Lys Phe Ala Arg Leu Thr Arg Ala Leu Thr Ser
145                 150                 155                 160

Ser Arg Gly Val Leu Gln Gln Leu Ala Pro Ser Val Gln Lys Gly Glu
                165                 170                 175

Asn Val His Lys His Ser Arg Leu Ala Glu Val Leu Gln Leu Gly Ser
            180                 185                 190

Asp Ile Leu Pro Gln Tyr Lys Gln Glu Ala Pro Lys Thr Pro Pro His
        195                 200                 205

Ile Ile Leu His Tyr Cys Val Phe Lys Thr Thr Trp Asp Trp Ile Ile
    210                 215                 220

Leu Ile Leu Thr Phe Tyr Thr Ala Ile Leu Val Pro Tyr Asn Val Ser
225                 230                 235                 240

Phe Lys Thr Arg Gln Asn Asn Val Ala Trp Leu Val Val Asp Ser Ile
                245                 250                 255

Val Asp Val Ile Phe Leu Val Asp Ile Val Leu Asn Phe His Thr Thr
            260                 265                 270

Phe Val Gly Pro Ala Gly Glu Val Ile Ser Asp Pro Lys Leu Ile Arg
        275                 280                 285

Met Asn Tyr Leu Lys Thr Trp Phe Val Ile Asp Leu Leu Ser Cys Leu
    290                 295                 300

Pro Tyr Asp Val Ile Asn Ala Phe Glu Asn Val Asp Glu Val Ser Ala
305                 310                 315                 320

Phe Met Gly Asp Pro Gly Lys Ile Gly Phe Ala Asp Gln Ile Pro Pro
                325                 330                 335

Pro Leu Glu Gly Arg Glu Ser Gln Gly Ile Ser Ser Leu Phe Ser Ser
            340                 345                 350

Leu Lys Val Val Arg Leu Leu Arg Leu Gly Arg Val Ala Arg Lys Leu
        355                 360                 365
```

```
Asp His Tyr Ile Glu Tyr Gly Ala Ala Val Leu Val Leu Leu Val Cys
    370                 375                 380

Val Phe Gly Leu Ala Ala His Trp Met Ala Cys Ile Trp Tyr Ser Ile
385                 390                 395                 400

Gly Asp Tyr Glu Ile Phe Asp Glu Asp Thr Lys Thr Ile Arg Asn Asn
                    405                 410                 415

Ser Trp Leu Tyr Gln Leu Ala Leu Asp Ile Gly Thr Pro Tyr Gln Phe
                420                 425                 430

Asn Gly Ser Gly Ser Gly Lys Trp Glu Gly Gly Pro Ser Lys Asn Ser
            435                 440                 445

Val Tyr Ile Ser Ser Leu Tyr Phe Thr Met Thr Ser Leu Thr Ser Val
        450                 455                 460

Gly Phe Gly Asn Ile Ala Pro Ser Thr Asp Ile Glu Lys Ile Phe Ala
465                 470                 475                 480

Val Ala Ile Met Met Ile Gly Ser Leu Leu Tyr Ala Thr Ile Phe Gly
                    485                 490                 495

Asn Val Thr Thr Ile Phe Gln Gln Met Tyr Ala Asn Thr Asn Arg Tyr
                500                 505                 510

His Glu Met Leu Asn Ser Val Arg Asp Phe Leu Lys Leu Tyr Gln Val
            515                 520                 525

Pro Lys Gly Leu Ser Glu Arg Val Met Asp Tyr Ile Val Ser Thr Trp
        530                 535                 540

Ser Met Ser Arg Gly Ile Asp Thr Glu Lys Val Leu Gln Ile Cys Pro
545                 550                 555                 560

Lys Asp Met Arg Ala Asp Ile Cys Val His Leu Asn Arg Lys Val Phe
                    565                 570                 575

Lys Glu His Pro Ala Phe Arg Leu Ala Ser Asp Gly Cys Leu Arg Ala
                580                 585                 590

Leu Ala Met Glu Phe Gln Thr Val His Cys Ala Pro Gly Asp Leu Ile
            595                 600                 605

Tyr His Ala Gly Glu Ser Val Asp Ser Leu Cys Phe Val Val Ser Gly
        610                 615                 620

Ser Leu Glu Val Ile Gln Asp Asp Glu Val Val Ala Ile Leu Gly Lys
625                 630                 635                 640

Gly Asp Val Phe Gly Asp Val Phe Trp Lys Glu Ala Thr Leu Ala Gln
                    645                 650                 655

Ser Cys Ala Asn Val Arg Ala Leu Thr Tyr Cys Asp Leu His Val Ile
                660                 665                 670

Lys Arg Asp Ala Leu Gln Lys Val Leu Glu Phe Tyr Thr Ala Phe Ser
            675                 680                 685

His Ser Phe Ser Arg Asn Leu Ile Leu Thr Tyr Asn Leu Arg Lys Arg
        690                 695                 700

Ile Val Phe Arg Lys Ile Ser Asp Val Lys Arg Glu Glu Glu Arg
705                 710                 715                 720

Met Lys Arg Lys Asn Glu Ala Pro Leu Ile Leu Pro Pro Asp His Pro
                    725                 730                 735

Val Arg Arg Leu Phe Gln Arg Phe Arg Gln Gln Lys Glu Ala Arg Leu
                740                 745                 750

Ala Ala Glu Arg Gly Gly Arg Asp Leu Asp Asp Leu Asp Val Glu Lys
            755                 760                 765

Gly Asn Ala Leu Thr Asp His Thr Ser Ala Asn His Gly Leu Ala Lys
        770                 775                 780
```

```
Ala Ser Val Val Thr Val Arg Glu Ser Pro Ala Thr Pro Val Ala Phe
785                 790                 795                 800

Gln Ala Ala Thr Thr Ser Thr Met Ser Asp His Ala Lys Leu His Ala
            805                 810                 815

Pro Gly Ser Glu Cys Leu Gly Pro Lys Ala Val Ser Cys Asp Pro Ala
        820                 825                 830

Lys Arg Lys Gly Trp Ala Arg Phe Lys Asp Ala Cys Gly Gln Ala Glu
    835                 840                 845

Asp Trp Ser Lys Val Ser Lys Ala Glu Ser Met Glu Thr Leu Pro Glu
850                 855                 860

Arg Thr Lys Ala Pro Gly Glu Ala Thr Leu Lys Lys Thr Asp Ser Cys
865                 870                 875                 880

Asp Ser Gly Ile Thr Lys Ser Asp Leu Arg Leu Asp Asn Val Gly Glu
            885                 890                 895

Thr Arg Ser Pro Gln Asp Arg Ser Pro Ile Leu Ala Glu Val Lys His
        900                 905                 910

Ser Phe Tyr Pro Ile Pro Glu Gln Thr Leu Gln Ala Ala Val Leu Glu
    915                 920                 925

Val Lys Tyr Glu Leu Lys Glu Asp Ile Lys Ala Leu Asn Ala Lys Met
    930                 935                 940

Thr Ser Ile Glu Lys Gln Leu Ser Glu Ile Leu Arg Ile Leu Met Ser
945                 950                 955                 960

Arg Gly Ser Ala Gln Ser Pro Gln Glu Thr Gly Glu Ile Ser Arg Pro
            965                 970                 975

Gln Ser Pro Glu Ser Asp Arg Asp Ile Phe Gly Ala Ser
        980                 985

<210> SEQ ID NO 24
<211> LENGTH: 962
<212> TYPE: PRT
<213> ORGANISM: Rattus sp.

<400> SEQUENCE: 24

Met Thr Met Ala Gly Gly Arg Lys Gly Leu Val Ala Pro Gln Asn Thr
1               5                   10                  15

Phe Leu Glu Asn Ile Val Arg Arg Ser Asn Asp Thr Asn Phe Val Leu
            20                  25                  30

Gly Asn Ala Gln Ile Val Asp Trp Pro Ile Val Tyr Ser Asn Asp Gly
        35                  40                  45

Phe Cys Lys Leu Ser Gly Tyr His Arg Ala Glu Val Met Gln Lys Ser
    50                  55                  60

Ser Ala Cys Ser Phe Met Tyr Gly Glu Leu Thr Asp Lys Asp Thr Val
65              70                  75                  80

Glu Lys Val Arg Gln Thr Phe Glu Asn Tyr Glu Met Asn Ser Phe Glu
            85                  90                  95

Ile Leu Met Tyr Lys Lys Asn Arg Thr Pro Val Trp Phe Phe Val Lys
            100                 105                 110

Ile Ala Pro Ile Arg Asn Glu Gln Asp Lys Val Val Leu Phe Leu Cys
        115                 120                 125

Thr Phe Ser Asp Ile Thr Ala Phe Lys Gln Pro Ile Glu Asp Asp Ser
    130                 135                 140

Cys Lys Gly Trp Gly Lys Phe Ala Arg Leu Thr Arg Ala Leu Thr Ser
145                 150                 155                 160

Ser Arg Gly Val Leu Gln Gln Leu Ala Pro Ser Val Gln Lys Gly Glu
            165                 170                 175
```

-continued

Asn Val His Lys His Ser Arg Leu Ala Glu Val Leu Gln Leu Gly Ser
            180                 185                 190

Asp Ile Leu Pro Gln Tyr Lys Gln Glu Ala Pro Lys Thr Pro Pro His
            195                 200                 205

Ile Ile Leu His Tyr Cys Val Phe Lys Thr Thr Trp Asp Trp Ile Ile
            210                 215                 220

Leu Ile Leu Thr Phe Tyr Thr Ala Ile Leu Val Pro Tyr Asn Val Ser
225                 230                 235                 240

Phe Lys Thr Arg Gln Asn Asn Val Ala Trp Leu Val Val Asp Ser Ile
            245                 250                 255

Val Asp Val Ile Phe Leu Val Asp Ile Val Leu Asn Phe His Thr Thr
            260                 265                 270

Phe Val Gly Pro Ala Gly Glu Val Ile Ser Asp Pro Lys Leu Ile Arg
            275                 280                 285

Met Asn Tyr Leu Lys Thr Trp Phe Val Ile Asp Leu Leu Ser Cys Leu
            290                 295                 300

Pro Tyr Asp Val Ile Asn Ala Phe Glu Asn Val Asp Glu Gly Ile Ser
305                 310                 315                 320

Ser Leu Phe Ser Ser Leu Lys Val Val Arg Leu Leu Arg Leu Gly Arg
            325                 330                 335

Val Ala Arg Lys Leu Asp His Tyr Ile Glu Tyr Gly Ala Ala Val Leu
            340                 345                 350

Val Leu Leu Val Cys Val Phe Gly Leu Ala Ala His Trp Met Ala Cys
            355                 360                 365

Ile Trp Tyr Ser Ile Gly Asp Tyr Glu Ile Phe Asp Glu Asp Thr Lys
            370                 375                 380

Thr Ile Arg Asn Asn Ser Trp Leu Tyr Gln Leu Ala Leu Asp Ile Gly
385                 390                 395                 400

Thr Pro Tyr Gln Phe Asn Gly Ser Gly Ser Gly Lys Trp Glu Gly Gly
            405                 410                 415

Pro Ser Lys Asn Ser Val Tyr Ile Ser Ser Leu Tyr Phe Thr Met Thr
            420                 425                 430

Ser Leu Thr Ser Val Gly Phe Gly Asn Ile Ala Pro Ser Thr Asp Ile
            435                 440                 445

Glu Lys Ile Phe Ala Val Ala Ile Met Met Ile Gly Ser Leu Leu Tyr
450                 455                 460

Ala Thr Ile Phe Gly Asn Val Thr Thr Ile Phe Gln Gln Met Tyr Ala
465                 470                 475                 480

Asn Thr Asn Arg Tyr His Glu Met Leu Asn Ser Val Arg Asp Phe Leu
            485                 490                 495

Lys Leu Tyr Gln Val Pro Lys Gly Leu Ser Glu Arg Val Met Asp Tyr
            500                 505                 510

Ile Val Ser Thr Trp Ser Met Ser Arg Gly Ile Asp Thr Glu Lys Val
            515                 520                 525

Leu Gln Ile Cys Pro Lys Asp Met Arg Ala Asp Ile Cys Val His Leu
            530                 535                 540

Asn Arg Lys Val Phe Lys Glu His Pro Ala Phe Arg Leu Ala Ser Asp
545                 550                 555                 560

Gly Cys Leu Arg Ala Leu Ala Met Glu Phe Gln Thr Val His Cys Ala
            565                 570                 575

Pro Gly Asp Leu Ile Tyr His Ala Gly Glu Ser Val Asp Ser Leu Cys
            580                 585                 590

-continued

```
Phe Val Val Ser Gly Ser Leu Glu Val Ile Gln Asp Glu Val Val
        595                 600                 605

Ala Ile Leu Gly Lys Gly Asp Val Phe Gly Asp Val Phe Trp Lys Glu
610                 615                 620

Ala Thr Leu Ala Gln Ser Cys Ala Asn Val Arg Ala Leu Thr Tyr Cys
625                 630                 635                 640

Asp Leu His Val Ile Lys Arg Asp Ala Leu Gln Lys Val Leu Glu Phe
                645                 650                 655

Tyr Thr Ala Phe Ser His Ser Phe Ser Arg Asn Leu Ile Leu Thr Tyr
            660                 665                 670

Asn Leu Arg Lys Arg Ile Val Phe Arg Lys Ile Ser Asp Val Lys Arg
        675                 680                 685

Glu Glu Glu Arg Met Lys Arg Lys Asn Glu Ala Pro Leu Ile Leu
690                 695                 700

Pro Pro Asp His Pro Val Arg Arg Leu Phe Gln Arg Phe Arg Gln Gln
705                 710                 715                 720

Lys Glu Ala Arg Leu Ala Ala Glu Arg Gly Gly Arg Asp Leu Asp Asp
                725                 730                 735

Leu Asp Val Glu Lys Gly Asn Ala Leu Thr Asp His Thr Ser Ala Asn
            740                 745                 750

His Gly Leu Ala Lys Ala Ser Val Val Thr Val Arg Glu Ser Pro Ala
        755                 760                 765

Thr Pro Val Ala Phe Gln Ala Ala Ser Thr Ser Thr Val Ser Asp His
770                 775                 780

Ala Lys Leu His Ala Pro Gly Ser Glu Cys Leu Gly Pro Lys Ala Gly
785                 790                 795                 800

Gly Gly Asp Pro Ala Lys Arg Lys Gly Trp Ala Arg Phe Lys Asp Ala
                805                 810                 815

Cys Gly Gln Ala Glu Asp Trp Ser Lys Val Ser Lys Ala Glu Ser Met
            820                 825                 830

Glu Thr Leu Pro Glu Arg Thr Lys Ala Ala Gly Glu Ala Thr Leu Lys
        835                 840                 845

Lys Thr Asp Ser Cys Asp Ser Gly Ile Thr Lys Ser Asp Leu Arg Leu
850                 855                 860

Asp Asn Val Gly Glu Ala Arg Ser Pro Gln Asp Arg Ser Pro Ile Leu
865                 870                 875                 880

Ala Glu Val Lys His Ser Phe Tyr Pro Ile Pro Glu Gln Thr Leu Gln
                885                 890                 895

Ala Thr Val Leu Glu Val Lys Tyr Glu Leu Lys Glu Asp Ile Lys Ala
            900                 905                 910

Leu Asn Ala Lys Met Thr Ser Ile Glu Lys Gln Leu Ser Glu Ile Leu
        915                 920                 925

Arg Ile Leu Met Ser Arg Gly Ser Ser Gln Ser Pro Gln Asp Thr Cys
930                 935                 940

Glu Val Ser Arg Pro Gln Ser Pro Glu Ser Asp Arg Asp Ile Phe Gly
945                 950                 955                 960

Ala Ser
```